United States Patent
Karim et al.

(12)

(10) Patent No.: US 11,098,130 B1
(45) Date of Patent: Aug. 24, 2021

(54) ANTIBODIES AND ANTIBODY FRAGMENTS AGAINST THE CD155 RECEPTOR AND METHODS OF USE THEREOF

(71) Applicant: Neurosurj Research & Development, LLC, Farmingdale, NY (US)

(72) Inventors: Aftab S. Karim, Farmington, NY (US); Robert Holgate, Royston (GB); Arron Hearn, Ely (GB)

(73) Assignee: Tasrif Pharmaceutical, LLC, Farmingdale, NY (US)

( * ) Notice: Subject to any disclaimer, the term of this patent is extended or adjusted under 35 U.S.C. 154(b) by 216 days.

(21) Appl. No.: 16/365,330

(22) Filed: Mar. 26, 2019

Related U.S. Application Data

(63) Continuation of application No. 16/247,278, filed on Jan. 14, 2019, now abandoned, which is a continuation-in-part of application No. 15/227,339, filed on Aug. 3, 2016, now abandoned.

(60) Provisional application No. 62/200,506, filed on Aug. 3, 2015.

(51) Int. Cl.
  *A61K 39/00*  (2006.01)
  *C07K 16/28*  (2006.01)
  *C12N 15/62*  (2006.01)
  *A61K 35/00*  (2006.01)

(52) U.S. Cl.
  CPC .......... *C07K 16/2896* (2013.01); *A61K 35/00* (2013.01); *C12N 15/62* (2013.01); *A61K 2039/505* (2013.01); *C07K 2317/565* (2013.01)

(58) Field of Classification Search
  CPC ............................................. A61K 2039/505
  See application file for complete search history.

(56) References Cited

U.S. PATENT DOCUMENTS

| | | | |
|---|---|---|---|
| 6,518,033 B1 | 2/2003 | Gromeier et al. | |
| 10,546,703 B1 * | 1/2020 | Joo | H01H 13/38 |
| 2007/0041985 A1 | 2/2007 | Unger et al. | |
| 2009/0215175 A1 | 8/2009 | Unger et al. | |

FOREIGN PATENT DOCUMENTS

| | | | | |
|---|---|---|---|---|
| WO | 20040074324 A2 | | 9/2004 | |
| WO | WO-2004074324 A2 | * | 9/2004 | ............ A61K 38/17 |
| WO | 2008133851 A1 | | 11/2008 | |
| WO | 2017021526 A1 | | 2/2017 | |
| WO | 20170149538 A1 | | 9/2017 | |

OTHER PUBLICATIONS

Śledzińska et al. (Mol. Oncol. Dec. 2015; 9 (10): 1936-65).*
Wu et al. (Cancer Immunol. Res. Oct. 2019; 7 (10): 1700-1713).*
Nobis, P., et al. "Production of a monoclonal antibody against an epitope on HeLa cells that is the functional poliovirus binding site." Journal of general virology 66.12 (1985): 2563-2569.

* cited by examiner

*Primary Examiner* — Stephen L Rawlings
(74) *Attorney, Agent, or Firm* — Jones Walker LLP

(57) ABSTRACT

A humanized antibody to the poliovirus receptor can be used to target nucleic acids, proteins, and chemicals to brain cancer cells, thus providing treatment for tumors that are otherwise hard to treat due to the difficulty of getting treatments through the blood brain barrier.

16 Claims, 46 Drawing Sheets
Specification includes a Sequence Listing.

ANTIBODIES AND ANTIBODY FRAGMENTS AGAINST THE CD155 RECEPTOR AND METHODS OF USE THEREOF

CROSS-REFERENCE TO RELATED APPLICATIONS

This application is a continuation of application Ser. No. 16/247,178, filed Jan. 14, 2019, now abandoned, which application is a continuation-in-part of application Ser. No. 15/227,339, filed Aug. 3, 2016, now abandoned, which claims priority to U.S. Provisional Application Ser. No. 62/200,506, filed Aug. 3, 2015, all of which are incorporated by reference herein in their entirety.

FIELD

The disclosure relates generally to treatment of disease utilizing monoclonal antibodies. This disclosure relates specifically to targeting cells expressing CD155 with anti-CD155 antibodies or anti CD155 antibody fragments ("antibody fragments" are referred to herein interchangeably with "antigen-binding fragments").

BACKGROUND

Poliovirus is a human pathogen. It does not infect any other species naturally although it is possible to infect other species in the laboratory.

Only 1% or less of those exposed to the poliovirus suffered the effects of the poliovirus. This suggests that in those that suffer the effects of the virus, the virus has reached the central nervous system before the body's immune system kicks into gear to prevent the attack that results in destruction of body functions. So in those situations it appears that in the vast majority of infections the body's immune system was able to meet the challenge of the new infection and destroy the poliovirus before it destroyed essential parts of the nervous system. In the years before the polio immunization, it appears that immunity was established by infection from a previous infection.

CD155/PVR and family of receptors also known as Nectin, Nectin 2 (CD112) Necl, PVRL1, Necl-1, PVRL4, Necl-4 or Ned 5, poliovirus receptor related 1 protein or poliovirus receptor related 2 protein, PVS, HVED is found in various tissues in humans and other animals. In mice, the murine ortholog of CD155 is known as Tage 4. Whereas this CD155/PVR receptor may have a role in normal development, this receptor is overexpressed in certain pathological conditions including malignancies such as Glioblastoma Multiforme, Ovarian Carcinoma, Colon cancer, Pancreatic cancer and Lung cancer and Malignant Peripheral Nerve Sheath Tumor. CD155/PVR plays a role in cell adhesion, motility, and proliferation. As such, poliovirus has been utilized as vector to deliver genes to target cells overexpressing CD155/PVR receptor.

Very few peptides, proteins, antibodies or other macromolecules make it across the blood brain barrier. The blood brain barrier is formed by capillary endothelial cells, which are connected by tight junctions. The blood brain barrier prevents entry into the central nervous system (CNS) of toxins and microbial pathogens from the blood stream. Additionally, the distribution of a molecule within the brain will vary with its size, shape, charge, composition, and the extent that it binds to blood components. Transferrin and insulin growth factor are known to cross the blood brain barrier. Transferrin is a protein on the surface of blood vessels and it carries iron into the brain. Insulin growth factor may enter the brain as a result of neural activation. Neural activation can affect the permeability of the blood brain barrier. Nishijima et al., Neuron 67:834-846 (2010). Antibodies against the poliovirus receptor have not previously been demonstrated to enter the central nervous system thru any route and anti CD155 antibodies are not known to enter the central nervous system and are not known to transcytose across the blood brain barrier.

Active transporters in the cells import nutrients and regulatory molecules. It has been suggested that poliovirus may enter the CNS through peripheral neurons to the spinal cord and by passing through the blood brain barrier. Coyne et al. states that poliovirus enters cultured human brain microvascular endothelial cells by dynamin and caveolar-dependent endocytosis. The entry depends on intracellular signals trigger by attachment of the poliovirus to the poliovirus receptor.

Monoclonal antibodies can be used against tumors but the blood brain barrier prevents the monoclonal antibodies from entering the brain. Therefore, it is challenging to use monoclonal antibodies against brain tumors in vivo. The specificity of the antibodies allows targeting of the tumor but the restrictive nature of the blood brain barrier and other barriers including the blood-CSF barrier prevents the vast majority of antibodies from entering the central nervous system.

It would therefore be advantageous to have an antibody that can enter the central nervous system either by crossing the blood brain barrier or thru other routes either as a therapeutic in and of itself or as a delivery agent for another therapeutic that is either coupled or fused in order to deliver a therapeutic molecule. In this disclosure, it is shown for the first time that a monoclonal antibody targeting the CD155/PVR can enter the central nervous system upon systemic administration and can cross the blood brain barrier. In an embodiment the monoclonal antibody targeting the CD155/PVR has been utilized to deliver mRNA/genes without the viral vector.

SUMMARY

An embodiment of the disclosure is a method of treating a systemic or neurological disorder in a mammal comprising administering to a patient a composition comprising: a therapeutic agent; and a non-viral ligand capable of binding to CD155, wherein the ligand is conjugated to the therapeutic agent. In an embodiment, the neurological disorder is a primary or metastatic brain tumor. In an embodiment, the neurological disorder is at least one from the group consisting of (i) glioblastoma multiforme; (ii) neuroblastoma; (xx) oligodendroglioma, (xxi) glioma, (xxii) astrocytoma, (xxiii) anaplastic astrocytoma, and (xxiv) malignant meningioma, and (iii) metastatic cancer such as but not limited to metastatic breast cancer; (iv) metastatic lung adencarcinoma (nectin 5); (v) metastatic melanoma (Nectin5). An embodiment of the disclosure is a method of treating a systemic disorder such as (i) ovarian cancer; (ii) AML; (iii) Ewing sarcoma; (iv) leukemia; (v) bladder cancer; (vi) bronchial carcinoma, (vii) cervix carcinoma, (viii) colorectal carcinoma, (ix) epidermoid carcinoma, (x) hepatocellular carcinoma, and (xxv) pancreatic cancer. In an embodiment, the brain tumor is at least one from the group consisting of (i) glioblastoma multiforme; (ii) neuroblastoma; (iii) malignant gliomas, (iv) patois carcinoma, (v) ganglioglioma, (vi) oligodendroglioma, (vii) glioma, (viii) astrocytoma, (ix) anaplastic astrocytoma, and (x) malignant meningioma. In an embodiment, the brain tumor overexpresses CD155. In an embodiment, the ligand is at least one from the group consisting of: (i) an antibody against CD155; (ii) a protein binding to CD155; (iii) a peptide or polypeptide binding to CD155; (iv) a fusion protein or fusion peptide binding to CD155; (v) an aptamer binding to CD155; (vi) CD226; (vii) DNAM1; (viii) a viral peptide; and (ix) synthetic antibodies binding to CD155. In an embodiment, the ligand is one which crosses the blood-brain barrier. In an embodiment, the fusion protein includes a first segment binding to CD155 and a second segment including a toxin. In an embodiment, the aptamer binding to CD155 is at least one from the group consisting of (i) RNA aptamers; (ii) DNA aptamers; (iii) chimeric nucleic acid aptamers; (iv) chemically modified RNA; and chemically modified DNA. In an embodiment, a chemical modification is selected from the group consisting of phosphorothioate, 5 methylcytidine, pseudouridine, and 2'Fluoro, 2 thiouridine. In an embodiment, the therapeutic agent is at least one from the group consisting of (i) a drug; (ii) a prodrug; (iii) siRNA; (iv) antisense DNA or RNA; (v) messenger RNA; and (vi) guide RNA for CRISPR (vii) a plasmid; (vii) a toxin; (viii) a peptide; (ix) a protein; and (x) a gene. In an embodiment, the ligand is capable of binding to Nectin, Nectin 2 (CD112), Necl, PVRL1, Necl-1, PVRL4, Necl-4, poliovirus receptor related 1 protein, or poliovirus receptor related 2 protein. In an embodiment, further comprising a liposome. In an embodiment, the liposome is a pegylated liposome cross-linked to the ligand. In an embodiment, the ligand is a D171 antibody or analogous sequence that binds to CD155. In an embodiment, the anti CD155 antibody specifically binds to any intracellular, transmembrane or extracellular epitope of CD155. In an embodiment, D171 specifically binds to amino acids 35 to 50 of CD155. In an embodiment, the antibody binding to a tumor elicits an immune response against the cancerous growth or tumor. In an embodiment, at least one antibody selected from the group consisting of a full antibody, antibody fragment, Fab, Fab2, Fc, and scv comprise a first component binding to CD155 and a second component binding to an effector cell in order to stimulate antibody-dependent cell-mediated cytotoxicity. In an embodiment, the at least one is selected from monoclonal antibody, polyclonal antibody, humanized antibody, and chimeric antibody. In an embodiment, the effector cell is at least one from the group consisting of natural killer cells and lymphocytes including cytotoxic T cells. In an embodiment, the antibody is administered by at least one method from the group consisting of intravenously, intraarterially, intratumorally, intrathecally, intramuscularly, subcutaneously, intraperitoneally, and via convection-enhanced delivery.

An embodiment of the disclosure is a method of treating a systemic or neurological disorder in a mammal comprising administering to a patient a composition comprising a non-viral ligand capable of binding to CD155, wherein the ligand is conjugated to the therapeutic agent. In an embodiment, at least one antibody selected from the group consisting of a full antibody, antibody fragment, Fab, Fab2, Fc, and scv or other fragments comprise a first component binding to CD155 and a second component binding to an effector cell in order to stimulate antibody-dependent cell-mediated cytotoxicity. An embodiment of the disclosure is a method of delivering a therapeutic agent into the central nervous system either by systemic or local administration. In one embodiment, the anti CD155 antibody or antibody fragment may cross the blood brain barrier of a mammal comprising administering into the bloodstream of the mammal a non-viral ligand targeting CD155 wherein the non-viral ligand is conjugated with a therapeutic agent. In an embodiment, the therapeutic agent is encapsulated into a liposome which is conjugated to the ligand. In an embodiment, the mammal has a brain tumor. In an embodiment, the mammal suffers from an adverse condition of the brain which is not a tumor. In one embodiment the anti CD155 antibody or antibody fragment is itself a therapeutic or it delivers a therapeutic for the treatment of a systemic disorder such as cancer of the pancreas, ovaries, lungs, colon and sarcoma such as MPNST.

An embodiment of the disclosure is a method for delivering antibodies to the brain of a mammal by fusing the therapeutic antibody or fragment of a therapeutic antibody to an Anti CD155 antibody or anti CD155 antibody fragment. In an embodiment, the therapeutic antibody or therapeutic antibody fragment is fused to an anti-CD155 antibody or anti-CD155 antibody by a manner selected from the group consisting of chemically, antibody engineered, or avidin-biotin based crosslinking. In an embodiment, the anti-CD155 antibody or anti-CD155 antibody fragment is therapeutic. In an embodiment, the antibody to be delivered is selected from the group consisting of humanized IgG1 targeting ERBB2 (trastuzumab); humanized IgG1 targeting VEGF (bevacizumab); chimeric human-murine IgG1 targeting EGFR (cetuximab); human IgG2 targeting EGFR (panitumumab); IgG1 targeting CTLA4 (ipilimumab); chimeric human-murine IgG1 targeting CD20 (rituximab); humanized IgG1 targeting CD52 (alemtuzumab); human IgG1 targeting CD20 (ofatumumab); humanized IgG4 targeting CD33 (gemtuzumab ozogamicin); chimeric IgG1 targeting CD30 (bentuximab vedotin); murine IgG1 targeting CD20 (90Y-labelled ibritumomab tiuxetan); murine IgG2 targeting CD20 (125I-labelled tositumomab); and human IgG targeting ecto-domain vimentin (pritumumab).

An embodiment of the disclosure is a composition of matter comprising an humanized antibody to CD-155 conjugated to one of a group consisting of IL-13; IL13 peptide with selective affinity to the IL13 alpha 2 receptor; anti IL13 alpha 2 antibody with selective affinity to the IL13 alpha 2 receptor; humanized IgG1 targeting ERBB2 (trastuzumab); humanized IgG1 targeting VEGF (bevacizumab); chimeric human-murine IgG1 targeting EGFR (cetuximab); human IgG2 targeting EGFR (panitumumab); IgG1 targeting CTLA4 (ipilimumab); chimeric human-murine IgG1 targeting CD20 (rituximab); humanized IgG1 targeting CD52 (alemtuzumab); human IgG1 targeting CD20 (ofatumumab); humanized IgG4 targeting CD33 (gemtuzumab ozogamicin); chimeric IgG1 targeting CD30 (bentuximab vedotin); murine IgG1 targeting CD20 (90Y-labelled ibritumomab tiuxetan); murine IgG2 targeting CD20 (125I-labelled tositumomab); and human IgG targeting ecto-domain vimentin (pritumumab). In an embodiment, the antibody to CD-155 is fused or chemically conjugated to IL-13. In an embodiment, the antibody to CD-155 is conjugated to an IL-13 peptide with affinity for the IL13alpha 2 receptor. In an embodiment, the antibody to CD-155 is conjugated to an anti IL13 alpha 2 antibody with affinity for the IL13alpha 2 receptor. In an embodiment, a nucleic acid-based drug conjugated to an anti-CD155 antibody.

An embodiment of the disclosure is a humanized antibody against a CD155 receptor comprising a selenocysteine or a Fc region enhanced to optimize ADCC or CDCC.

An embodiment of the disclosure is a composition comprising a humanized D171 antibody or an antibody with a sequence similar to the D171 antibody. In an embodiment, the composition further comprises a therapeutic agent.

An embodiment of the disclosure is a humanized Anti CD155 antibody such as the D171 antibody or an antibody with a sequence similar to the D171 antibody comprising a selenocysteine residue greater than 10 amino acids from the C-terminus.

An embodiment of the disclosure is a humanized D171 antibody comprising comprising an Fc region optimized to enhance ADCC.

An embodiment of the disclosure is a humanized D171 antibody comprising optimized for CDC.

An embodiment of the disclosure is a humanized D171 antibody coupled to a contrast agent for MRI/CT.

An embodiment of the disclosure is a humanized D171 antibody coupled to diagnostic agents for a PET scan.

An embodiment of the disclosure is a humanized D171 antibody coupled to a fluorescent probe.

An embodiment of the disclosure is a humanized D171 antibody coupled to a radiosensitizer.

An embodiment of the disclosure is a humanized D171 antibody coupled to a chelator.

An embodiment of the disclosure is a humanized D171 antibody coupled to radioisotopes.

An embodiment of the disclosure is a humanized D171 antibody coupled to a therapeutic agent.

An embodiment of the disclosure is a humanized D171 antibody, wherein the humanized D171 antibody is a therapeutic.

An embodiment of the disclosure is a method of identifying the extent of a tumor in a mammal overexpressing a CD155 receptor comprising the steps of administering a non-viral ligand targeting the CD 155 receptor which has been conjugated with a label; and imaging the brain tumor. In an embodiment, the label is at least one selected from the group consisting of a radioisotope, a chromophore, a fluorophore, and an enzyme. In an embodiment, the label is selected from the group consisting of a gamma ray or positron emitting radioisotope, a magnetic resonance imaging contrast agent, an X-ray contrast agent, and an ultrasound contrast agent. In an embodiment, a selenocysteine residue is utilized to conjugate the label with the non-viral ligand. In an embodiment, the imaging is conducted through at least one technique selected from the group consisting of CT, ultrasound, MRI, SPECT and PET. In an embodiment, the imaging is performed during at least one time selected from the group consisting of pre-operative, intra-operative, and post-operative.

An embodiment of the disclosure is a method of treating a neurological disorder in a mammal comprising administering to a patient a composition comprising: a therapeutic agent; and a non-viral ligand capable of binding to PECAM, wherein the ligand is conjugated to the therapeutic agent. In an embodiment, the composition further comprises a therapeutic agent.

An embodiment of the disclosure is a humanized or chimeric antibody against PECAM. In an embodiment, the antibody is monoclonal. In an embodiment, the antibody is polyclonal.

An embodiment of the disclosure is a method of treating a neurological disorder in a mammal comprising administering to a patient a composition comprising: a therapeutic agent; and a humanized non-viral ligand capable of binding to a CD99 receptor, wherein the ligand is conjugated to the therapeutic agent.

An embodiment of the disclosure is a humanized or chimeric antibody against CD99. In an embodiment, the antibody is monoclonal. In an embodiment, the antibody is polyclonal.

An embodiment of the disclosure is a method of delivering a therapeutic agent across the blood brain barrier where the therapeutic agent is conjugated to an anti-CD155 antibody or anti-CD155 antibody fragment or an anti CD155 camelid antibody. The foregoing has outlined rather broadly the features of the present disclosure in order that the detailed description that follows may be better understood. Additional features and advantages of the disclosure will be described hereinafter, which form the subject of the claims.

An embodiment of the disclosure is a method of treating a neurological disorder in a mammal comprising administering to the mammal a composition comprising: a therapeutic agent; and a non-viral ligand capable of binding to CD155, wherein the ligand is conjugated to the therapeutic agent.

In an embodiment, the neurological disorder is at least one from the group consisting of (i) glioblastoma multiforme; (ii) neuroblastoma; (iii) breast cancer; (iv) lung adencarcinoma (nectin 5); (v) melanoma (Nectin5); (vi) ovarian cancer; (vii) AML; (viii) Ewing sarcoma; (ix) leukemia; (x) bladder cancer; (xi) bronchial carcinoma; (xii) cervix carcinoma; (xiii) colorectal carcinoma; (xiv) epidermoid carcinoma; (xv) hepatocellular carcinoma; (xvi) malignant gliomas; (xvii) mammary carcinoma; (xviii) patois carcinoma; (xix) ganglioglioma; (xx) oligodendroglioma; (xxi) glioma; (xxii) astrocytoma; (xxiii) anaplastic astrocytoma; and (xxiv) malignant meningioma; and (xxv) pancreatic cancer; and (xxvi) sarcoma.

In an embodiment, the sarcoma is a malignant peripheral nerve sheath tumor.

In an embodiment, wherein the neurological disorder is a primary or metastatic brain tumor.

In an embodiment, the primary or metastatic brain tumor overexpresses CD155.

In an embodiment, the ligand is at least one from the group consisting of: (i) an antibody against CD155; (ii) an antibody fragment against CD155; (iii) an anti CD155 camelid antibody (iv) a protein binding to CD155; (v) a peptide or polypeptide binding to CD155; (vi) a fusion protein or fusion peptide binding to CD155; (vii) an aptamer binding to CD155r; (viii) CD226; (ix) DNAM1; (x) a viral peptide; and (xi) synthetic antibodies binding to CD155.

In an embodiment, the ligand is expressed as part of a therapeutic Chimeric Antigen Receptor T-cell (CART) for the treatment of CD155 positive tumors.

In an embodiment, the ligand is capable of crossing the blood-brain barrier.

In an embodiment, the fusion protein includes a first segment binding to CD155 and a second segment including a toxin.

In an embodiment, the aptamer binding to CD155 is at least one from the group consisting of (i) RNA aptamers; (ii) DNA aptamers; (iii) chimeric nucleic acid aptamers; (iv) chemically modified RNA; and (v) chemically modified DNA.

In an embodiment, the RNA or DNA is chemically modified with a chemical selected from the group consisting of phosphorothioate, 5 methylcytidine, pseudouridine, 2'Fluoro, and 2 thiouridine.

In an embodiment, the therapeutic agent is at least one from the group consisting of (i) a drug; (ii) a prodrug; (iii) siRNA; (iv) antisense DNA (v) antisense RNA; (vi) messenger RNA; (vii) guide RNA for CRISPR (viii) a plasmid; (ix) a toxin; (x) a peptide; (xi) a protein; (xii) a gene (xiii) a plasmid, and (xiv) cell therapeutics.

In an embodiment, the cell therapeutics comprise NK cells expressing the ligand, NK cells expressing a fragment of the ligand, Chimeric Antigen Receptor T cells expressing the ligand, or Chimeric Antigen Receptor T cells expressing a fragment of the ligand.

In an embodiment, the ligand is capable of binding to Nectin, Nectin 2 (CD112), Necl, PVRL1, Necl-1, PVRL4, Necl-4, poliovirus receptor related 1 protein, or poliovirus receptor related 2 protein.

In an embodiment, the method further comprises a liposome or a polyethylenimine (PEI) polymer.

In an embodiment, the ligand is a D171 antibody or antibody with at least 90% homology to the D171 antibody that binds to CD155.

In an embodiment, the D171 antibody or antibody with at least 90% homology to the D171 antibody specifically binds to an intracellular, transmembrane or extracellular epitope of CD155.

In an embodiment, the D171 antibody or antibody with at least 90% homology to the D171 antibody specifically binds to amino acids 35 to 50 of CD155.

In an embodiment, the antibody binding to the primary or metastatic brain tumor elicits an immune response against the primary or metastatic tumor.

In an embodiment, at least one antibody selected from the group consisting of a full antibody, antibody fragment, Fab, Fab2, Fc, scv, or a camelid antibody comprise a first component binding to CD155 and a second component binding to an effector cell in order to stimulate antibody-dependent cell-mediated cytotoxicity.

In an embodiment, the at least one selected from the group consisting of a full antibody, antibody fragment, Fab, Fab2, Fc, scv, or a camelid antibody is selected from monoclonal antibody, polyclonal antibody, humanized antibody, chimeric antibody, and a camelid antibody.

In an embodiment, the effector cell is at least one from the group consisting of natural killer cells and cytotoxic T cells.

In an embodiment, the antibody is administered by at least one method from the group consisting of intravenously, intra-arterially, intratumorally, intrathecally, intramuscularly, subcutaneously, intraperitoneally, and via convection-enhanced delivery.

An embodiment of the disclosure is a method of treating a neurological disorder in a mammal comprising administering to the mammal a composition comprising: a therapeutic agent; and a non-viral ligand capable of binding to at least one selected from the group consisting of PECAM and a CD99 receptor, wherein the ligand is conjugated to the therapeutic agent.

An embodiment of the disclosure is a method of delivering a therapeutic agent across the blood brain barrier of a mammal comprising administering into the bloodstream of the mammal a non-viral ligand targeting CD155, wherein the non-viral ligand is conjugated with a therapeutic agent.

In an embodiment, the therapeutic agent is encapsulated into a liposome conjugated to the ligand.

In an embodiment, the mammal has a brain tumor.

In an embodiment, the mammal has an adverse condition of the brain, wherein the adverse condition of the brain is not a tumor.

In an embodiment, the therapeutic agent is conjugated to an anti-CD155 antibody, anti-CD155 antibody fragment, or an anti CD155 camelid antibody.

In an embodiment, the therapeutic agent is conjugated to an anti-CD155 antibody, anti-CD155 antibody fragment, or an anti CD155 camelid antibody and is administered to a mammal for treatment of motor neurons in the brain, brainstem, spinal cord, or other CD155-expressing cells.

An embodiment of the disclosure is a method for delivering antibodies to the brain of a mammal by fusing the therapeutic antibody or fragment of a therapeutic antibody to an anti CD155 antibody or anti CD155 antibody fragment or an anti CD155 camelid antibody.

In an embodiment, the therapeutic antibody or therapeutic antibody fragment is fused to an anti-CD155 antibody or anti-CD155 antibody by a manner selected from the group consisting of chemically, antibody engineered, or avidin-biotin based crosslinking.

In an embodiment, the anti-CD155 antibody or anti-CD155 antibody fragment is therapeutic.

In an embodiment, the antibody to be delivered is selected from the group consisting of humanized IgG1 targeting ERBB2 (trastuzumab); humanized IgG1 targeting VEGF (bevacizumab); chimeric human-murine IgG1 targeting EGFR (cetuximab); human IgG2 targeting EGFR (panitumumab); IgG1 targeting CTLA4 (ipilimumab); chimeric human-murine IgG1 targeting CD20 (rituximab); humanized IgG1 targeting CD52 (alemtuzumab); human IgG1 targeting CD20 (ofatumumab); humanized IgG4 targeting CD33 (gemtuzumab ozogamicin); chimeric IgG1 targeting CD30 (bentuximab vedotin); murine IgG1 targeting CD20 (90Y-labelled ibritumomab tiuxetan); murine IgG2 targeting CD20 (125I-labelled tositumomab); and human IgG targeting ecto-domain vimentin (pritumumab).

An embodiment of the disclosure is a method of identifying the extent of a tumor in a mammal overexpressing a CD155 receptor comprising the steps of administering a non-viral ligand targeting the CD 155 receptor which has been conjugated with a label; and imaging the brain tumor.

In an embodiment, the label is at least one selected from the group consisting of a radioisotope, a chromophore, a fluorophore, and an enzyme.

In an embodiment, the label is selected from the group consisting of a gamma ray or positron emitting radioisotope, a magnetic resonance imaging contrast agent, an X-ray contrast agent, and an ultrasound contrast agent.

In an embodiment, a selenocysteine residue is utilized to conjugate the label with the non-viral ligand.

In an embodiment, the imaging is conducted through at least one technique selected from the group consisting of CT, ultrasound, MRI, SPECT and PET.

In an embodiment, the imaging is performed during at least one time selected from the group consisting of pre-operative, intra-operative, and post-operative.

An embodiment of the disclosure is a composition of matter comprising an humanized antibody to CD-155 conjugated to one of a group consisting of IL-13; IL13 peptide with selective affinity to the IL13 alpha 2 receptor; anti IL13 alpha 2 antibody with selective affinity to the IL13 alpha 2 receptor; humanized IgG1 targeting ERBB2 (trastuzumab); humanized IgG1 targeting VEGF (bevacizumab); chimeric human-murine IgG1 targeting EGFR (cetuximab); human IgG2 targeting EGFR (panitumumab); IgG1 targeting CTLA4 (ipilimumab); chimeric human-murine IgG1 targeting CD20 (rituximab); humanized IgG1 targeting CD52 (alemtuzumab); human IgG1 targeting CD20 (ofatumumab); humanized IgG4 targeting CD33 (gemtuzumab ozogamicin); chimeric IgG1 targeting CD30 (bentuximab vedotin); murine IgG1 targeting CD20 ($^{90}$Y-labelled ibritumomab tiuxetan); murine IgG2 targeting CD20 ($^{125}$I-labelled tositumomab); and human IgG targeting ecto-domain vimentin (pritumumab).

In an embodiment, the antibody to CD-155 is fused or chemically conjugated to IL-13.

In an embodiment, the antibody to CD-155 is conjugated to an IL-13 peptide with affinity for the IL13alpha 2 receptor.

In an embodiment, the antibody to CD-155 is conjugated to an anti IL13 alpha 2 antibody with affinity for the IL13alpha 2 receptor.

In an embodiment, the composition of matter further comprises a nucleic acid-based drug conjugated to an anti-CD155 antibody or anti CD155 camelid antibody.

An embodiment of the disclosure is a humanized antibody against a CD155 receptor comprising a selenocysteine or a Fc region enhanced to optimize ADCC or CDCC.

An embodiment of the disclosure is a composition comprising a humanized D171 antibody or humanized antibody with a similar sequence to the D171 antibody.

In an embodiment, the composition further comprises a therapeutic agent.

An embodiment of the disclosure is a humanized D171 antibody or humanized antibody with a similar sequence to the D171 antibody comprising at least one selected from the group consisting of a selenocysteine residue greater than 10 amino acids from the C-terminus; an Fc region optimized to enhance ADCC; optimization for CDC; coupling to a contrast agent for MRI/CT; coupling to diagnostic agents for a PET scan; coupling to a fluorescent probe; coupling to a radiosensitizer; coupling to a chelator; coupling to radioisotopes; coupling to a therapeutic agent; and wherein a humanized anti CD155 antibody is a therapeutic.

An embodiment of the disclosure is a humanized or chimeric antibody against one selected from the group consisting of PECAM and CD99.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

Bottom Row: Ex vivo imaging of mice with G1261-Luc GBM tumors

Top Row: Ex Vivo Imaging of Mice treated with PBS or 50 ug IV fluorescent labeled Anti CD155 antibody. Column 2 and Column 4 administered IV mouse Anti-CD155 antibody labeled with fluorescent probe. Column 1 and Column 3 administered phosphate buffer solution.

Figure 6:
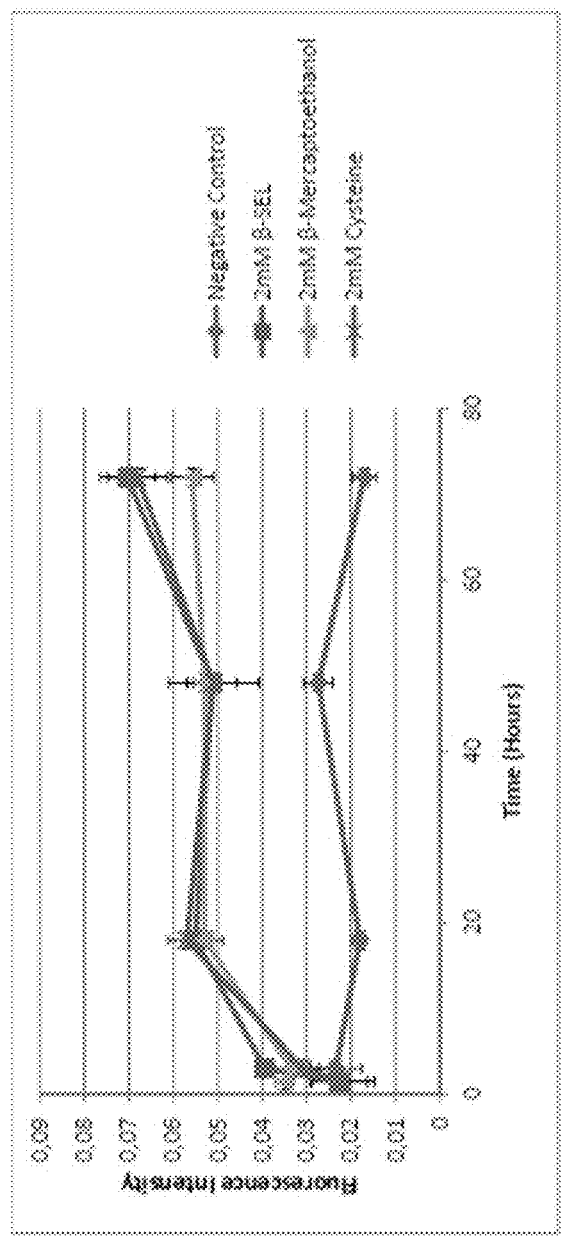

FIG. 6 is a graph of fluorescence intensity versus time for 2 mM β-SEL, β-mercaptoethanol, and 2 mM cysteine. These results show relative reactivity of Selenocysteine and Cysteine towards Maleimide. Antibodies and polypeptides containing Selenocysteine may permit conjugation of the protein or polypeptide to reporter molecules containing a reactive maleimide moiety.

Figure 7:
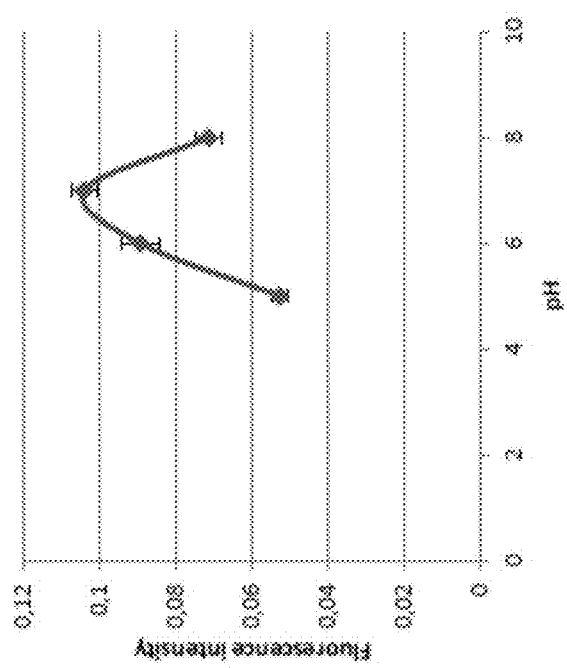

FIG. 7 is a graph of fluorescence intensity against pH.

Figure 8:
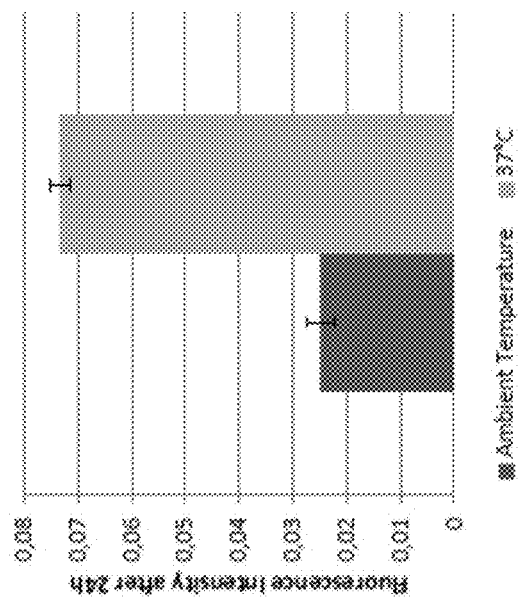

FIG. 8 is a graph of fluorescence intensity after 24 hr at ambient temperature and at 37° C.

Figure 9:
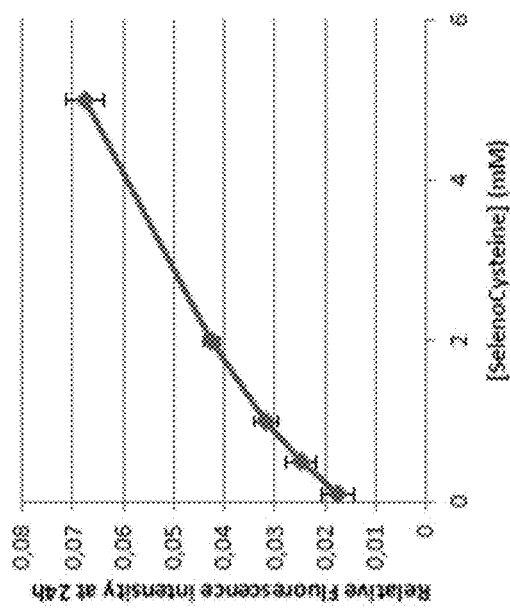

FIG. 9 is a graph of fluorescence intensity after 24 hr at varying concentrations of selenocysteine.

Figure 10:
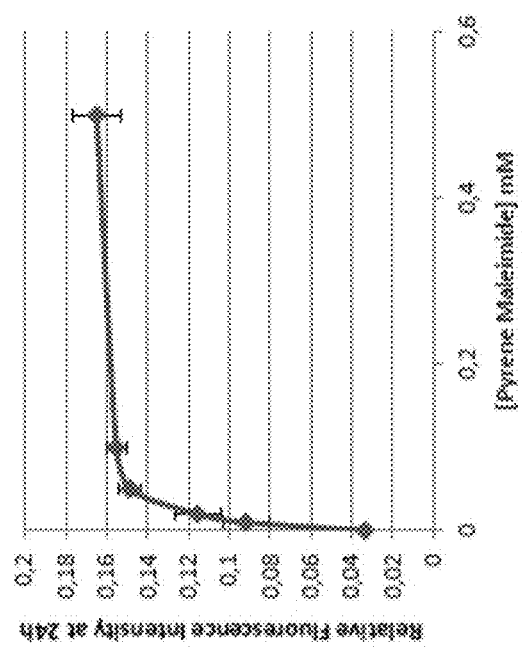

FIG. 10 is a graph of fluorescence intensity after 24 hr at varying concentrations of pyrene maleimide.

Figure 11:
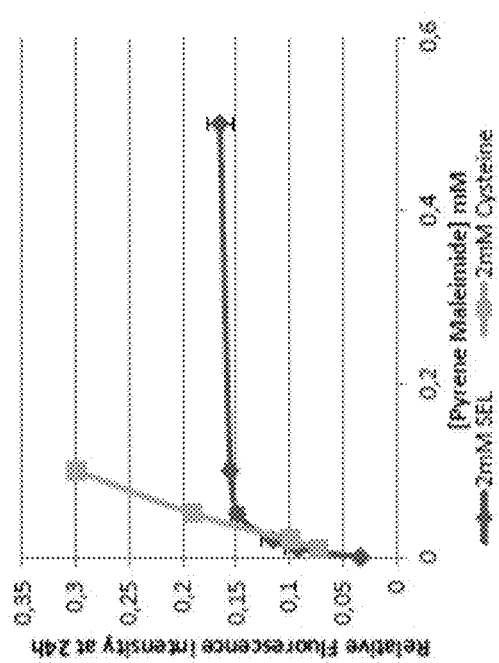

FIG. 11 is a graph of fluorescence intensity after 24 hr at varying concentrations of pyrene maleimide for 2 mM SEL and 2 mM cysteine.

Figure 12:
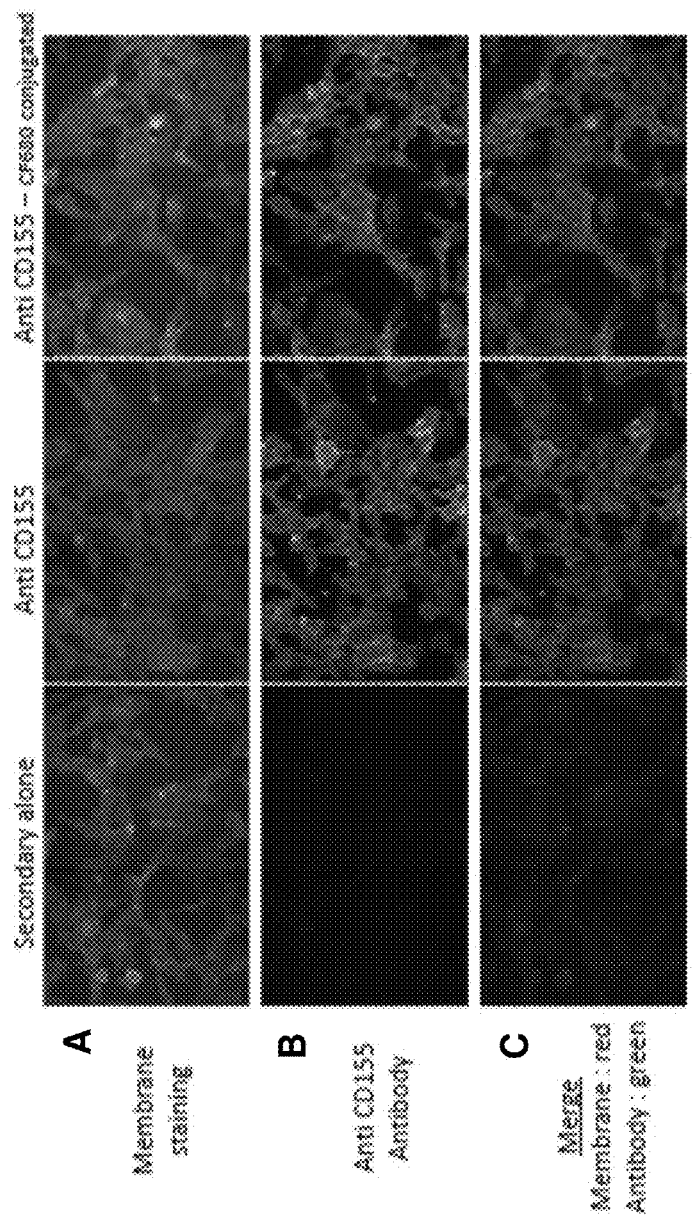

FIG. 12 depicts staining with anti-CD155 antibodies (A) membrane staining; (B) anti-CD155 antibody staining; and (C) membrane and anti-CD155 staining.

Figure 13:
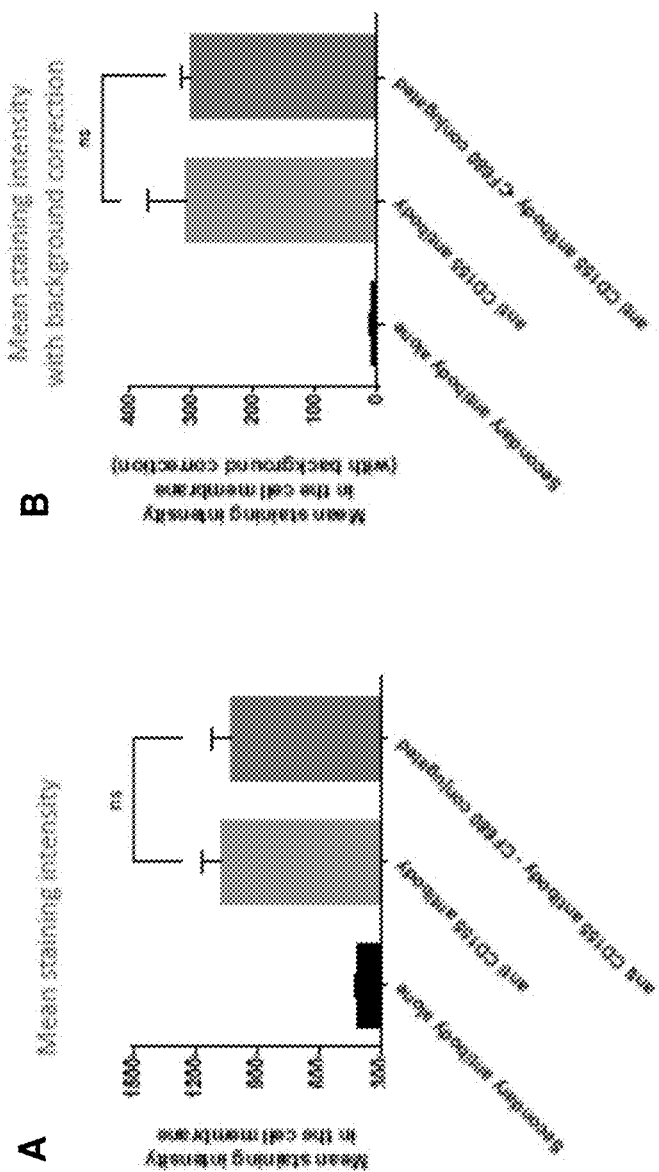

FIG. 13 depicts analyses of anti-CD155 antibody staining (A) mean staining intensity; (B) mean staining intensity with background correction.

Figure 14:
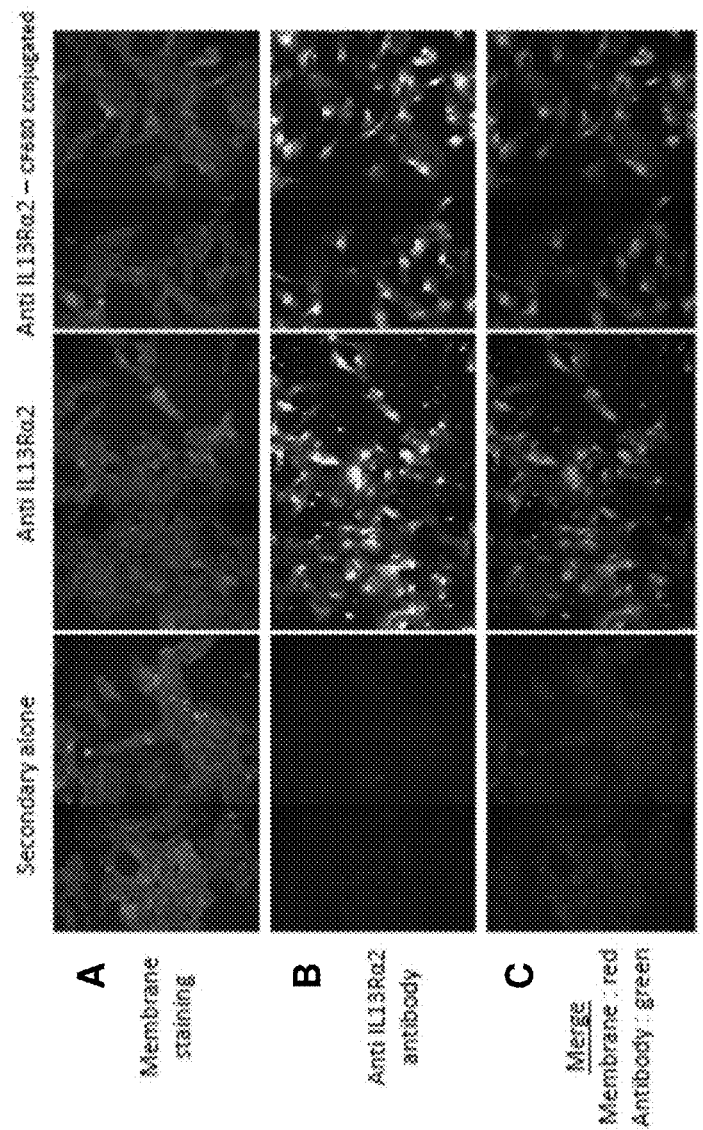

FIG. 14 depicts staining with anti-IL13Ra2 (IL13 alpha 2 Receptor) antibodies (A) membrane staining; (B) anti-IL13Ra2 antibody staining; and (C) membrane and anti-IL13Ra2 staining.

Figure 15:
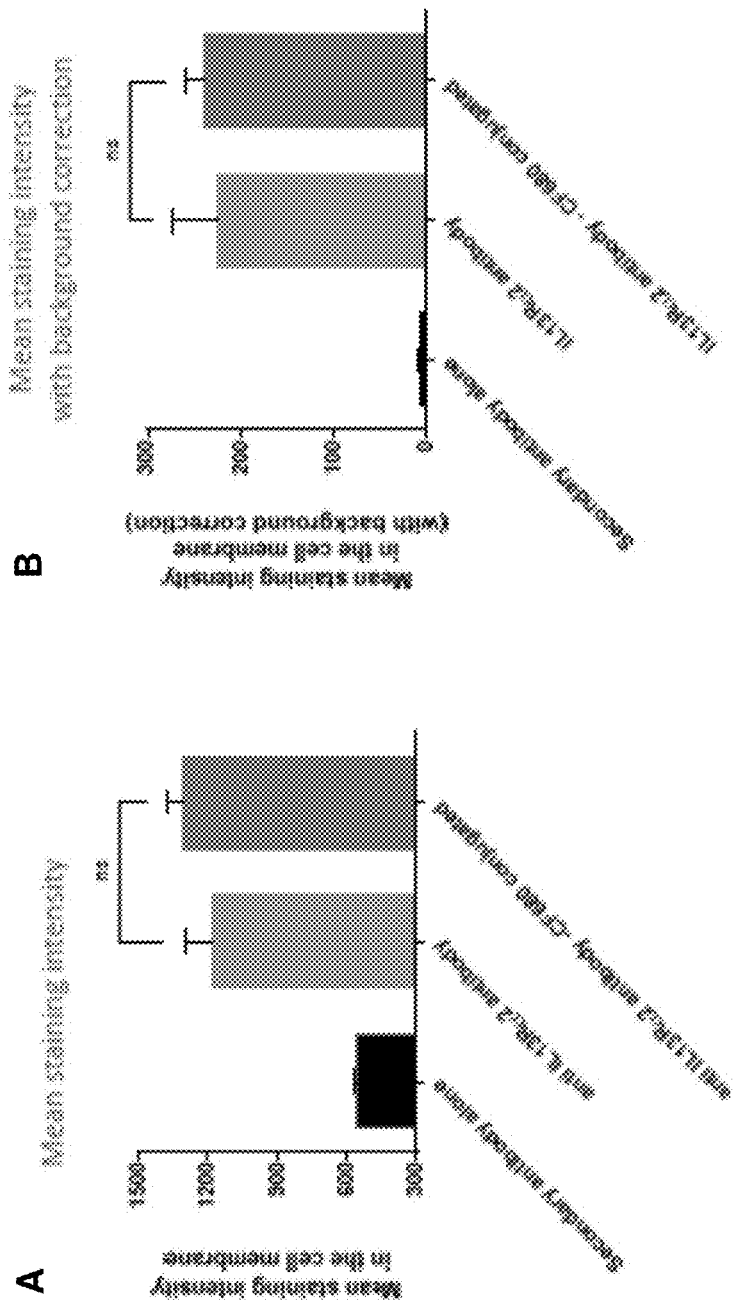

FIG. 15 depicts analyses of anti-IL13Ra2 antibody staining (A) mean staining intensity; (B) mean staining intensity with background correction.

Figure 16:
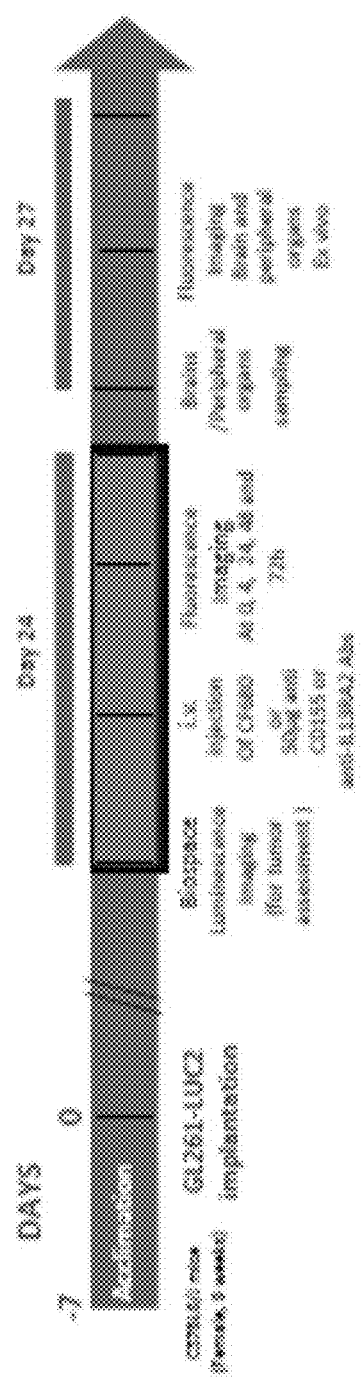

FIG. 16 depicts an experimental timeline to evaluate the ability of labeled anti-CD155 and anti-IL13α2R antibodies to cross the blood-brain-barrier in vivo in mouse models.

Figure 17:
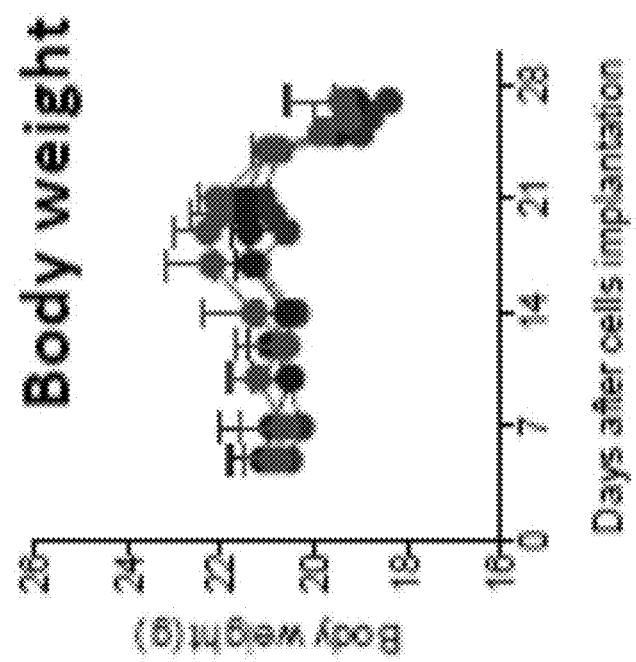

FIG. 17 depicts a graph of body weight versus days after cell implantation.

Figure 18:
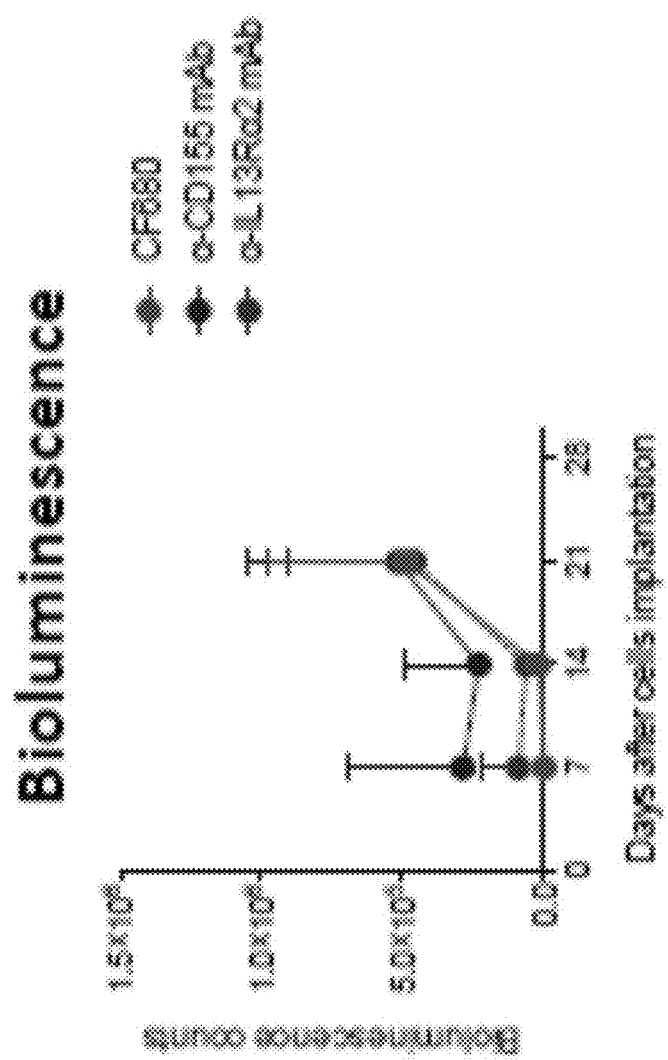

FIG. 18 depicts a graph of bioluminescence versus days after cell implantation.

Figure 19:
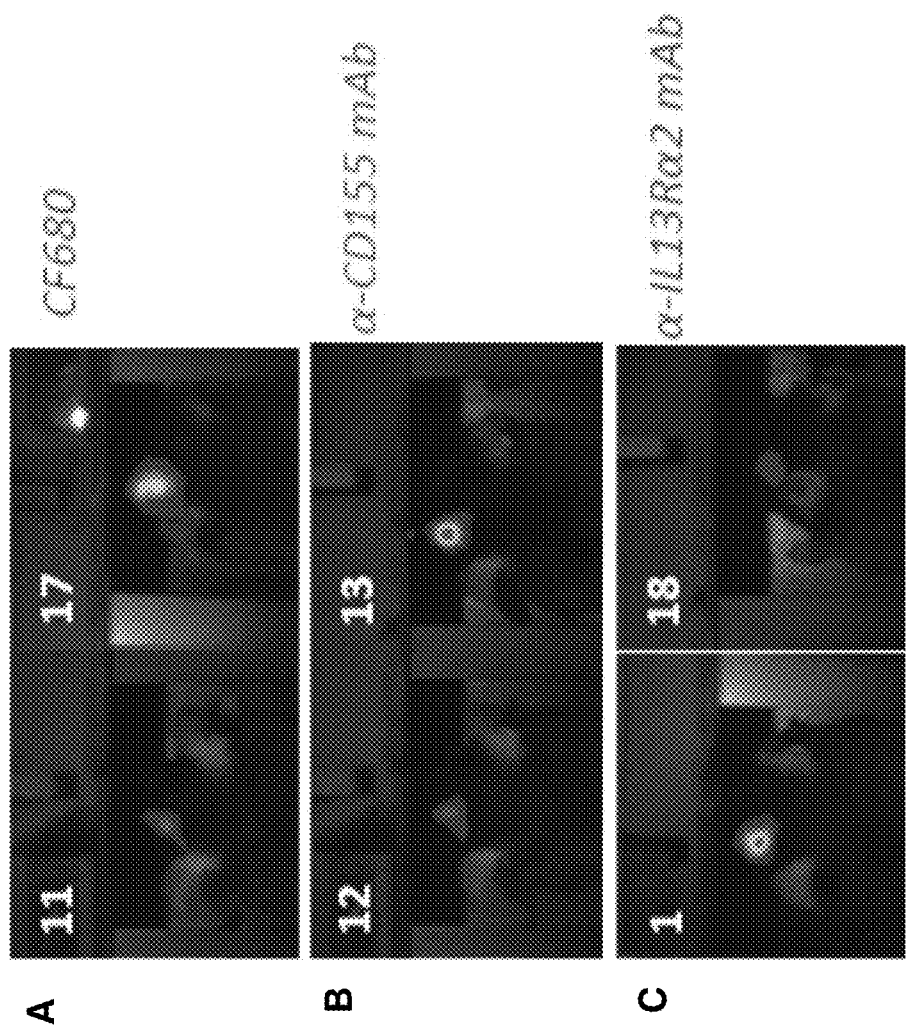

FIG. 19 depicts localization of (A) CF680; (B) α-CD155 mAb (CF680 labeled Anti CD155 Antibody); (C) α-IL13Ra2 mAb (CF680 labeled Anti IL13 alpha 2 Antibody).

Figure 20:
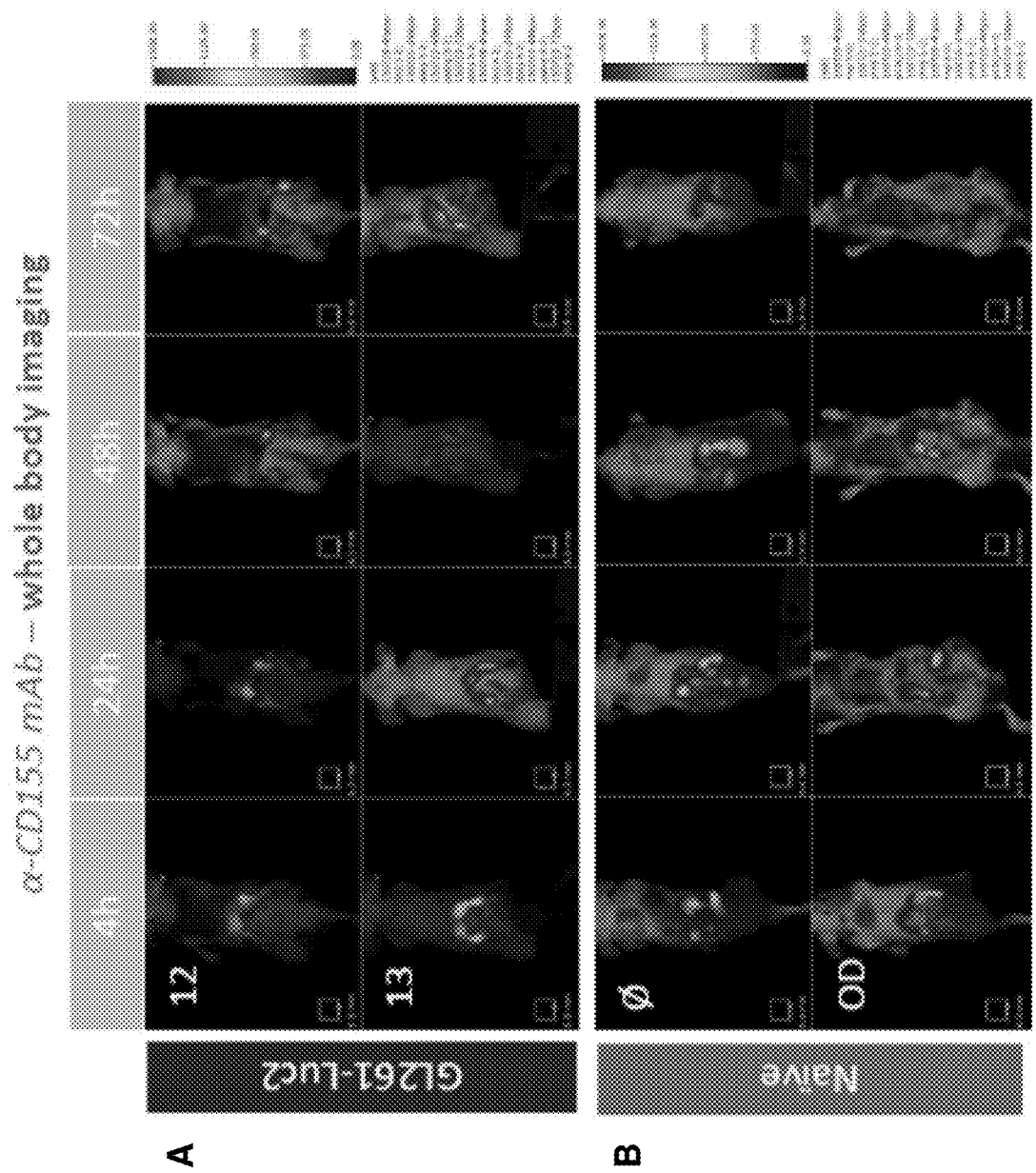

FIG. 20 depicts in vivo fluorescence whole body imaging using α-CD155 mAb in C57Bl/6 mice bearing; (A) GL261-Luc2 glioblastoma cells or (B) naïve cells at 4 h, 24 h, 48 h, and 72 h.

Figure 21:
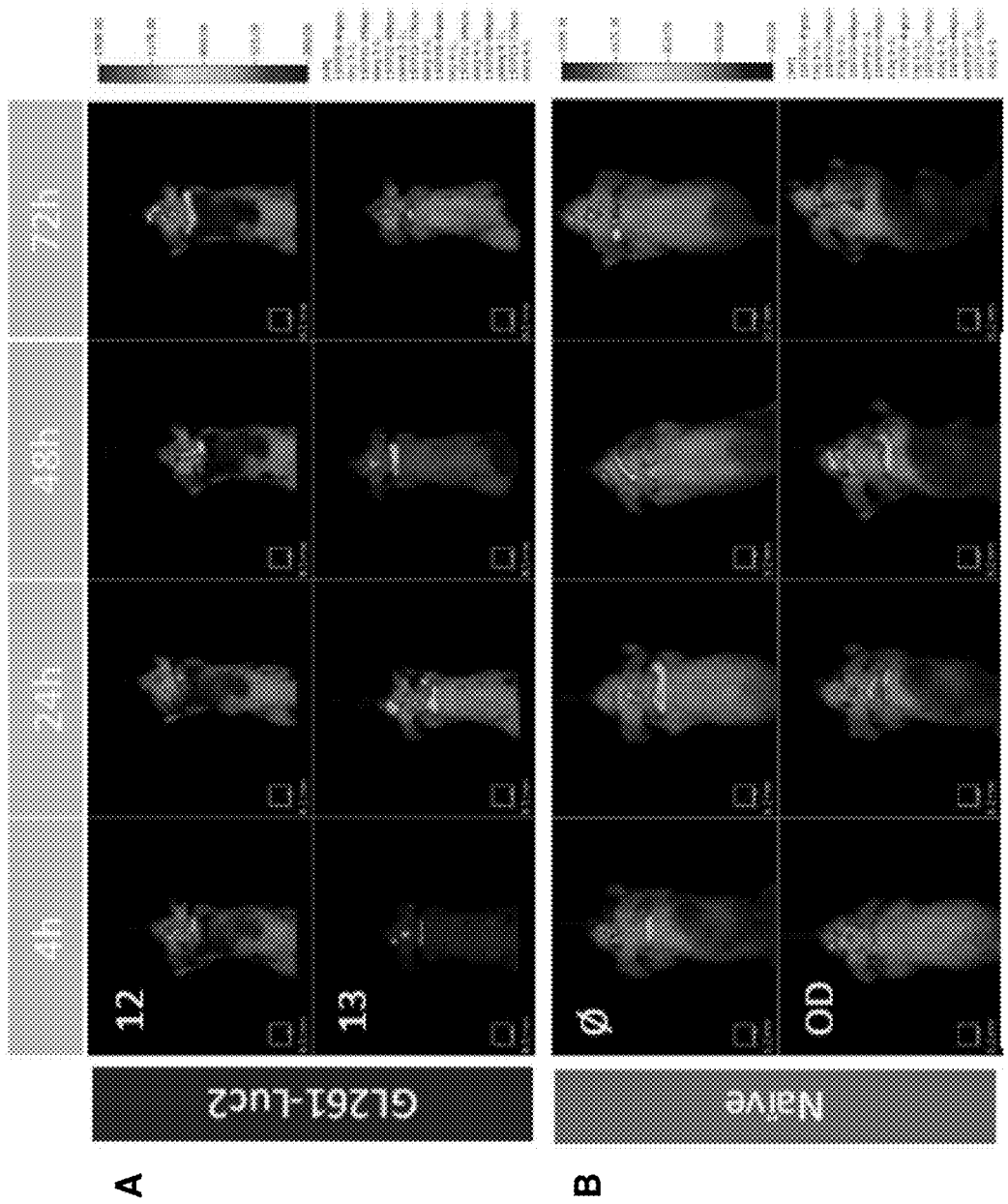
Figure 22:
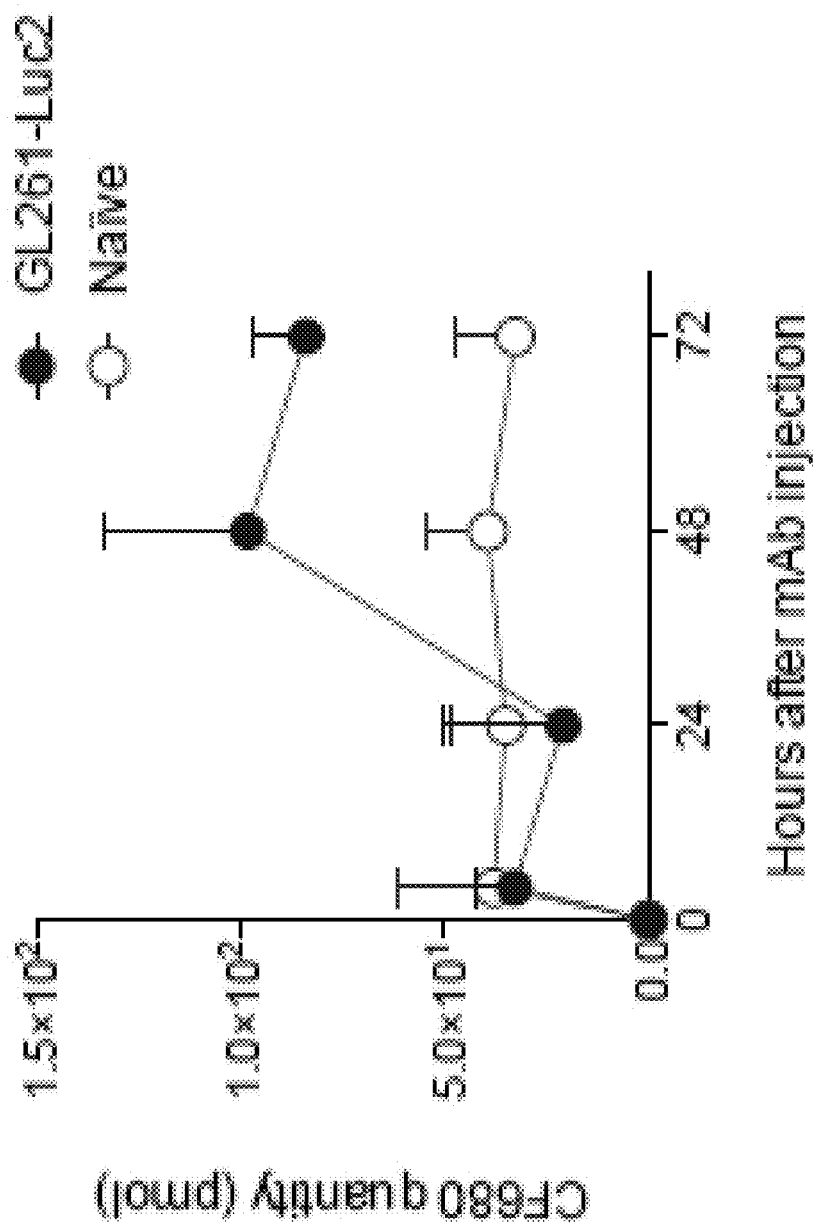

FIG. 21 depicts in vivo fluorescence head imaging using α-CD155 mAb in C57Bl/6 mice bearing (A) GL261-Luc2 glioblastoma cells or (B) naïve cells at 4 h, 24 h, 48 h, and 72 h;

FIG. 22 depicts the quantity of CF680 4 h, 24 h, 48 h, and 72 h for GL261-Luc2 and naïve cells.

Figure 23:
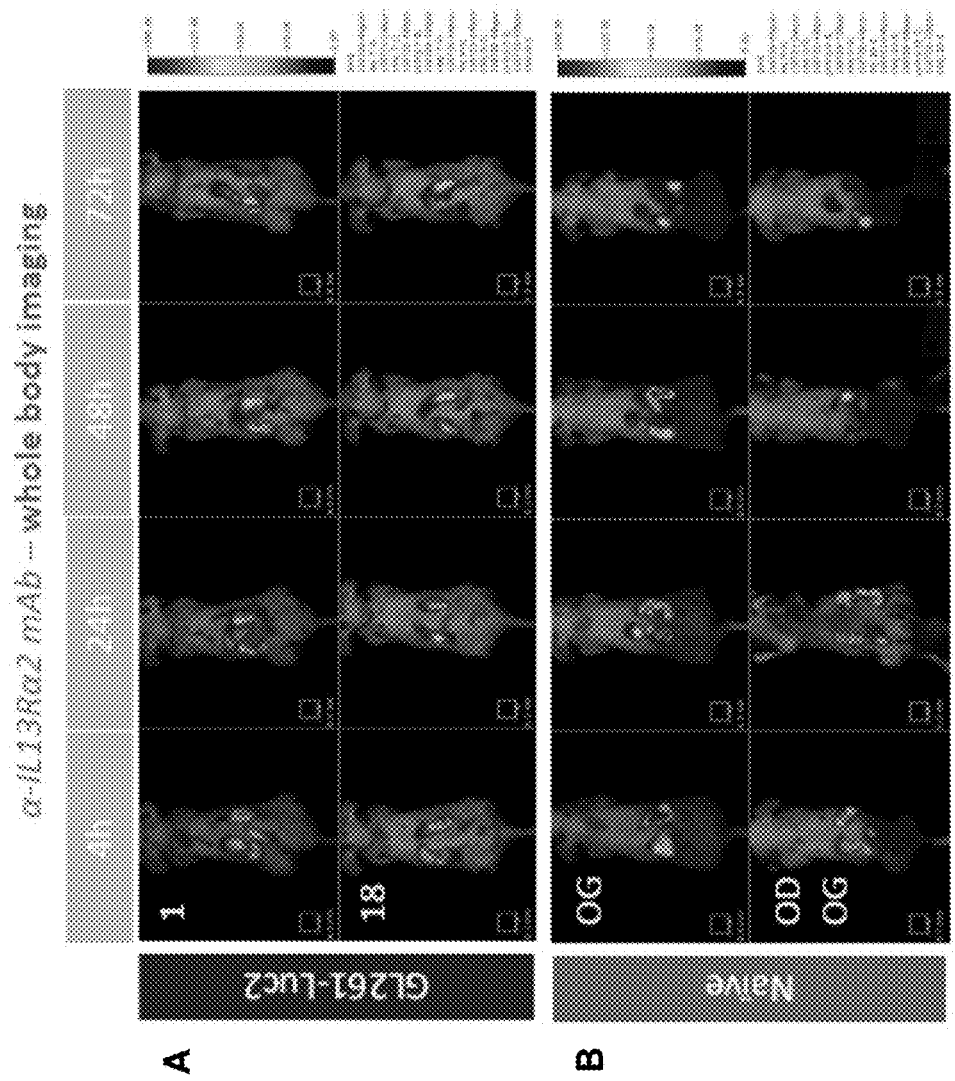

FIG. 23 depicts in vivo fluorescence whole body imaging using α-IL13Ra2 mAb in C57Bl/6 mice bearing; (A) GL261-Luc2 glioblastoma cells or (B) naïve cells at 4 h, 24 h, 48 h, and 72 h.

Figure 24:
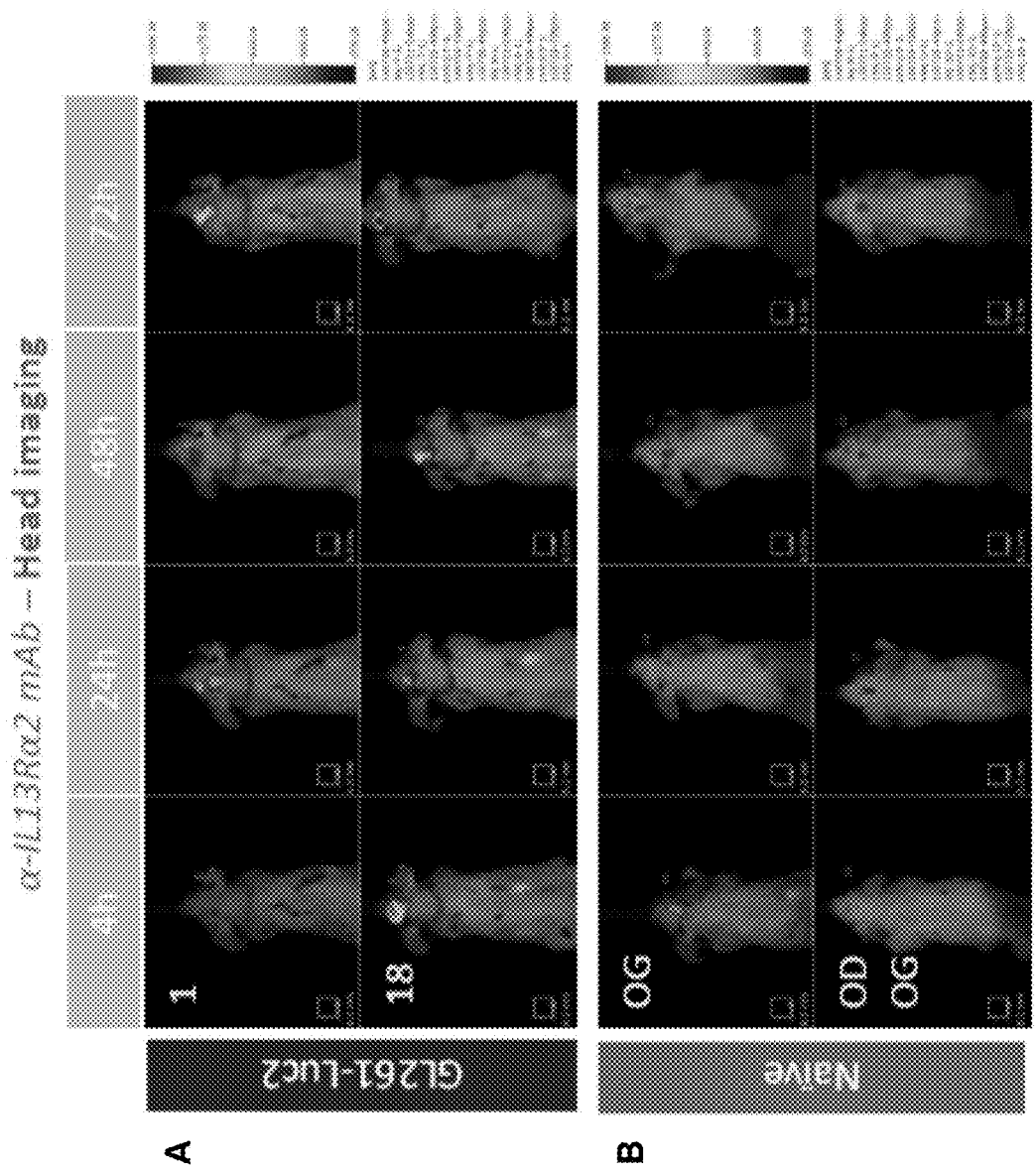
Figure 25:
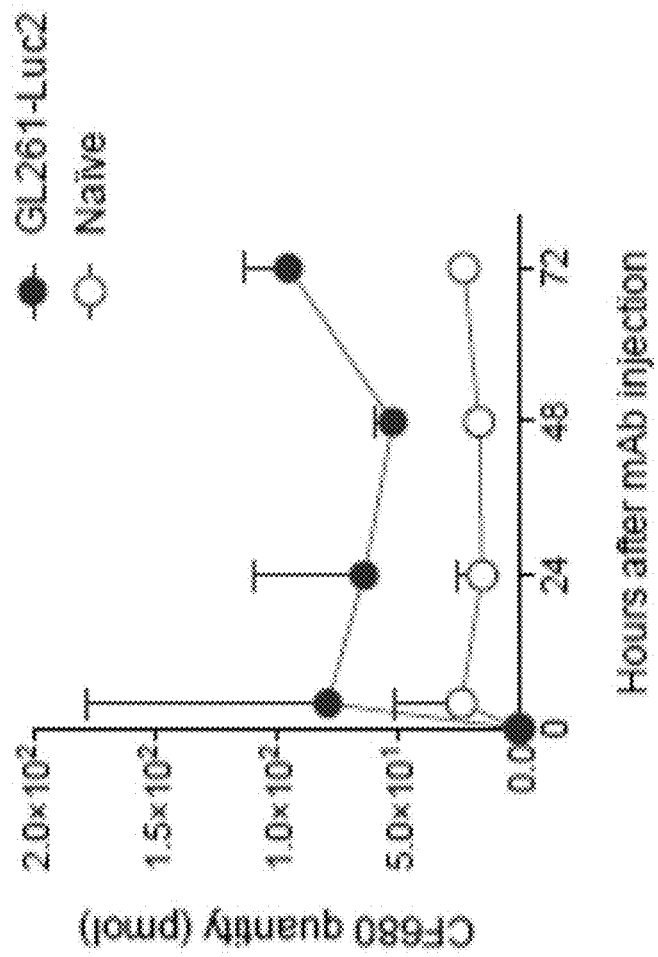

FIG. 24 depicts in vivo fluorescence head imaging using α-IL13Ra2 mAb in C57Bl/6 mice bearing (A) GL261-Luc2 glioblastoma cells or (B) naïve cells at 4 h, 24 h, 48 h, and 72 h;

FIG. 25 depicts the quantity of CF680 at 4 h, 24 h, 48 h, and 72 h for GL261-Luc2 and naïve cells.

Figure 26:
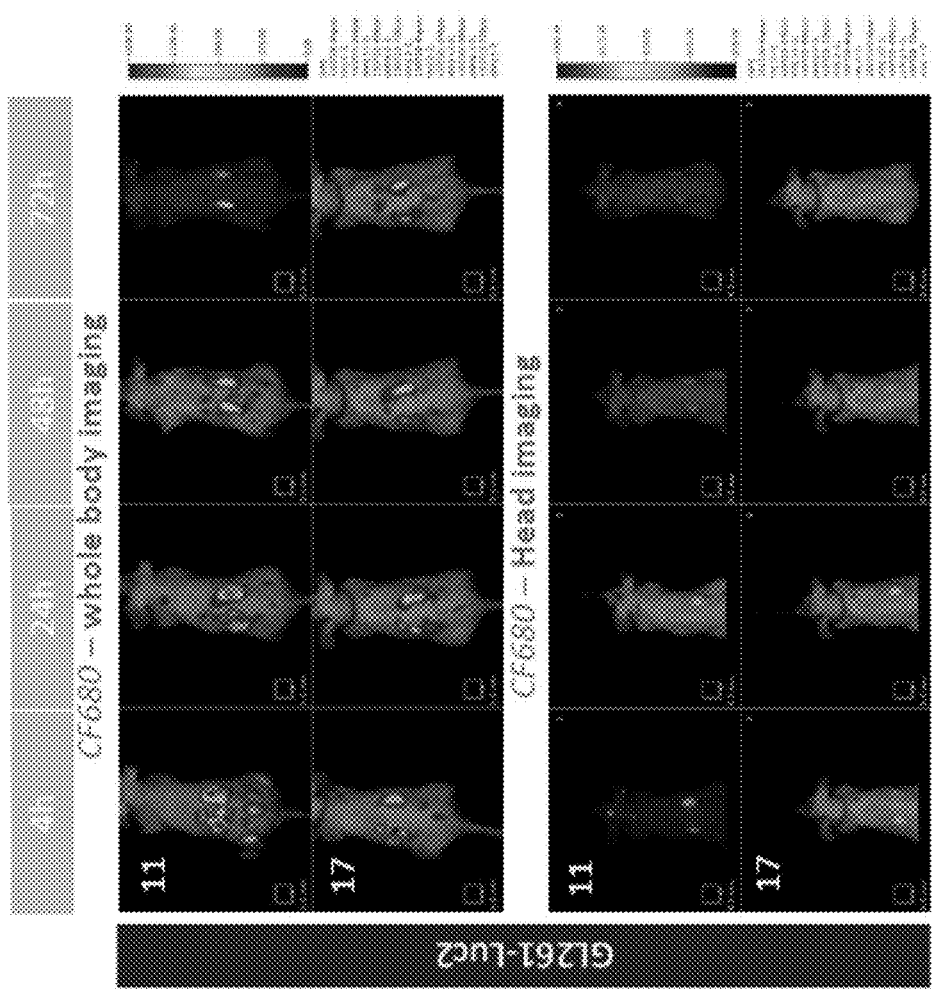

FIG. 26 depicts in vivo fluorescence whole body imaging and head imaging using CF680 in C57Bl/6 mice bearing GL261-Luc2 glioblastoma cells at 4 h, 24 h, 48 h, and 72 h.

Figure 27:
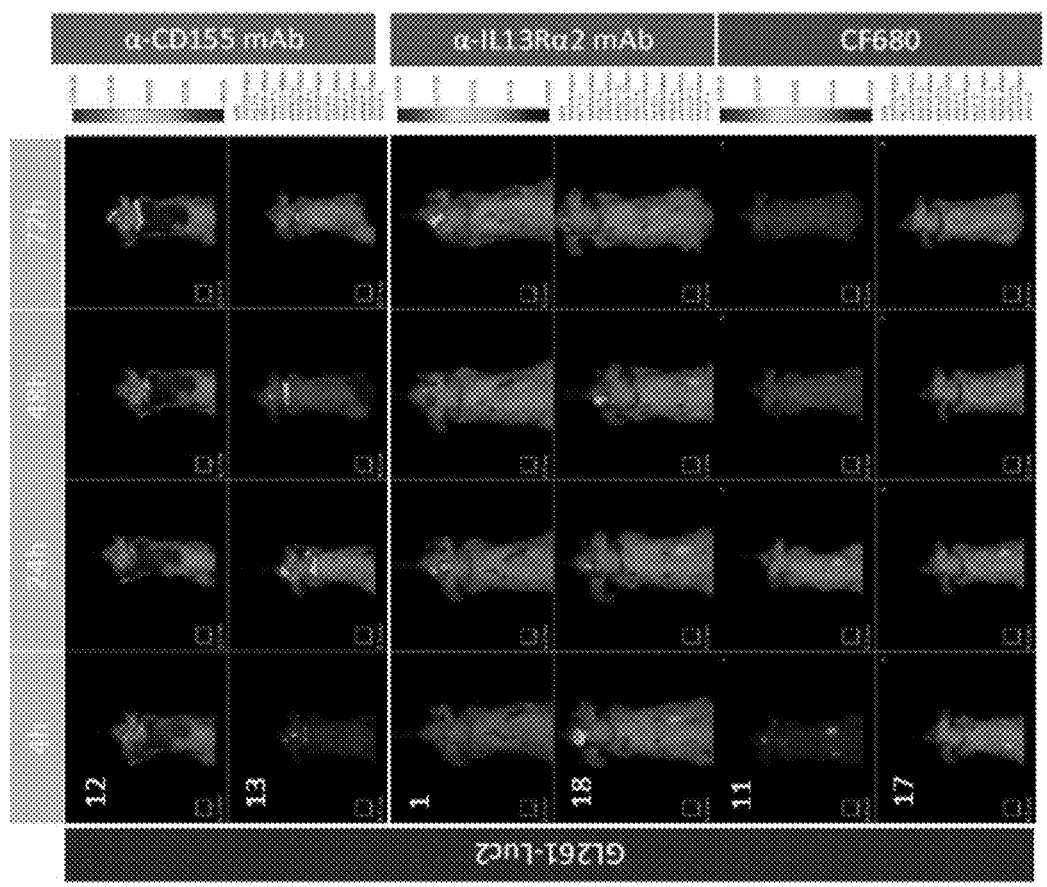

FIG. 27 depicts in vivo fluorescence imaging using α-CD155 mAb, αIL13Ra2mAb, or CF680 in C57Bl/6 mice bearing GL261-Luc2 glioblastoma cells at 4 h, 24 h, 48 h, and 72 h.

Figure 28:
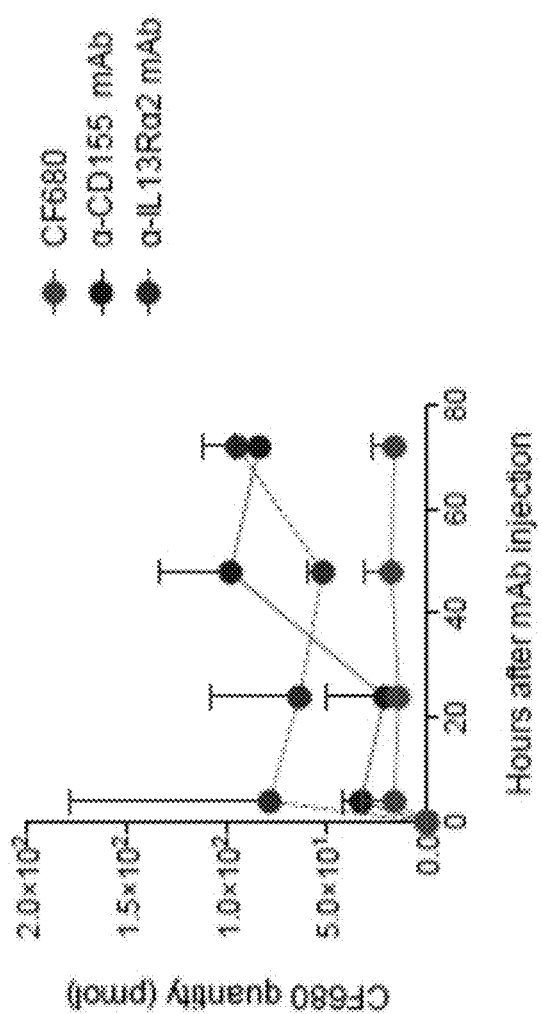

FIG. 28 depicts the quantity of CF680 at 4 h, 24 h, 48 h, and 72 h for CF680, α-CD155 mAb, and αIL13Ra2mAb.

Figure 29:
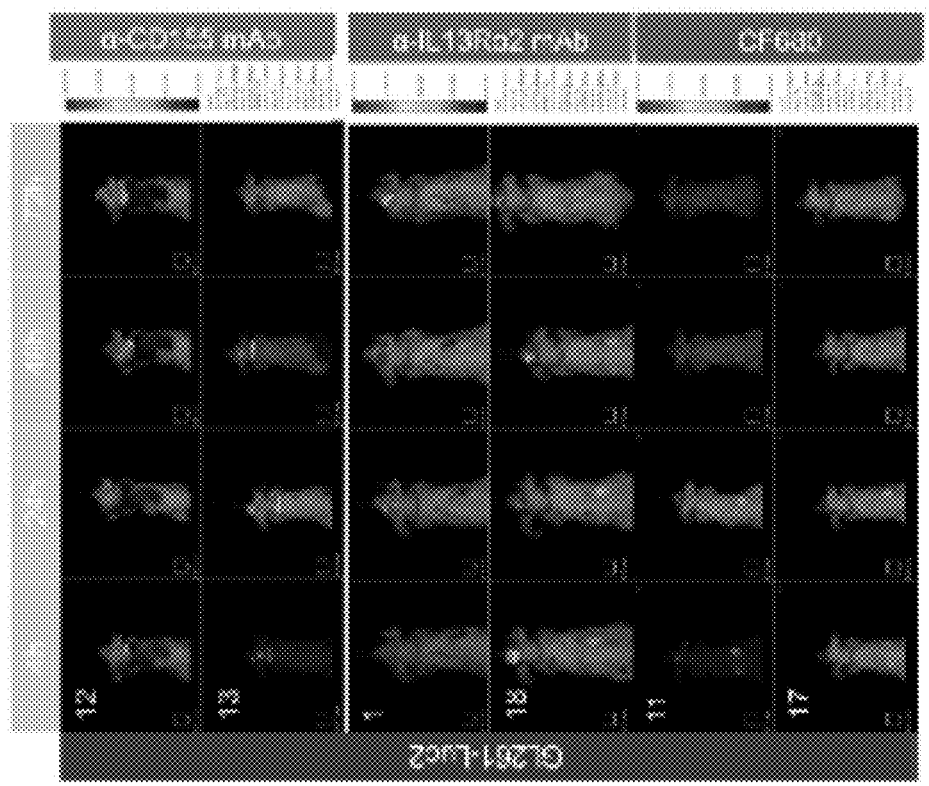

FIG. 29 depicts in vivo fluorescence imaging using α-CD155 mAb, αIL13Ra2mAb, or CF680 in C57Bl/6 mice bearing GL261-Luc2 glioblastoma cells at 4 h, 24 h, 48 h, and 72 h.

Figure 30:
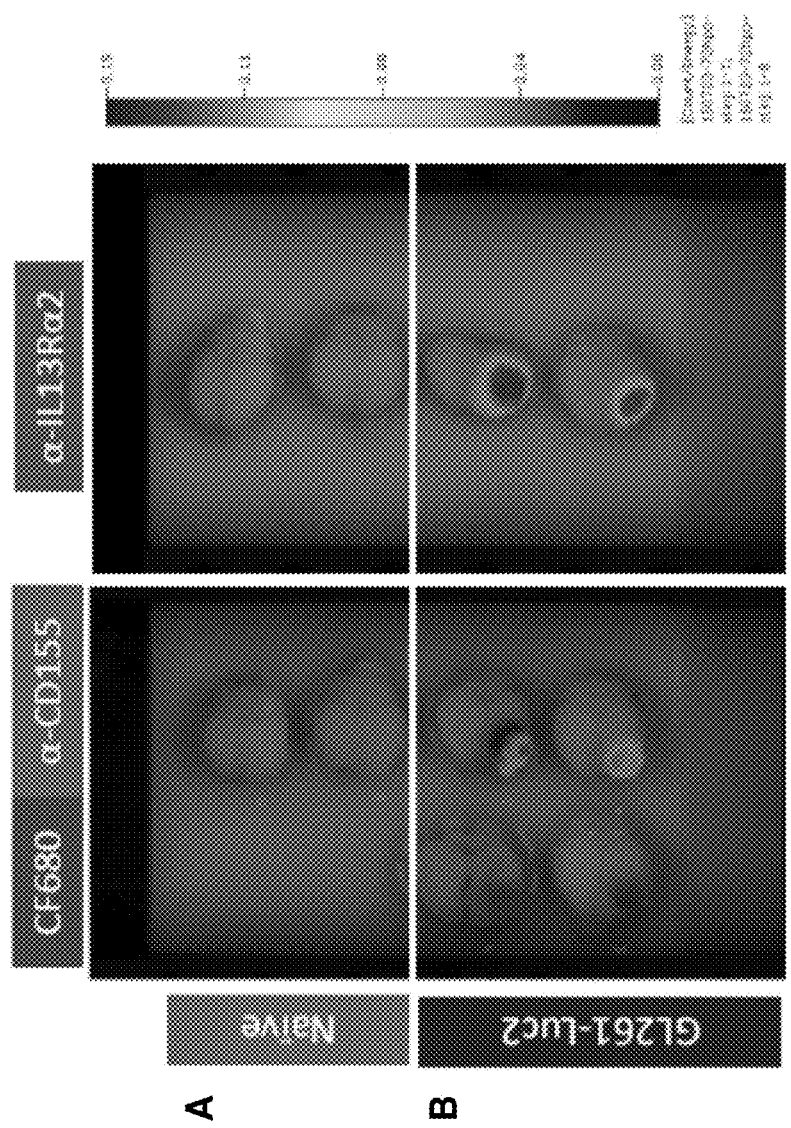

FIG. 30 depicts in vivo fluorescence imaging using CF680, α-CD155 mAb, or αIL13Ra2mAb, in C57Bl/6 mice bearing (A) GL261-Luc2 glioblastoma cells or (B) naïve cells.

Figure 31:
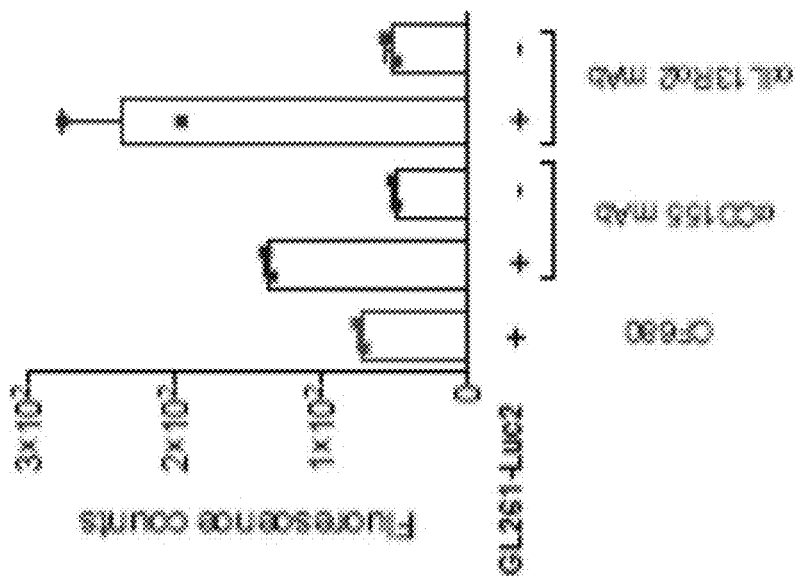

FIG. 31 depicts a bar graph of the fluorescence counts for CF680, α-CD155 mAb, or αIL13Ra2mAb in mice with or without GL261-Luc2 glioblastoma cells.

Figure 32:
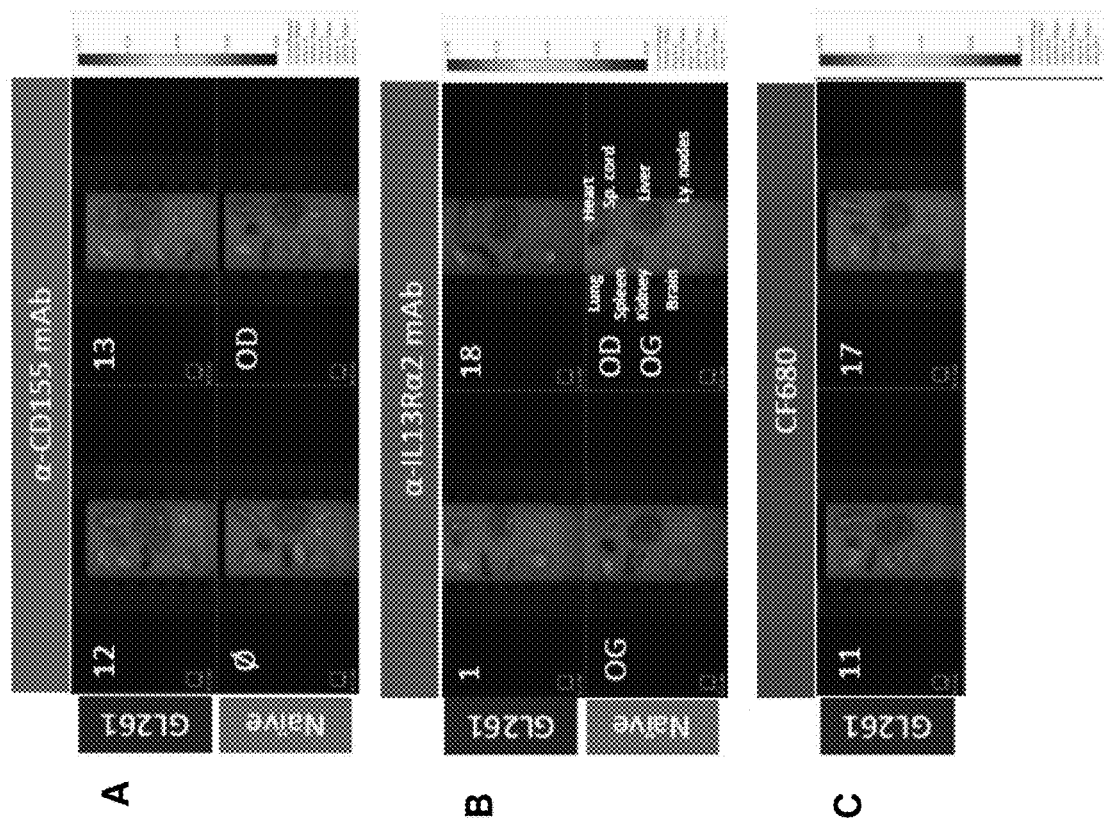

FIG. 32 depicts in vivo fluorescence imaging using (A) α-CD155 mAb, (B) αIL13Ra2mAb, or (C) CF680 in C57Bl/6 mice bearing GL261-Luc2 glioblastoma cells or naïve cells.

Figure 33:
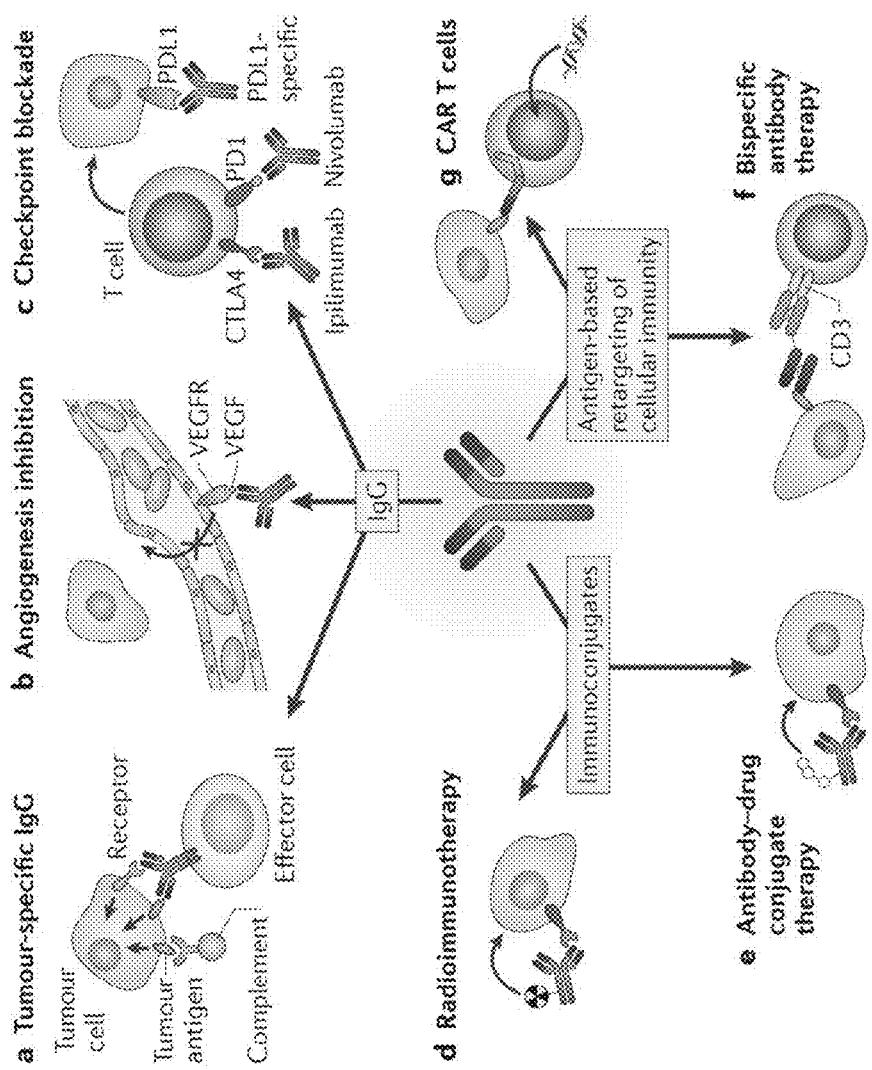

FIG. 33 depicts various embodiments of monoclonal antibody binding to target cells. Depicted are (A) tumour-specific IgG; (B) angiogenesis inhibition; (C) checkpoint blockade; (D) radioimmunotherapy; (E) antibody-drug conjugate therapy; (F) bispecific antibody therapy; and (G) CAR T cells.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

As used herein, "conjugated" refers to any manner in which the ligand is coupled to the therapeutic agent including, but not limited to, chemically, electrostatically or through the creation of fusion constructs of a ligand and therapeutic agent by employing all tools of molecular biology. The statement "all tools of molecular biology" includes but is not limited to production of custom Chimeric Antigen Receptors where an antibody or antibody fragment is incorporated into a Chimeric Antigen Receptor in CAR T cell therapy for eliminating disease, including but not limited to, cancer.

An antibody (Ab), also known as an immunoglobulin (Ig), is a large Y-shape protein produced by plasma cells that is used by the immune system to identify and neutralize foreign objects such as bacteria and viruses. The antibody recognizes a unique part of the foreign target, called an antigen. Each tip of the "Y" of an antibody contains a paratope (a structure analogous to a lock) that is specific for one particular epitope (similarly analogous to a key) on an antigen, allowing these two structures to bind together with precision.

A bispecific monoclonal antibody (BsMAb, BsAb) is an artificial protein that is composed of fragments of two different monoclonal antibodies and consequently binds to two different types of antigen. The most widely used application of this approach is in cancer immunotherapy, where BsMAbs are engineered so that it simultaneously binds to a cytotoxic cell (using a receptor like CD3) and a target like a tumor cell to be destroyed.

The blood-brain barrier (BBB) is a highly selective permeability barrier that separates the circulating blood from the brain extracellular fluid (BECF) in the central nervous system (CNS). The blood-brain barrier is formed by capillary endothelial cells, which are connected by tight junctions with an extremely high electrical resistivity of at least 0.1 $\Omega \cdot m$. The blood-brain barrier allows the passage of water, some gases, and lipid soluble molecules by passive diffusion, as well as the selective transport of molecules such as glucose and amino acids that are crucial to neural function.

Conjugated includes but is not limited to molecular, chemical, and electrostatic binding. An example of molecular binding is antibody engineering. An example of a chemical bond is a covalent bond. An example of electrostatic binding is biotin and streptavidin.

CD155 is a Type I transmembrane glycoprotein in the immunoglobulin superfamily. Commonly known as Poliovirus Receptor (PVR) due to its involvement in the cellular poliovirus infection in primates, CD155's normal cellular function is in the establishment of intercellular adherens junctions between epithelial cells. CD155 is a transmembrane protein with 3 extracellular immunoglobulin-like domains, D1-D3, where D1 is recognized by the virus. Synonyms include PVR; CD155; HVED; NECL5; Necl-5; PVS; and TAGE4.

Fusion proteins or chimeric proteins are proteins created through the joining of two or more genes that originally coded for separate proteins. Translation of this fusion gene results in a single or multiple polypeptides with functional properties derived from each of the original proteins.

The fusion proteins are being made through molecular biology techniques or chemical coupling of two antibodies or antibody fragment.

In an embodiment, the antibody has functional groups available for modification with a label, crosslinker, or covalent modification. In an embodiment, the functional group on the antibody are primary amines, sulfhydryl groups, carbohydrates, selenocysteine, or incorporation of an unnatural amino acid.

In an embodiment, a crosslinker can be used to link a gene, polypeptide, or small molecule to an antibody. In an embodiment, the crosslinker can be a heterobifunctional crosslinker. In an embodiment, the heterobifunctional crosslinker is succinimidyl acetylthioacetate (SATA), succinimidyl trans-4-(maleimidylmethyl) cyclohexane-1-carboxylate (SMCC), succinimidyl 3-(2-pyridyldithio)propionate (SPDP), 1-ethyl-3-(3-dimethylaminopropyl)carbodiimide (EDAC), N-((2-pyridyldithio)ethyl)-4-azidosalicylamide (PEAS; AET), 4-azido-2,3,5,6-tetrafluorobenzoic acid, succinimidyl ester (ATFB, SE), benzophenone-4-maleimide, benzophenone-4-isothiocyanate, 4-benzoylbenzoic acid, succinimidyl ester, iodoacetamide azide, iodoacetamide alkyne, Click-iT maleimide DIBO alkyne, azido (PEO)4 propionic acid, succinimidyl ester, alkyne, succinimidyl ester, or Click-iT succinimidyl ester DIBO alkyne.

In an embodiment, the crosslinker can be a homobifunctional crosslinker. The reactive functional groups are the same on each end. The reactive ends often target primary amines and sulfhydryl groups. In an embodiment, the homobifunctional crosslinker can be Disuccinimidyl glutarate (An amine-reactive, NHS ester-based crosslinker, 7.7 angstrom spacer arm); Glutaraldehyde solution, 70% w/w (A homobifunctional crosslinker suitable as a fixative for electron microscopy); DIDS, Disodium Salt (An anion transport inhibitor that inhibits Cl-uptake); Glutaraldehyde solution, 25% w/w (A protein cross-linking agent); Dimethyl pimelimidate dihydrochloride (A homobifunctional amine-reactive crosslinker); 3,3*-Dithiodipropionic acid di(N-hydroxysuccinimide ester) (A cleavable disulfide linkage-containing homobifunctional cross-linking reagent); Suberic acid bis(N-hydroxysuccinimide ester) (A homobifunctional amine-reactive crosslinker, 8 atom spacer arm); 3,3'-Dithiobispropionic Acid Bis-sulfosuccinimidyl Ester (A water soluble and cleavable amine-reactive crosslinker); 1,2-Ethanediyl Bismethanethiosulfonate (A homobifunctional sulfhydryl-reactive crosslinker, 4 atom spacer arm); DTME (A homobifunctional, thiol-cleavable, sulfhydryl-reactive crosslinker, 13.3 angstrom spacer arm); Suberate Bis(sulfosuccinimidyl) Sodium Salt (A water soluble, amine reactive, homobifunctional crosslinker); p-Phenylene diisothiocyanate; 1,3-Propanediyl Bismethanethiosulfonate (A sulfhydryl cross-linking reagent); 1,4-Butanediyl Bismethanethiosulfonate (A sulfhydryl cross-linking reagent); 1,6-Hexanediyl Bismethanethiosulfonate (A homobifunctional sulfhydryl-reactive crosslinker); Adipic acid dihydrazide; 1,4-Phenylene-bis-maleimide (A short, sulfhydryl reactive, homobifunctional crosslinking reagent); N,N'-Ethylenebis(iodoacetamide) (A homobifunctional sulfhydryl-reactive crosslinker); 1,2-Phenylene-bis-maleimide (A short, sulfhydryl reactive homobifunctional crosslinking reagent in protein crosslinking); N-Succinimidoxycarbonyl-β-alanine N-Succinimidyl Ester (A short amino reactive homobifunctional crosslinking reagent); 1,1-Methanediyl Bismethanethiosulfonate (A sulfhydryl cross-linking reagent); 1,5-Diazido-3-oxapentane (A multifunctional, alkylating agent); 1,4-Bis-maleimidobutane (A thiol reactive crosslinking reagent); Dimethyl 3,3'-dithiopropionimidate dihydrochloride (A thiol-cleavable, homobifunctional amine-reactive crosslinker, 8-atom spacer arm); Disuccinimidyl L-Tartrate (A homobifunctional amine-reactive crosslinker); Ethylene glycol-bis(succinic acid N-hydroxysuccinimide ester) (A homobifunctional, cleavable, amine-reactive crosslinker, 12 atom spacer arm); Bis(sulphosuccinimidyl) suberate (A crosslinking agent); 1,11-Diazido-3,6,9-trioxaundecane (An oligoether spacer and linker compound); 1,8-Bis-maleimidotetraethyleneglycol (A homobifunctional sulfhydryl-reactive crosslinker); DPDPB (A thiol-cleavable, homobifunctional sulfhydryl-reactive crosslinker); 4,4'-Diisothiocyano-2,2'-dihydrostilbenedisulfonic Acid Disodium Salt; 4,4'-Diisothiocyanatostilbene-2,2'-disulfonic acid disodium salt (A negatively charged homobifunctional cross-linking reagent and dye); 3-Maleimidopropionic Acid Hydrazonium, Trifluoroacetate; MTS-17-O5-MTS (A sulfhydryl cross-linking reagent); PEG NHS ester disulfide (n=7) (A linker molecule); 1,10-Decadiyl Bismethanethiosulfonate (A sulfhydryl cross-linking reagent); α,α'-Paraxylyl Bismethanethiosulfonate (A sulfhydryl cross-linking reagent); Ethylene-bis-maleimide (A homobifunctional sulfhydryl-reactive crosslinker); 1,11-Bismaleimidotetraethyleneglycol (A sulfhydryl reactive homobifunctional reagent); O,O*-Bis[2-(N-Succinimidyl-succinylamino)ethyl] polyethylene glycol; Bis[2-(4-azidosalicylamido)ethyl] disulfide (A homobifunctional, long chain cross-linking reagent); Bis-(2-methanethiosulfonatoethyl)dimethylammonium Chloride; Decaoxadotriacontadioic Acid Bis(N-Hydroxysuccinimide) Ester; Nonaoxanonacosanedioic Acid Bis(N-Hydroxysuccinimide) Ester; Octaoxahexacosanedioic Acid Bis(N-Hydroxysuccinimide) Ester; 1,5-Pentanediyl Bismethanethiosulfonate; 1,8-Octadiyl Bismethanethiosulfonate (A homobifunctional sulfhydryl-reactive crosslinker); 1,6-Bis-maleimidohexane (A sulfhydryl reactive maleimide based crosslinker, 16.1 angstrom spacer arm); Bis-maleimidomethyl Ether (A short sulfhydryl reactive homobifunctional crosslinking reagent); Sebacic acid bis(N-succinimidyl) ester (A reagent for crosslinking proteins and peptides); 1,11-Bis(methanesulfonyloxy)-3,6,9-trioxandecane; Bis[2-(succinimidooxycarbonyloxy)ethyl] Sulfone (A homobifunctional amine-reactive crosslinker, 13.0 angstrom spacer arm); (+/−)-trans-1,2-Bis(chloroacetamido)cyclohexane; 1,14-Diazido-3,6,9,12-tetraoxatetradecane; Heptaoxatricosanedioic Acid Bis(N-Hydroxysuccinimide) Ester; 3,6,9-Trioxaundecane-1,11-diyl-bismethanethiosulfonate; 3,6-Dioxaoctane-1,8-diyl Bismethanethiosulfonate (A homobifunctional sulfhydryl-reactive crosslinker); 3,6,9,12-Tetraoxatetradecane-1,14-diyl-bis-methanethiosulfonate; 1,6-Hexane-bis-[3-(2-pyridyldithio)propionamide]; N,N*-Bis[2-(chloroacetamido)ethyl]-N,N'-dimethylrhodamine (A homobifunctional crosslinker); and Dimethyl suberimidate dihydrochloride (A homobifunctional imidoester based crosslinker, amine reactive).

In an embodiment, azides react with alkynes via the copper-catalyzed azide-alkyne cycloaddition reaction. In an embodiment, the crosslinker reacts nonspecifically with available sites upon UV illumination. In an embodiment, the reagents contain cryptic thiols that are exposed by disulfide reduction (SPDP or PEAS) or deacetylation (SATA) and can be subsequently disulfide-coupled to other thiolated molecules or thioether-coupled to maleimides or iodoacetamides. In an embodiment, EDAC couples amines to carboxylic acids.

In an embodiment, an anti-CD155 antibody (or antibody fragment) is conjugated to a liposome containing a nucleic acid.

In an embodiment, a human or humanized antibody or antibody fragment against the human poliovirus receptor is conjugated to a fluorophore or other reporter molecule.

In an embodiment, a human or humanized antibody against the human poliovirus receptor is conjugated to a pegylated liposome encapsulating nucleic acids (RNA, DNA, chimeric, modified RNA or DNA backbone (such as phosphorothioate, 5 methylcytidine, pseudouridine), oligonucleotide, polynucleotide, plasmid and gene).

In an embodiment, a human or humanized antibody against the human poliovirus receptor is modified with a selenocysteine residue as one embodiment to facilitate stoichiometric conjugation to a reporter molecule for diagnosis of a disease or as a therapeutic for treatment.

In an embodiment, a human or humanized antibody against the human poliovirus receptor is conjugated to a therapeutic (such as small drug molecules either directly coupled or encapsulated nanoparticle) being delivered to target cells over-expressing CD155 such as tumor cells.

In an embodiment, a human or humanized antibody against the human poliovirus receptor is conjugated to a fluorophore or other reporter molecule for the non-operative, preoperative, intraoperative or postoperative diagnosis of target cells overexpressing the CD 155 receptor such as tumor cells.

In an embodiment, a human or humanized antibody against the human poliovirus receptor is fused with a therapeutic peptide either thru antibody engineering or chemical coupling.

In an embodiment, a human or humanized antibody against the human poliovirus receptor is fused with another therapeutic antibody (or antibody fragment (i.e Fab, Fab 2, cFv etc.) either chemically or thru antibody engineering in order to create bi-specific antibodies where one component is the human or humanized antibody against the human poliovirus receptor.

In an embodiment, a human or humanized antibody against the human poliovirus receptor is modified with an optimal Fc region to enhance Antibody Directed Cell Cytotoxicity against tumor cells over expressing the CD 155 receptor.

Human Antibodies are antibodies produced in human system or other mammalian systems or using yeast or phage technology. In another embodiment, the human antibody against CD155 was obtained from a human that survived the polio virus.

Humanized antibodies are antibodies from non-human species whose protein sequences have been modified to increase their similarity to antibody variants produced naturally in humans. The process of "humanization" is usually applied to monoclonal antibodies developed for administration to humans (for example, antibodies developed as anti-cancer drugs). Humanization can be necessary when the process of developing a specific antibody involves generation in a non-human immune system (such as that in mice). The protein sequences of antibodies produced in this way are partially distinct from homologous antibodies occurring naturally in humans, and are therefore potentially immunogenic when administered to human patients.

Humanizing antibodies involves removing potentially immunogenic sequences in a non-human antibody. A less immunogenic sequence for humans may be inserted in place of the immunogenic sequence. There are over a million different ways to humanize a particular antibody. In an embodiment, it may take over a year to humanize a particular non-human antibody. In an embodiment, the non-human antibody is humanized by 1) reviewing the structure to determine what sequences will be immunogenic to a human, 2) removing the sequences that will be immunogenic to a human, 3) maintaining or improving the ability of the antibody to bind to its target receptor, 4) assess the binding of the antibody to the target receptor, 5) screen for bad immunogenic responses, 6) remove the sequences responsible for the bad immunogenic response. In an embodiment, software is used to identify potentially immunogenic sequences to be removed. In an embodiment, there are still bad immunogenic responses after removing the sequences identified in the software. In an embodiment, in vitro studies are performed to determine which sequences to remove. When different parties humanize a given antibody, the sequence of the given antibody will likely be different. Each party may make different decisions when faced with the choice of which sequences to remove, to add, and to modify.

In an embodiment, the anti CD155 antibodies may be fused to an approved therapeutic antibody to get the therapeutic antibody across the blood brain barrier. In an embodiment, the approved therapeutic antibody is not able to get across the blood brain barrier alone. In such an embodiment the anti CD155 antibody that is fused to the therapeutic antibody is tasked to transcytose the construct across the blood brain barrier or other barrier that prevents entry of the therapeutic into the CNS. In an embodiment, the approved therapeutic antibody is mituxamab. In an embodiment, the mituxamab is coupled to a liposome. In an embodiment, the anti-CD155 antibody travels retrograde through nerves. In an embodiment, the anti-CD155 antibody travels retrograde through the blood-CSF barrier.

A ligand is a substance (usually a small molecule) that forms a complex with a biomolecule to serve a biological purpose. In protein-ligand binding, the ligand is usually a signal-triggering molecule, binding to a site on a target protein. In many examples described herein, the target protein to which the ligand binds is a receptor on a cell.

Non-viral means any polypeptide, including DNA/RNA segments and proteins, which lack sufficient structure to be considered a virus. Non-viral further excludes any complex polypeptide that is created through a process which begins with a virus and cleaves portions of the virus to create the polypeptide.

A polypeptide is linear chain of amino acid residues is called a polypeptide. A protein contains at least one long polypeptide. Short polypeptides, containing less than about 20-30 residues, are rarely considered to be proteins and are commonly called peptides, or sometimes oligopeptides. The individual amino acid residues are bonded together by peptide bonds and adjacent amino acid residues.

A protein is a large biological molecule, or macromolecule, consisting of one or more long chains of amino acid residues. Proteins differ from one another primarily in their sequence of amino acids, which is dictated by the nucleotide sequence of their genes, and which usually results in folding of the protein into a specific three-dimensional structure that determines its activity.

A receptor is a protein molecule usually found embedded within the plasma membrane surface of a cell that receives chemical signals from outside the cell. When such chemical signals bind to a receptor, they cause some form of cellular/tissue response, e.g. a change in the electrical activity of the cell. In this sense, a receptor is a protein molecule that recognizes and responds to endogenous chemical signals, "Therapeutically effective amounts" are amounts which eliminate or reduce the patient's tumor burden, or which prevent, delay or inhibit metastasis. The dosage will depend on many parameters, including the nature of the tumor, patient history, patient condition, the possible co-use of cytotoxic agents, and methods of administration. Methods of administration include injection (e.g. parenteral, subcutaneous, intravenous, intraperitoneal, intrathecal, convection enhanced etc.), for which the molecule or complex binding the PVR is provided in a nontoxic pharmaceutically acceptable carrier.

The delivery of an mRNA or gene for a reporter molecule EGFP was delivered to cells expressing CD155 via anti CD155 Antibody conjugated to liposomes encapsulating nucleic acids, both in mice and human cell lines using monoclonal antibodies against the respective poliovirus receptor in these cell lines. This delivery system is extendable to other nucleic acids and drugs based on the results. The anti-CD155 monoclonal antibody unexpectedly enters the central nervous system and coated the tumor. The potential applications of this finding include the utilization of CD155 to facilitate transcytosis of ligands and ligand conjugates across the blood brain barrier or other barrier preventing entry into the CNS, providing a potential alternative to the transferrin receptor. Fusion of therapeutic peptides or proteins to antibodies against CD155 or antibody fragments against CD155 may provide a pathway to cross the blood brain barrier or other barrier preventing entry into the CNS. Antibodies against CD155 bind CD155 in human and mouse cell lines and are internalized by the mouse and human cells in vitro. An antibody against the mouse CD155 receptor binds to tumor in vivo and crosses the blood brain barrier. Anti CD155 antibodies have diagnostic potential in vivo for diagnosing CD155 tumors and for demarcation of CD155 tumors preoperatively, intraoperatively and postoperatively. The CD155 antibodies may have therapeutic potential, either alone with induction of the immune system such as antibody directed cell cytotoxicity, or as Anti CD155 antibodies fused to other peptides, polypeptides or antibodies. Various cargo such as toxins, proteins, peptides, small drug molecules, RNA or DNA based drugs such as genes, messenger RNA, and oligonucleotides. Each of the above can be directly coupled to the anti CD155 antibody or the antibody against CD155 can be coupled to nanoparticles/liposomes encapsulating toxins, proteins, peptides, small drug molecules, RNA or DNA based drugs such as genes, messenger RNA, oligonucleotides. The ligand-PVR interaction such as the anti CD155 antibody-PVR may serve as transcytosis pathway for macromolecules across the blood brain barrier and may prove to be an alternative to transferrin. The Anti CD155 antibody or any ligand binding the PVR, which crosses the blood brain barrier, can also serve as transporter of drugs, proteins, peptides, polypeptides that are fused or conjugated to the anti-CD155 antibody or other PVR ligand.

Ligands that can be used in the present disclosure include but are not limited to Anti CD155 AB, CD226, DNAM1, VP, Peptides and Synthetic Antibodies (SyAms) that bind CD155, Aptamers and other Nucleic Acids that bind CD155. Also included are micromolecules and macromolecules that bind CD155 and anti CD155 Antibody Fragments all of which bind to CD155. Further included are Fusion Proteins of Ligands that bind CD155 and Fusion proteins of Antibodies that bind CD155 and Fusion proteins of Antibody Fragments that bind CD155. Still further included are Ligand Conjugates of Liposomes and Encapsulation of RNA or DNA or modified nucleic acids or other therapeutics and Ligand Conjugates of nucleic acids or other therapeutics without liposomes.

The present disclosure shows CD155 Receptor expression in Mice and Human Cell Lines, Anti CD155 (human and mouse) conjugates of Liposomes encapsulating mRNA for reporter molecule EGFP, Trafficking of AntiCD155 Conjugates of Liposomes encapsulating fluorescent-labelled RNA in mouse and human cell Lines, and Anti CD155 monoclonal antibody crosses the blood brain barrier in vivo in Mice.

Human and mice antibodies against CD155 have been shown to bind and be internalized by the respective human and mice GBM cells. In vivo, the mouse anti CD155 antibody crossed the blood brain barrier and bound to a mouse tumor implanted in the mouse's brain.

In vitro studies in mice and human GBM cell lines study delivery of messenger RNA in liposomes coupled to mice or human anti CD155 antibodies respectively. In vivo mice studies with the liposome anti-CD155 conjugates in mice with GBM. Mice with human poliovirus receptors (PVR) and human GBM tumor cells from a human gbm cell line will be treated with a human CD155 antibody coupled to a liposome that contains messenger RNA.

In an embodiment, the antibodies against CD 155, capable of crossing the blood brain barrier are selected from the group include but are not limited to antibody fragments (Fab, FcV), humanized anti-CD155 antibodies, anti-CD155 antibodies targeting coupled liposome/nanoparticle and encapsulated or unencapsulated therapeutics including toxins, genes, DNA or RNA based drugs or other therapeutics; anti CD155 antibody coupled to a fluorescent probe, or contrast agent for diagnosis of tumor or for the identification of tumor or tumor margins to assist in delineating tumor nonoperatively, preoperatively, intraoperatively or postoperatively; anti CD155 antibody can be fused to proteins peptides toxins or other antibody or antibody fragments to be delivered across the blood brain barrier utilizing CD155 for transcytosis that upon crossing, either CD155 or the fused protein or both can then bind the target cell within the CNS; unconjugated Antibody against CD155 can serve as a therapeutic if it induces Antibody Directed Cell Cytotoxicity or Complement Directed CytoToxicity in CNS as well as non-CNS tumors with high CD155 expression.

AntiCD155 antibody in mice unexpectedly crossed the blood brain barrier and bound to the tumor. Antibodies do not normally cross the BBB. Poliovirus itself has other pathways for entering the CNS. In an embodiment, the antibodies are used for treatment of neurological diseases. In an embodiment, it may be beneficial to deliver a substance across the blood brain barrier when there is not a tumor. In an embodiment the neurological disease is not a brain tumor. In an embodiment, the neurological disease is includes but is not limited to Abulia; Agraphia; Alcoholism; Alexia; Alzheimer's disease; Aneurysm; *Amaurosis fugax*; Amnesia; Amyotrophic lateral sclerosis (ALS); Angelman syndrome; Aphasia; Apraxia; Arachnoiditis; Arnold-Chiari malformation; Asperger syndrome; Ataxia; Ataxia-telangiectasia; Attention deficit hyperactivity disorder; Auditory processing disorder; Autism spectrum; Bipolar disorder; Bell's palsy; Brachial plexus injury; Brain damage; Brain injury; Brain tumor; Canavan disease; Capgras delusion; Carpal tunnel syndrome; Causalgia; Central pain syndrome; Central pontine myelinolysis; Centronuclear myopathy; Cephalic disorder; Cerebral aneurysm; Cerebral arteriosclerosis; Cerebral atrophy; Cerebral autosomal dominant arteriopathy with subcortical infarcts and leukoencephalopathy (CADASIL); Cerebral gigantism; Cerebral palsy; Cerebral vasculitis; Cervical spinal stenosis; Charcot-Marie-Tooth disease; Chiari malformation; Chorea; Chronic fatigue syndrome; Chronic inflammatory demyelinating polyneuropathy (CIDP); Chronic pain; Coffin-Lowry syndrome; Coma; Complex regional pain syndrome; Compression neuropathy; Congenital facial diplegia; Corticobasal degeneration; Cranial arteritis; Craniosynostosis; Creutzfeldt-Jakob disease; Cumulative trauma disorders; Cushing's syndrome; Cyclothymic disorder; Cytomegalic inclusion body disease (CIBD); Cytomegalovirus Infection; Dandy-Walker syndrome; Dawson disease; De Morsier's syndrome; Dejerine-Klumpke palsy; Dejerine-Sottas disease; Delayed sleep phase syndrome; Dementia; Dermatomyositis; Developmental coordination disorder; Diabetic neuropathy; Diffuse sclerosis; Diplopia; Down syndrome; Dravet syndrome; Duchenne muscular dystrophy; Dysarthria; Dysautonomia; Dyscalculia; Dysgraphia; Dyskinesia; Dyslexia; Dystonia; Empty sella syndrome; Encephalitis; Encephalocele; Encephalotrigeminal angiomatosis; Encopresis; Enuresis; Epilepsy; Erb's palsy; Erythromelalgia; Essential tremor; Exploding head syndrome; Fabry's disease; Fahr's syndrome; Fainting; Familial spastic paralysis; Febrile seizures; Fisher syndrome; Friedreich's ataxia; Fibromyalgia; Foville's syndrome; Fetal alcohol syndrome; Fragile X syndrome; Fragile X-associated tremor/ataxia syndrome (FXTAS); Gaucher's disease; Gerstmann's syndrome; Giant cell arteritis; Giant cell inclusion disease; Globoid Cell Leukodystrophy; Gray matter heterotopia; Guillain-Barré syndrome; Generalized anxiety disorder; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; Hirschsprung's disease; Holmes-Adie syndrome; Holoprosencephaly; Huntington's disease; Hydranencephaly; Hydrocephalus; Hypercortisolism; Hypoxia; Immune-Mediated encephalomyelitis; Inclusion body myositis; Incontinentia pigmenti; Infantile Refsum disease; Infantile spasms; Inflammatory myopathy; Intracranial cyst; Intracranial hypertension; Isodicentric 15; Joubert syndrome; Karak syndrome; Kearns-Sayre syndrome; Kinsbourne syndrome; Kleine-Levin Syndrome; Klippel Feil syndrome; Krabbe disease; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Leukoencephalopathy with vanishing white matter; Lewy body dementia; Lissencephaly; Locked-In syndrome; Lou Gehrig's disease (See amyotrophic lateral sclerosis); Lumbar disc disease; Lumbar spinal stenosis; Lyme disease—Neurological Sequelae; Machado-Joseph disease (Spinocerebellar ataxia type 3); Macrencephaly; Macropsia; Mal de debarquement; Megalencephalic leukoencephalopathy with subcortical cysts; Megalencephaly; Melkersson-Rosenthal syndrome; Menieres disease; Meningitis; Menkes disease; Metachromatic leukodystrophy; Microcephaly; Micropsia; Migraine; Miller Fisher syndrome; Mini-stroke (transient ischemic attack); Misophonia; Mitochondrial myopathy; Mobius syndrome; Monomelic amyotrophy; Motor Neurone Disease; Motor skills disorder; Moyamoya disease; Mucopolysaccharidoses; Multi-infarct dementia; Multifocal motor neuropathy; Multiple sclerosis; Multiple system atrophy; Muscular dystrophy; Myalgic encephalomyelitis; Myasthenia gravis; Myeloclastic diffuse sclerosis; Myoclonic Encephalopathy of infants; Myoclonus; Myopathy; Myotubular myopathy; Myotonia congenital; Narcolepsy; Neuro-Behçet's disease; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Neuropathy; Neurosis; Niemann-Pick disease; Non-24-hour sleep-wake disorder; Nonverbal learning disorder; O'Sullivan-McLeod syndrome; Occipital Neuralgia; Occult Spinal Dysraphism Sequence; Ohtahara syndrome; Olivopontocerebellar atrophy; Opsoclonus myoclonus syndrome; Optic neuritis; Orthostatic Hypotension; Otosclerosis; Overuse syndrome; Palinopsia; Paresthesia; Parkinson's disease; Paramyotonia Congenita; Paraneoplastic diseases; Paroxysmal attacks; Parry-Romberg syndrome; PANDAS; Pelizaeus-Merzbacher disease; Periodic Paralyses; Peripheral neuropathy; Pervasive developmental disorders; Photic sneeze reflex; Phytanic acid storage disease; Pick's disease; Pinched nerve; Pituitary tumors; PMG; Polyneuropathy; Polio; Polymicrogyria; Polymyositis; Porencephaly; Post-Polio syndrome; Postherpetic Neuralgia (PHN); Postural Hypotension; Prader-Willi syndrome; Primary Lateral Sclerosis; Prion diseases; Progressive hemifacial atrophy; Progressive multifocal leukoencephalopathy; Progressive Supranuclear Palsy; Prosopagnosia; Pseudotumor cerebri; Quadrantanopia; Quadriplegia; Rabies; Radiculopathy; Ramsay Hunt syndrome type I; Ramsay Hunt syndrome type II; Ramsay Hunt syndrome type III; Rasmussen encephalitis; Reflex neurovascular dystrophy; Refsum disease; REM sleep behavior disorder; Repetitive stress injury; Restless legs syndrome; Retrovirus-associated myelopathy; Rett syndrome; Reye's syndrome; Rhythmic Movement Disorder; Romberg syndrome; Saint Vitus dance; Sandhoff disease; Schilder's disease; Schizencephaly; Sensory processing disorder; Septo-optic dysplasia; Shaken baby syndrome; Shingles; Shy-Drager syndrome; Sjogren's syndrome; Sleep apnea; Sleeping sickness; Snatiation; Sotos syndrome; Spasticity; Spina bifida; Spinal cord injury; Spinal cord tumors; Spinal muscular atrophy; Spinal and bulbar muscular atrophy; Spinocerebellar ataxia; Split-brain; Steele-Richardson-Olszewski syndrome; Stiff-person syndrome; Stroke; Sturge-Weber syndrome; Subacute sclerosing panencephalitis; Subcortical arteriosclerotic encephalopathy; Superficial siderosis; Sydenham's chorea; Syncope; Synesthesia; Syringomyelia; Tarsal tunnel syndrome; Tardive dyskinesia; Tardive dysphrenia; Tarlov cyst; Tay-Sachs disease; Temporal arteritis; Tetanus; Tethered spinal cord syndrome; Thomsen disease; Thoracic outlet syndrome; Tic Douloureux; Todd's paralysis; Tourette syndrome; Toxic encephalopathy; Transient ischemic attack; Transmissible spongiform encephalopathies; Transverse myelitis; Traumatic brain injury; Tremor; Trigeminal neuralgia; Tropical spastic paraparesis; Trypanosomiasis; Tuberous sclerosis; Unverricht-Lundborg disease; Uncinate epilepsy; Von Hippel-Lindau disease (VHL); Viliuisk Encephalomyelitis (VE); Wallenberg's syndrome; West syndrome; Whiplash; Williams syndrome; Wilson's disease; and Zellweger syndrome.

TABLE 1

Monoclonal Antibody Therapies

| Drug (Trade Name) | Target | Mechanism of Action | Conditions | Source |
|---|---|---|---|---|
| Alemtuzumab (Campath) | CD52 | Depletes T and B cells via an unknown mechanism | Multiple sclerosis | Paolillo et al 1999 Coles and CAMMS223 Group 2007 |
| Daclizumab (Zenapax) | IL-2 receptor | Blocks IL-2 receptor α chain | Multiple sclerosis | Rose et al, 2004 Bielekova and Richert, 2004 |
| Infliximab (Remicade), etanercept (Enbrel) | TNF TNF-R | Inhibits TNF-α activity | Dermatomyositis, polymyositis | Efthimiou et al., 2006 |
| Natalizumab (Tysabri) | α4 β1 Integrin | Blocks entry of T cells into the CNS | Multiple sclerosis | Polman et al, 2006 Miller et al, 2007 |

TABLE 1-continued

Monoclonal Antibody Therapies

| Drug (Trade Name) | Target | Mechanism of Action | Conditions | Source |
|---|---|---|---|---|
| Rituximab (Rituxan) | CD20 | Induces cell lysis and reduces the total B-cell count | NMO, Multiple sclerosis, immune neuropathies, dermatomyositis, MMN | Cree et al, 2006 Hauser et al., 2007 Gorson et al, 2007 Levine, 2005 Dinh et al., 2007 Ruegg et al., 2004 |

Abbreviations: CNS (central nervous system); IL-2 (interleukin-2); MMN (multifocal motor neuropathy); NMO (neuromyelitis optica); TNF (tumor necrosis factor); TNF-R (TNF receptor). Arch Neurol. (2008) 65(9): 1162-65.

TABLE 2

Approved Monoclonal Antibodies for Cancer

| Antibody | FDA-approved indication | Mechanisms of Action |
|---|---|---|
| Trastuzumab: humanized IgG1 | ERBB2-positive breast cancer; ERBB2-positve gastric or gastro-oesophageal junction carcinoma | Inhibition of ERBB2 signalling and ADCC |
| Bevacizumab: humanized IgG1 | Metatstatic colon cancer; treatment of advanced NSCLC; glioblastoma; metastatic kidney cancer | Inhibition of VEGF signalling |
| Cetuximab: chimeric human-murine IgG1 | SCCHN; metastatic EGFR-positive colorectal cancer | Inhibition of EGFR signalling and ADCC |
| Panitumumab: human IgG2 | EGFR-expressing, metatstatic colorectal carcinoma | Inhibition of EGFR signalling |
| Ipilimumab: IgG1 | Unresectable or metastatic melanoma | Inhibition of CTLA4 signalling |
| Rituxumab: chimeric human-murine IgG1 | CD20-positive B cell NHL and CLL | ADCC, direct induction of apoptosis an CDC |
| Alemtuzumab: humanized IgG1 | B cell chronic lymphocytic leukaemia | Direct induction of apoptosis and CDC |
| Ofatumumab: human IgG1 | CLL | ADCC and CDC |
| Gemtuzumab ozogamicin: humanized IgG4 | CD33-positive acute myeloid leukaemia | Delivery of toxic payload, calicheamicin toxin |
| Brentuximab vedotin: chimeric IgG1 | Relapsed or refractory Hodgkin's lymphoma and systemic anaplastic lymphoma | Delivery of toxic payload auristatin toxin |
| 90Y-labelled ibritumomab tiuxetan: murine IgG1 | Relapsed or refractory, low-grade or follicular B cell NHL; previously untreated follicular NHL | Delivery of the radioisotope 90Y |
| 131I-labeled tositumomab: murine IgG2 | CD20 antigen-expressing relapsed or refractory, low-grade, follicular or transformed NHL | Delivery of the radioisotope 131I, ADCC and direct induction of apoptosis |

Abbreviations: ADCC (antibody dependent cellular cytotoxicity); CDC (complement dependent cytotoxicity)

TABLE 3

Tumor Antibody Combinations

| Brain tumor | Antibody | Target | Only on Tumor |
|---|---|---|---|
| Glioblastoma multiforme | Humanized bevacizumab | VEGF | No |
| Primary central nervous system lymphoma | Chimeric rituximab | CD20 | No |
| Breast cancer | Humanized trastuzumab | Her2 | No |

Lampson, Monoclonal antibodies in neuro-oncology, mAbs 21:26 (2011)

Antibodies are comprised of various portions including but not limited to the heavy chain, light chain, Fab, Fc, carbohydrate, variable region, and constant region.

The antibodies can be modified in ways including but not limited to glycomodification, alterations of the amino acids in the constant region, use of different human mAb isotype (e.g. IgG4), linking an isotope to mAb with a stable linker, linking a drug to the mAb with a cleavable linker, inserting DNA for mAb variable region fused to signaling peptide into T cell to induce expression of CAR, and crosslink regions from two mAbs.

mAb-based therapeutics have many functions, including but not limited to antitumor mAbs, angiogenesis inhibition, T cell checkpoint blockade, radioimmunotherapy, antibody-drug conjugate, bispecific antibody, and chimeric antigen receptor T cell.

Immune medicate effects of tumor-specific IgG include, but are not limited to, ADCC, opsonization, and CMC. Direct effects of tumor-specific IgG are to block ligands, inhibit receptor dimerization, and induce apoptotic signaling.

A potential limitation to developing monoclonal antibodies for neurooncology is the inability to cross the BBB. A monoclonal antibody targeting a brain tumor needs to first enter the central nervous system either thru the BBB (for antibodies crossing the BBB from the vascular lumen across the BBB into the brain and central nervous system), be injected directly into the tumor (convection enhanced therapy), or be directly injected intrathecally (in spinal fluid). Other mechanisms for entry into the CNS should be proposed such as retrograde thru muscle or nerves. Only after the Monoclonal antibody enters the CNS can it bind to the primary intracranial brain tumor (if the brain tumor metastasizes to the periphery, the antibody can bind the tumor without entering the CNS).

Antibodies can be produced in a humanized animal. Animals in which humanized antibodies can be generated include but are not limited to mice, rats, and rabbits. The conjugated antibody can be any commercial antibody produced in an animal.

In an embodiment, anti CD155 antibodies can be used to get a second antibody across the blood brain barrier. In an embodiment, the different antibody is humanized IgG1 targeting ERBB2 (trastuzumab); humanized IgG1 targeting VEGF (bevacizumab); chimeric human-murine IgG1 targeting EGFR (cetuximab); human IgG2 targeting EGFR (panitumumab); IgG1 targeting CTLA4 (ipilimumab); chimeric human-murine IgG1 targeting CD20 (rituximab); humanized IgG1 targeting CD52 (alemtuzumab); human IgG1 targeting CD20 (ofatumumab); humanized IgG4 targeting CD33 (gemtuzumab ozogamicin); chimeric IgG1 targeting CD30 (bentuximab vedotin); murine IgG1 targeting CD20 ($^{90}$Y-labelled ibritumomab tiuxetan); murine IgG2 targeting CD20 ($^{125}$I-labelled tositumomab); and human IgG targeting ecto-domain vimentin (pritumumab).

In an embodiment, the antibody is administered to the patient by at least one method from the group consisting of orally, intravenously, intra-arterially, intratumorally, intrathecally (CSF), intramuscularly, subcutaneously, intraperitoneally, and via convection-enhanced delivery. In an embodiment, the antibodies are anti CD155 antibodies.

In an embodiment, mRNA is able to get into the cell when it is in a liposome coupled to anti CD155.

Mouse anti CD155 antibody coupled to a fluorophore crosses the blood brain barrier and circumscribes a cell.

Anti CD 155 crosses the blood brain barrier and is internalized. The mouse blood brain barrier could be leakier than in a human or than a human tumor model. One control is the behavior of anti CD 155 in a mouse with no brain tumor. In an embodiment, mouse antibody against mouse CD155 is used in the experiments. In an embodiment, the mouse antibody is humanized.

Anti CD155 antibody D171 binds the poliovirus receptor at amino acid residues 35-50 of the poliovirus receptor.

In an embodiment, a human antibody against CD155 is coupled to a liposome containing antisense DNA or antisense RNA, or plasmid or genes with native or chemically modified residues. In another embodiment, the liposome contains mRNA with native or chemically modifies residues. The mouse antibody, human antibody or humanized against the respective CD155 receptor and the antibody-coupled liposome are capable of crossing the blood brain barrier and delivering the mRNA or antisense nucleic acid to the CD155 cells. In an embodiment, the antibody against CD155 is conjugated to IL-13. In an embodiment, human PVR is used in a mouse model during in vivo studies. In an embodiment, a lysosomal agent can be used.

The present disclosure includes aviral delivery of therapeutics including mRNA and genes via ligand conjugates where the ligand, such as a monoclonal antibody, binds to CD155/PVR leading to internalization and subsequent release of therapeutics permitting function of the drug or mRNA/gene expression (mRNA/gene).

In an embodiment, the ligand can be 1) an antibody against PVR/CD155, 2) an antibody or antibody fragment that binds the PVR/CD155 Receptor, 3) a protein that binds PVR/CD155, 4) a peptide that binds PVR/CD155, 4) a fusion protein that binds PVR/CD155, 5) a fusion protein that binds PVR/CD155 that crosses the blood brain barrier, 6) a fusion protein that binds PVR/CD155 wherein one part binds the CD155/PVR receptor and the other part is a toxin such as an antibody that binds CD155/PVR fused with a toxin such as diphtheria, 7) an aptamer (RNA or DNA or Chimeric nucleic acid with or without modifications such as phosphorothioate, 2' amino, thiouridine, pseudouridine, 5-methylCytidine or any other modification) such that the aptamer binds the CD155/PVR receptor, 8) a ligand conjugated to a peptide or protein drug or prodrug where the ligand binds the CD155/PVR receptor, 9) a ligand conjugated to a therapeutic drug or prodrug such as a nucleic acids or genes where the ligand binds the CD155/PVR receptor, or 10) a ligand conjugated a liposome that encapsulates a therapeutic drug or prodrug such as doxorubicin, siRNA, antisense DNA or other antisense molecules, messenger RNA, guide RNA for CRISPR, or naked DNA genes or plasmids.

Specific applications include, but are not limited to, use against tumors such as Glioblastoma Multiforme, Neuroblastoma, Lung Adenocarcinoma (nectin 5), Melanoma (Nectin5), Ovarian cancer, AML, Colorectal Cancer, Ewing Sarcoma, Leukemia Ganglioglioma, Oligodendroglioma, bladder carcinoma, colon carcinoma, bronchial passage, gastrointestinal, upper respiratory, genito-urinary tract, liver, prostate, brain, epidermoid carcinoma, ganglioglioma, oligodenroglioma, glioma, astrocytoma, anaplastic astrocytoma, anaplastic oligodendroglioma, malignant meningioma, bronchiocarcinoma, mammary carcinoma, colon carcinoma, parotis carcinoma, neuroectodermal tumors, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, liver metastases of epithelial adenocarcinoma, lymphangiosarcoma, lymphangioendotheliosarcoma, hepatoma, cholangiocarcinoma, synovioma, mesothelioma, Ewing's tumor, rhabdomyosarcoma, coloncarcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bileduct carcinoma, choriocarcinoma, seminoma, embryonal carcinoma, Wilms' tumor, testicular tumor, prostate, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy and light chain disease, and adenocarcinomas of the uterine cervix, uterine epithelial carcinomas, transitional cell carcinoma of the bladder, B and T cell lymphomas (nodular and diffuse) plasmacytoma, acute and chronic leukemias, soft tissue sarcomas, extracranial glioblastoma, leiomyosarcomas, malignant peripheral nerve sheath tumor, malignant fibrous histiocytoma, synovial sarcoma or any other tumor cell with high PVR expression.

Glioblastoma multiforme (GBM) often metastasizes by infiltration along white matter tracts. GBM primarily metastasizes within the central nervous system. However, it is possible for it to metastasize to other locations such as the lungs and scalp.

In an embodiment, the ligand can be used on neurons, astrocytes, regenerating muscle, and the spinal cord. Antibodies against CD155 or fragments or fusion constructs either alone or constructs have preoperative, intraoperative or postoperative diagnostic roles in identifying the full extent of tumor or extent of tumor resection.

Example: Patient with GBM Getting a Fluorescent CD155 AB Preoperatively and the Antibody Fluorescence Guides the Surgeon with Regards to Extent of Tumor Soluble CD155 can act as an antidote to anti CD155 Antibody conjugates by adding the soluble CD155 to bind the soluble antiCD155. CD155 on cells is a ligand recognized by DNAM-1 on NK cells.

Antibodies against CD155 or fragments or fusion construct either alone or conjugates have diagnostic applications to identify tumors in brain, the extent of tumors in the brain by imaging mechanisms such as PET scan, MRI, Nuclear scan, CT scan, Ultrasound, and other imaging modalities standard to the art.

Platelet endothelial cell adhesion molecule (PECAM) and CD99 receptors may also translocate antibodies across endothelial cells. Receptors such as CD155 (and PECAM and CD99) in the lateral border recycling compartment of endothelial cells may permit crossing of the blood brain barrier when antibodies are targeted against these receptors.

Mefloquine and Chloroquine increase nucleic acid release in the CNS Areas of interest include, but are not limited to, humanization of AntiCD155, Epitope mapping-Antibody binding, humanized antibody CD155 for cancer, crossing of the BBB, fusion proteins with anti CD155 antibody for transcytosis, crossing of the BBB with later membrane recycling compartment, humanized antibodies against CD155 generated in humanized transgenic mice stimulate with CD155 receptor, anti CD155 antibody combined with nimotuzumab or cetuximab (monoclonal antibodies against EGFR), anti CD155 antibody combined with avastin (VEGF), anti CD155 antibody combined with Trastuzumab (Her2), anti CD155 antibody combined with an antibody against any brain tumor receptor, and an anti CD155 antibody combined with Antibody against NK cell receptor or T cell Receptor.

EXAMPLES

Example 1

Humanization of Anti CD155 Antibody

D171 is known to cross the blood brain barrier. A software program was used to determine how to humanize mouse D171. The D171 antibody was humanized by removing potentially immunogenic sequences in the mouse D171 antibody. A less immunogenic sequence for humans was inserted in place of the immunogenic sequence. The mouse D171 antibody sequence was reviewed to determine what sequences will be immunogenic to a human. Those sequences were removed. The ability of the antibody to bind to the PVR receptor was assessed. The binding to the PVR receptor was maintained or improved by the deletion. Bad immunogenic responses were screen for and any sequences responsible for the bad immunogenic response were removed. In an embodiment, software is used to identify potentially immunogenic sequences to be removed. There can still be bad immunogenic responses after removing the sequences identified in the software.

Example 2

CD155 Receptor Expression in Mice and Human Cell Lines

Example 3

Anti CD155 (Human and Mouse) Conjugates of Liposomes Encapsulating mRNA for Reporter Molecule EGFP A. Step 3.A: Uptake of eGFP-RNA liposomes by glioblastoma cells 1. Biological system Human U87MG glioblastoma cell line Mouse GL261 glioblastoma cell line 2. Test compounds 1. Human IL 13 conjugated to unlabeled EGFP mRNA encapsulated Liposome 2. Mouse IL 13 conjugated to unlabeled EGFP mRNA encapsulated Liposome 3. Human Anti-CD 155 Antibody conjugated to unlabeled EGFP mRNA encapsulated Liposome was not be provided.

4. Mouse Anti-CD 155 Antibody conjugated to unlabeled EGFP mRNA encapsulated Liposome was provided in very small quantities.

5. IL 13 peptide 3C conjugated to unlabeled EGFP mRNA encapsulated Liposome

6. IL 13 peptide 2S1 C conjugated to unlabeled EGFP mRNA encapsulated Liposome

7. Anti CD155-peptide conjugated to unlabeled EGFP mRNA encapsulated Liposome

8. Unconjugated Liposome encapsulating unlabeled EGFP mRNA

3. Assay endpoints

Mean intensity of the expression of eGFP in cells.

Experiment 1

U87 and GL 261 cells were plated in their standard medium condition at 3 different cellular densities according to the proliferation rate to yield about 50% confluency, 90% confluency and full confluency.

After 24 hours, cells were treated with liposomes containing RNA encoding eGFP at 10, 50, or 100 ng RNA/well, in complete growth medium containing 10% foetal Bovine Serum (FBS)

After 24 hours, cells were harvested and green fluorescence was measured using flow cytometry.

All conditions were tested in triplicates, in double, with on triplicate used for flow cytometric analysis of eGFP expression for higher sensitivity, and the other triplicate was fixed for possible further immunofluorescence analysis of cell surface expression oCD155 and IL13α receptor.

Experiment 2

U87MG and GL261 cells were plated in their standard medium condition at 20000 cells per well.

After 24 hours, cells were washed once with PBS and treated with liposomes containing RNA encoding EGFP at 10, 50, or 100 and 1000 ng RNA/well, in serum deprived growth medium.

After 4 hours, medium was changed for the complete medium and cells were father incubated for 20 Hr.

24 hours after liposome treatment cells were harvested and green fluorescence was measured using flow cytometry.

All conditions were tested in triplicates, in double, with on triplicate used for flow cytometric analysis of eGFP expression for higher sensitivity, and the other triplicate was fixed for possible further immunofluorescence analysis of cell surface expression oCD155 and IL13α receptor.

Experiment 3

U87MG and GL261 cells were plated in their standard medium condition at 20000 cells per well.

After 24 hours, cells were washed once with PBS and treated with liposomes containing RNA encoding EGFP at 10, 50, or 100 and 1000 ng RNA/well, in serum deprived growth medium.

After 4 hours, medium was changed for the complete medium and cells were father incubated for 44 Hr.

48 hours after liposome treatment cells were harvested and green fluorescence was measured using flow cytometry.

All conditions were tested in triplicates.

Step 3.B. Uptake of fluorescein-RNA liposomes by glioblastoma cells

1. Biological System

Human U87MG glioblastoma cell line

Mouse GL261 glioblastoma cell line

2. Test Compounds

1. Human IL 13 conjugated to fluorescein-mRNA encapsulated Liposome

2. Mouse IL 13 conjugated to fluorescein-mRNA encapsulated Liposome

3. Human Anti-CD 155 Antibody conjugated to fluorescein-mRNA encapsulated Liposome was provided in small quantities.

4. Mouse Anti-CD 155 Antibody conjugated to fluorescein-mRNA encapsulated Liposome was provided in small quantities.

5. IL 13 peptide 3C conjugated to fluorescein-mRNA encapsulated Liposome

6. IL 13 peptide 2S1 C conjugated to fluorescein-mRNA encapsulated Liposome

7. Anti CD155-peptide conjugated to fluorescein-mRNA encapsulated Liposome

8. Unconjugated Liposome encapsulating fluorescein-mRNA

3. Assay Endpoints

Mean intensity of fluorescein fluorescence in cells.

4. Experimental Procedure

U87MG and GL261 cells were plated in their standard medium condition at 15000 cells per well.

After 24 hours, cells were washed once with PBS and treated with liposomes containing fluorescein-RNA at 100 and 1000 ng RNA/well in serum deprived growth medium, except for anti CD155 coupled liposomes that could only be tested at 100 ng RNA/well.

Step 3.C. Uptake of fluorescein-RNA liposomes by glioblastoma cells

1. Biological System

Human U87MG glioblastoma cell line

Mouse GL261 glioblastoma cell line

2. Test Compounds

1. Human IL13 conjugated to fluorescein-mRNA encapsulated Liposome

2. Mouse IL13 conjugated to fluorescein-mRNA encapsulated Liposome

3. Human Anti-CD155 Antibody conjugated to fluorescein-mRNA encapsulated Liposome was provided in small quantities.

4. Mouse Anti-CD155 Antibody conjugated to fluorescein-mRNA encapsulated Liposome was provided in small quantities.

5. IL 13 peptide 3C conjugated to fluorescein-mRNA encapsulated Liposome

6. IL 13 peptide 2S1C conjugated to fluorescein-mRNA encapsulated Liposome

7. Anti CD155-peptide conjugated to fluorescein-mRNA encapsulated Liposome

8. Unconjugated Liposome encapsulating fluorescein-mRNA

3. Assay Endpoints

Mean intensity of fluorescein fluorescence in cells.

4. Experimental Procedure

U87MG and GL261 cells were plated in their standard medium condition at 15000 cells per well.

After 24 hours, cells were washed once with PBS and treated with liposomes containing fluorescein-RNA at µg RNA/well in serum deprived growth medium, except for human and mouse antiCD155 coupled liposomes that could not be tested because of too low stock concentration. Anti-CD155 (human or mouse) and anti IL13α2R antibodies were added accordingly in each liposomal mix in medium, diluted 1/10000, 1/1000, and 1/100.

After 4 hours. cells were harvested and green fluorescence was measured using flow cytometry.

All conditions were tested in triplicates.

D. Step 3.D: Cell trafficking of liposomal content

1. Biological System

Human U87MG glioblastoma cell line

Mouse GL261 glioblastoma cell line

2. Test Compounds

1. Human IL13 conjugated to fluorescein-mRNA encapsulated Liposome

2. Mouse IL13 conjugated to fluorescein-mRNA encapsulated Liposome

3. Human Anti-CD155 Antibody conjugated to fluorescein-mRNA encapsulated Liposome was provided in small quantities.

4. Mouse Anti-CD155 Antibody conjugated to fluorescein-mRNA encapsulated Liposome was provided in small quantities.

5. IL 13 peptide 3C conjugated to fluorescein-mRNA encapsulated Liposome

6. IL 13 peptide 2S1C conjugated to fluorescein-mRNA encapsulated Liposome

7. Anti CD155-peptide conjugated to fluorescein-mRNA encapsulated Liposome

8. Unconjugated Liposome encapsulating fluorescein-mRNA

3. Assay Endpoints

Mean intensity of fluorescein fluorescence in cells.

4. Experimental Procedure

U87MG and GL261 cells were plated in their standard medium condition at 15000 cells per well. After 24 hours, cells were washed once with PBS and treated with liposomes containing fluorescein-RNA at 1 g/well in serum deprived growth medium, except for mouse anti-CD155 coupled liposomes that was not provided in necessary quantity.

30 minutes before the 6, 15 or 24 hours of treatment time points, cells were labelled with shortcake-red for lysosome detection. Live cell images were acquired of green fluorescence and red fluorescence for lysotracker detection using the BD Pathway 855® High Content Imaging platform, and cells were then fixed.

A fluorescein-specific antibody was then used for detecting fluorescein in cells. Nuclear detection was performed using Hoechst 33342. Images of the immunofluorescence labelling were acquired using the BD Pathway 855® High Content Imaging platform.

All conditions were tested in triplicates.

Results

A. Step 3.A: Uptake of eGFP-RNA Liposomes by Glioblastoma Cells

1. Experiment 1:

The uptake of functional liposomes was explored in complete medium (containing 10% serum), which is a condition closer to in vivo conditions. 10, 50 or 100 ng I well (FIGS. 2A-2F, 3A-3F) of eGFP encoding RNA in functionalized liposomes was applied on 3 densities of GL261 or U87MG cells.

Anti CD155 antibodies conjugates could only be tested at 10 ng RNA I well because a very small quantity was provided. The results show a repeated increase in cellular fluorescence after application of 10 ng RNA/well of Anti CD155 antibodies conjugated liposomes at all cellular densities tested, for the mouse (in GL261, FIG. 2A-2F) and human (in U87MG, FIG. 3A-3F) antibodies conjugates.

Among the other liposome functionalization's, none increased cellular fluorescence by eGFP expression.

Experiment 2:

Experiment 1 yielded poor or no eGFP expression after application of functionalized liposomes. A similar experiment was then conducted when liposomes were applied in a serum free medium for 4 hours and cells were then put in complete medium for survival. This strategy aimed at increasing liposome stability and interactions with cells, and higher liposome concentrations were also explored to increase efficiency. Only one cellular density was explored and treatments with 10, 50, 100, and 1000 ng of RNA in liposomes were performed.

Cytometric measurements of eGFP fluorescence in GL261 and U87MG cells showed that after 24 hours allowed for expression, a small increase of fluorescence could be measured after application of the IL-13 conjugate of liposomes, in the human version (for U87MG) or mouse version (GL261). There was a dose-dependent increase in the small number of cells with increased fluorescence 24 hours after exposure to the IL13 functionalized liposomes.

Experiment 3:

A similar experiment to experiment 2 was performed with cytometric measurements 48 h after exposure of GL261 or U87MG cells to 100 ng and 1000 ng of RNA in liposomes, to explore if increased expression time could yield higher eGFP fluorescence in cells.

This experiment confirmed results obtained in experiment 2, with a dose-dependent small increase in cellular eGFP fluorescence after application of IL-13 conjugate of liposomes. Increasing expression duration did not increase the measured effects.

B. Step 3.B: Uptake of Fluorescein-RNA Liposomes by Glioblastoma Cells

To detect functionalized eGFP RNA-containing liposome uptake, eGFP encoding RNA need to be endocyted, and RNA translated into eGFP proteins. As little or no effects were detected using eGFP encoding RNA contained in functionalized liposomes, a new uptake experiment with fluorescein labelled RNAs in liposomes was performed, aiming at measuring direct fluorescence form liposomes after cellular uptake. 100 and 1000 ng RNA in liposomes per well were applied toGL261 and U87MG cells for 4 hours except for anti-CD155 conjugated liposomes that could only be tested at 100 ng because of low quantities provided.

A small increase in the number of fluorescent cells was observed in GL261 after application of IL13 conjugated liposomes, which was not observed in U87MG at this time point. Interestingly, the 100 ng RNA/well anti CD155 conjugated liposomes exposure increased fluorescein detection in GL161 and U87MG although the antibody was different for GL261 and U87MG but shared the same target (FIG. 4A-4D). This important effect can be related with that observed for the same type of conjugate but with eGFP-RNA containing liposomes in Step 1, underlining a clear efficient functionalization in comparison with other tested functionalizations that are less or not efficient.

C. Step 3.C. Uptake of Fluorescein-RNA Liposomes by Glioblastoma Cells and Competition by IL13α2R or CD155 Antibodies.

To increase the uptake of functionalized liposomes, a new experiment was performed with a high concentration per well (3 μg) of fluorescein-RNA in liposomes and a competition assay conducted by adding anti IL13α2R antibody or anti human CD155 antibody or anti mouse CD155 antibody according to the corresponding liposome functionalization. 3antibody concentrations were tested 1/1000, 1/1000, and 1/100. Liposomes interacted with cells for 4 hours, and cellular fluorescence was measured by flow cytometry. No CD155 conjugated liposomes could be tested because of low quantities provided.

Increasing liposome concentration increased a specific liposomal uptake as shown by increased fluorescence observed with unconjugated liposomes in both cell lines, compared to control zero condition. A small increase in fluorescence with IL13 conjugated liposomes was observed in both cell lines as previously but competition with the anti IL13α2R antibody was not efficient for reducing such effect.

D. Step 3.D. Cell Trafficking of Liposomal Content

The intracellular trafficking of fluorescently labelled RNA in liposomes was explored with the aim of detecting such fluorescence in the lysosomal compartment after endocytosis. Fluorescein in lysosomes was measured after image acquisition by automated microscopy on live cells before fixation, 6, 15, or 24 hours after cell exposure to functionalized liposomes.

After 6 hours of exposition to liposomes, there was a mild increase in lysosomal fluorescence in cells treated with IL13 conjugated liposomes which disappeared at later time points. The fluorescein signal was very low and obtained at amplification levels allowing detection of signals emitted from the red lysosomal marker which contaminated the fluorescein channel.

After fixation of the cells, immunofluorescence detection of fluorescein was performed using a fluorescein antibody. Images were acquired and analyzed. After the immunofluorescence protocol, the lysosomal marker signal disappeared. Cellular fluorescence signal was quantified. No fluorescein could be further detected in any conditions and only a background signal level could be detected in each experimental condition.

IV. Conclusion

The uptake experiments with eGFP-RNA containing liposomes and fluorescein-RNA containing liposomes showed a clear superiority of anti-CD155 antibody conjugation over all other tested conjugates, and this only at the low concentrations that were allowed testing by the low quantity provided. Moreover, these results were obtained with both types of CD155 antibodies in the conjugates, human specific or mouse specific, which thus reinforces the robustness of this result.

Beside these results, only the IL-13 conjugated liposomes showed mild but repetitive uptake in the different experiments, this in the mouse version (in GL261) or human version (in U87MG). The quantity of liposomes that were tested were not too low because in the competition assay where much higher concentrations (3 g) were added, non-specific uptake was observed of non-conjugated liposomes, without increasing much that of functionalized liposomes. Suppressing the serum in the treatment medium did not improve greatly the efficiency of liposomal uptake.

Trafficking studies, on live cells by microscopy indicated a small trend to have increased fluorescein signals in lysosomes of cells treated with the IL-13 conjugated liposomes at the shortest tested duration of 6 hours observed on live cells.

The main positive result of liposome functionalization was obtained using anti-CD155 antibodies and this condition could not be explored thoroughly. Completely exploring the uptake and trafficking of CD155 antibody functionalized liposomes in vitro would be of great interest to obtain clear positive results to which other functionalization strategies could be compared later. Moreover, IL13 functionalization appeared to be mildly effective and thus, functionalization with antibodies against IL13alpha2R could appear of interest considering the effect obtained with the CD155 antibodies.

A positive control of eGFP expression after cell transfection with the same RNA that was inserted in liposomes could also be added to assess the level of expression obtained by direct transfection with known transfecting agents. This would allow knowing the dynamic range of the measure and evaluating the expression level obtained with this eGFP RNA independently of successful liposome functionalization.

RNA fluorescent labelling with fluorescein could be replaced by another more robust fluorophore which could be less sensitive to fluorophore bleaching for High Content Imaging image acquisition.

The uptake of functional liposomes was explored in complete medium (containing 10% serum), which is a condition closer to in vivo conditions. 1 0, 50 or 100 ng/well (FIGS. 2A-2F, 3A-3F) of eGFP encoding RNA in functionalized liposomes were applied on 3 densities of GL261 or U87MGcells.

Anti CD 155 antibodies conjugates could only be tested at 1 0 ng RNA/well because a very small quantity was provided. The results show a repeated increase in cellular fluorescence after application of 10 ng RNA/well of Anti CD 155 antibodies conjugated liposomes at all cellular densities tested, for the mouse (in GL261, FIG. 2A-2F) and human (in U87MG, FIG. 3A-3F) antibodies conjugates.

Among the other liposome functionalizations, none increased cellular fluorescence by eGFP expression.

FIG. 2 depicts eGFP fluorescence in GL261 cells after a 24 h exposure to 10 ng/well of eGFP encoding RNA-containing liposomes with functionalizations. 3 cellular densities were explored. (A)(B)(C): mean eGFP intensity; (D)(E)(F): gating of positive fluorescent cells.

FIG. 3 depicts eGFP fluorescence in U87MG cells after a 24 h exposure to 10 ng/well of eGFP encoding RNA-containing liposomes with functionalizations. 3 cellular densities were explored. (A)(B)(C): mean eGFP intensity; (D)(E)(F): gating of positive fluorescent cells.

FIG. 4 depicts fluorescein intensity in GL261 and U87MG cells after a 4 h exposure to 100 and 1000 ng/well of fluorescein RNA containing liposomes with functionalizations. Cells were treated 4 hours in serum free medium and subjected to flow cytometry. (A)(B): mean eGFP intensity; (C)(D): gating of positive fluorescent cells.

Example 4

Trafficking of AntiCD155 Conjugates of Liposomes encapsulating Fluorescent-labelled RNA in mouse and human cell Lines Example 5

Anti CD 155 monoclonal antibody crosses the blood brain barrier in vivo in Mice

Example 6

Fusion of therapeutic peptides or proteins to antibodies against CD155 or antibody fragments against CD155 provides a pathway to cross the blood brain barrier.

Example 7

Antibodies against CD155 receptor bind CD155 in human and mouse cell lines and are internalized by the mouse and human cells in vitro.

Example 8

Antibodies against the mouse CD155 receptor bind to tumor cells in vivo and cross the blood brain barrier.

Example 9

Conjugation of liposomes containing therapeutic peptides or proteins to antibodies against CD155 or antibody fragments against CD155 provide a pathway to cross the blood brain barrier.

Example 10

Anti CD155 antibodies have diagnostic potential in vivo for diagnosing CD155 tumors and for demarcation of CD155 tumors preoperatively, intraoperatively, and postoperatively.

Example 11

CD155 antibodies have therapeutic potential, either alone with induction of the immune system, or as Anti CD155 antibodies fused to other peptides, polypeptides or antibodies.

Example 12

Synthesis of D171 and Chimeric and Constructs Tested with ELISA and FACS with Hap 1 Cells with CD155 and CD155 Knockout
  D171 sequenced
  Selenocysteine added to Mouse IgG1 D171
  IL13 alpha2 agonist fused to Mouse IgG1 D171
  D171 Antibody Chimerized with Human IgG1
  D171 Antibody Chimerized with Human IgG1 with selenocysteine
  D171 Antibody Chimerized with Human IgG1 optimized for ADCC

Example 13

Humanization of Chimeric D171 Antibody
16 variants tested with FACS/HuProt Assay/Biocore/ELISA
Best and Worse Selected and Epitope mapping
Human IgG1 variant of Best
Selenocysteine Variant of Best
Fc Optimized for ADCC

Example 14

(C) Anti CD155 Antibodies for ADCC against Tumor Targets

In Vitro Assays in Human Tumor Cell Lines (Tumor TargetS) and Normal Tissue Cell Lines (Control) for ADCC Mouse CD155 Antibodies (Mouse IgG1 Biotechne 690912) and Mouse CD155 Antibody with Fc Optimized for ADCC in GL261

Chimeric D171(Mouse Fab and Human IgG1) and Chimeric (Mouse Fab and Human IgG1 with Fc optimized for ADCC) in Human Cell Lines and Control Humanized D171 Anti CD155 Antibodies (Humanized IgG1 Antibody and Humanized IgG1 Antibody with Fc Optimized for ADCC) in Human Cell Lines and Control In Vivo Assay for ADCC Mice with GL261 Tumors (Intracranial) Treated with Mouse CD155 Antibodies against mouse receptor (C57B16)

Human PVR Transgenic Mice and WT Mice with Intracranial GL261 Tumors (Transgenic with Human PVR) treated with Human D171 Mouse IgG AntiCD155 Antibodies Against Human Receptor (C57B16)

Hu-SCID Mice with U87 tumors (peripheral) treated with CD155 Ab modified with Human IgG Optimized for ADCC Example 15

Antibodies against the Lateral Membrane Recycling Compartment Receptors Cross the Blood Brain Barrier and Enter the Central Nervous System Example 16

Antibodies against the Lateral Membrane Recycling Compartment Receptors Cross the Blood Brain Barrier and Enter the Central Nervous System In Vivo Mice CD31(LMRC)/CD99(LMRC)/PVR (LMRC)/GFAP (control) Antibodies labeled with CF688 Dye will be assessed in a Brain Tumor Model since CD31/CD99/PVR are expressed on GBM. This will be performed in the presence and absence of Imatinib, an inhibitor of receptor mediated endocytosis at the blood brain barrier.

Anti-CD99/Anti CD31/Anti PVR antibodies will be assessed in the corresponding Model In vitro (Human, Mouse, Rat and Monkey) BBB Model. This will be performed in the presence and absence of Imatinib, an inhibitor of receptor mediated endocytosis at the blood brain barrier.

Mice Without Brain Tumors will be studied with Labeled GFAP Antibodies, alone or coupled with Anti CD99/CD31/CD155 antibodies. This will be performed in the presence and absence of Imatinib, an inhibitor of receptor mediated endocytosis at the blood brain barrier Transgenic Mice with human PVR gene and Normal (non-transgenic) Mice with human PVR transfected GL261 GBM tumor and GL261 Wild Type GBM-tumor—treated with human CD155 antibody labeled with CF688

Control PVR mice with human PVR transfected GL261 tumor treated with human CF688 labeled AntiCD155 antibody in presence and absence of Imatinib.

Normal Mice (Non-PVR mice) with human PVR transfected GL261 tumor treated with hPVR mRNA in liposomes directed to BBB. Check for human PVR expression at BBB and then treat mice with Human AntiCD155 antibody Example 17

Checking the reaction monitoring and the conjugate formation.

The following reaction was performed:
0.02 mM Pyrene Maleimide in 0.1M Sodium phosphate pH7, 1% Acetone with:
2 mM Selenocysteine (SEL)
or 2 mM Cysteine
or 2 mM β-Mercaptoethanol
or nothing for negative control.
FIG. 6
The reaction can be monitored by fluorescence (λexc=330 nm, λem=375 nm) and the conjugate formation is confirmed.

Example 18

Optimization of the reaction conditions by varying physical and chemical parameters
pH Influence
Reaction conditions
Fix parameters:
0.02 mM Pyrene Maleimide
2 mM Selenocysteine
1% Acetone
Ambient temperature
In dark
Monitoring by fluorescence (λexc=330 nm, λem=375 nm)

TABLE 4

| Variable parameter: pH | | | | |
|---|---|---|---|---|
| pH | 5 | 6 | 7 | 8 |
| Buffer | 0.1M Acetate | | 0.1M Sodium Phosphate | |

FIG. 7. The reaction between selenocysteine and pyrene maleimide is largest for pH 7.

Example 19

Optimization of the reaction conditions by varying physical and chemical parameters
Temperature Influence
Reaction conditions:
0.1 mM Pyrene Maleimide
0.5 mM Selenocysteine
1% Acetone
0.1 M Phosphate buffer pH 7
In dark, monitoring by fluorescence (λexc=330 nm, λem=375 nm)
Variable parameter: temperature (37° C. or room temperature)
FIG. 8. The fluorescence intensity after 24 h is higher for the reaction performed at 37° C. However, this temperature could have an effect on conjugate stability. This point will be checked by NMR.

Example 20

Optimization of the reaction conditions by varying physical and chemical parameters
Reagents Concentration Influence
Reaction conditions
0.1 mM Pyrene Maleimide 1% Acetone
0.1 M Phosphate buffer pH 7
Ambient temperature
In dark, monitoring by fluorescence (λexc=330 nm, λem=375 nm)
Variable parameter: selenocysteine concentration (from 0.1 to 5 mM)
FIG. 9
Reaction conditions
2 mM Pyrene Selenocysteine
1% Acetone
0.1 M Phosphate buffer pH 7
Ambient temperature
In dark, monitoring by fluorescence (λexc=330 nm, λem=375 nm)
Variable parameter: pyrene maleimide concentration (from 0.1 to 0.5 mM)
FIG. 10
In these two tests, selenocysteine is the limiting reagent: when the pyrene maleimide is fixed, the fluorescence intensity increases with selenocysteine concentration
When the selenocysteine is fixed, the fluorescence intensity reaches a plateau for pyrene maleimide concentration upper to 0.05 mM. The last results allow to estimate the reaction stoichiometry: 1 molecule of pyrene maleimide reacts with 40 molecules of selenocysteine. The stoichiometry of the reaction between selenocysteine and pyrene maleimide, and cysteine and pyrene maleimide could be compared by the following:
Reaction conditions:
2 mM Selenocysteine or 2 mM Cysteine
1% Acetone
0.1 M Phosphate buffer pH 7
Ambient temperature
In dark, monitoring by fluorescence (λexc=330 nm, λem=375 nm)
Variable parameter: pyrene maleimide concentration (from 0.1 to 0.5 mM)
FIG. 11. Contrary to selenocysteine, cysteine is not a limiting reagent in this reaction. One molecule of pyrene maleimide reacts with more than 40 molecules of cysteine.
The conjugate will be characterized by NMR Analysis Example 21

In Vitro Analysis of Uptake of Anti-Mouse CD155 Antibody conjugate and Anti-Human CD155 Antibody Conjugate of liposomes encapsulating fluorescent labeled mRNA or unlabeled mRNA for EGFP in respective Cell Lines (GL261 Mouse GBM Cell line and U87 Human GBM Cell Line Example 22

Figure 1:
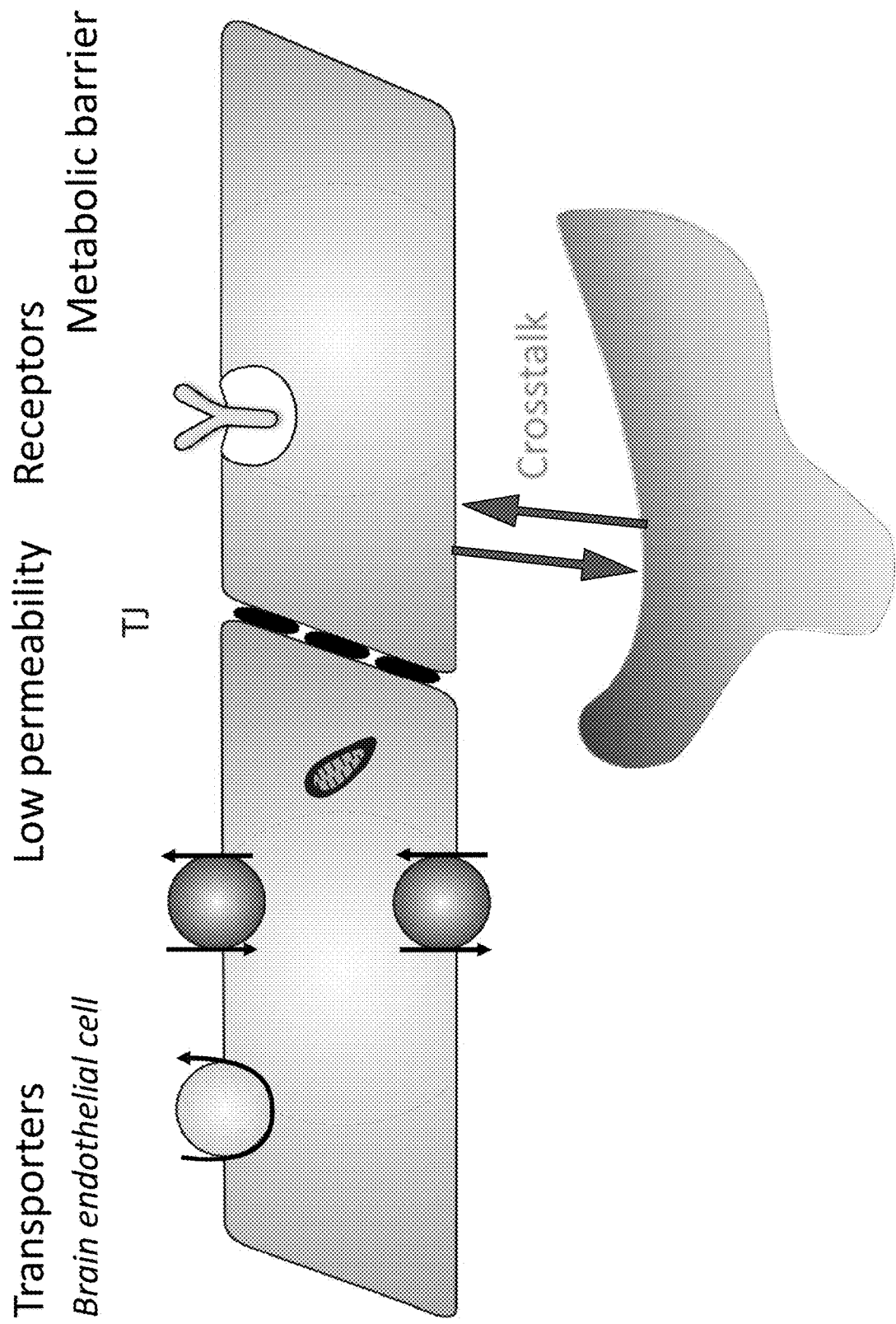
FIG. 1 depicts the blood brain barrier and receptor.
Figure 2A:
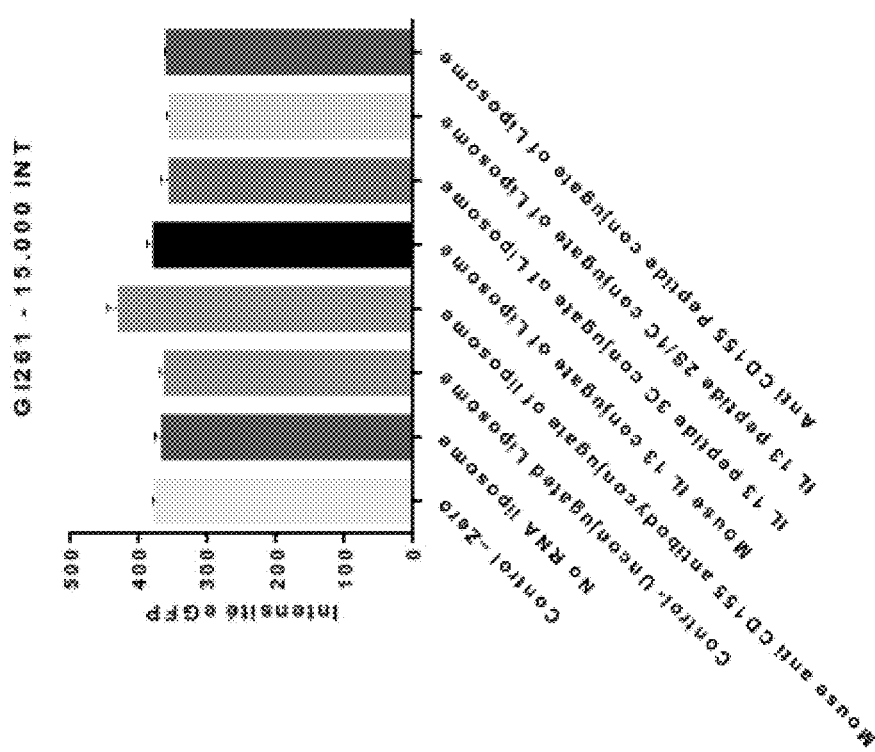
FIG. 2A-2F depicts eGFP (enhanced Green Fluorescence Protein) fluorescence in GL261 cells after a 24 h exposure to 10 ng/well of eGFP encoding RNA-containing liposomes with functionalizations. 3 cellular densities were explored. (A)(B)(C): mean eGFP intensity; (D)(E)(F): gating of positive fluorescent cells.
Figure 2B:
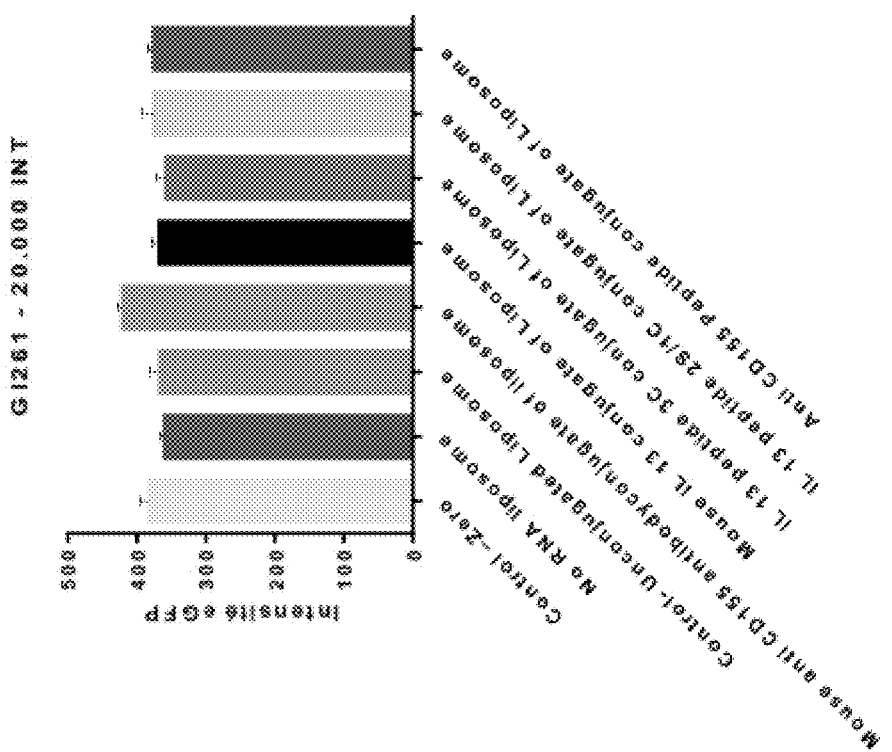
Figure 2C:
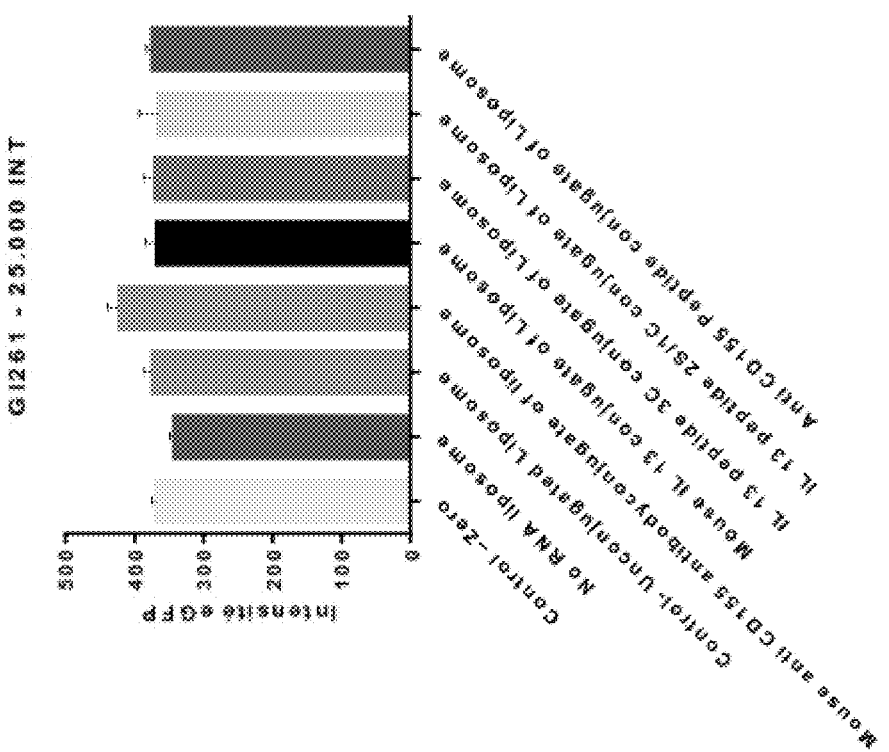
Figure 2D:
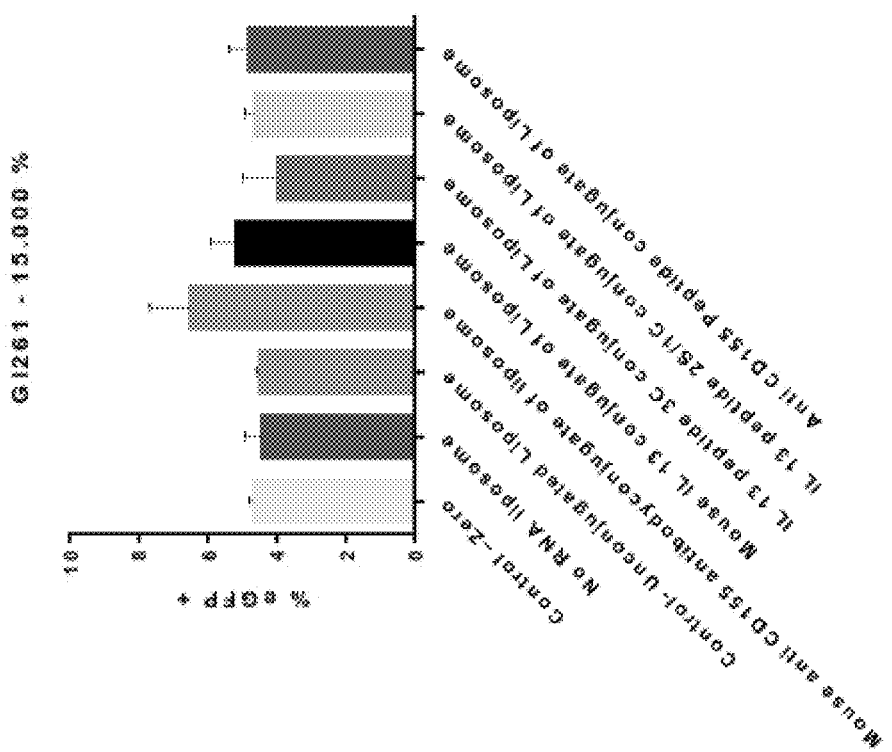
Figure 2E:
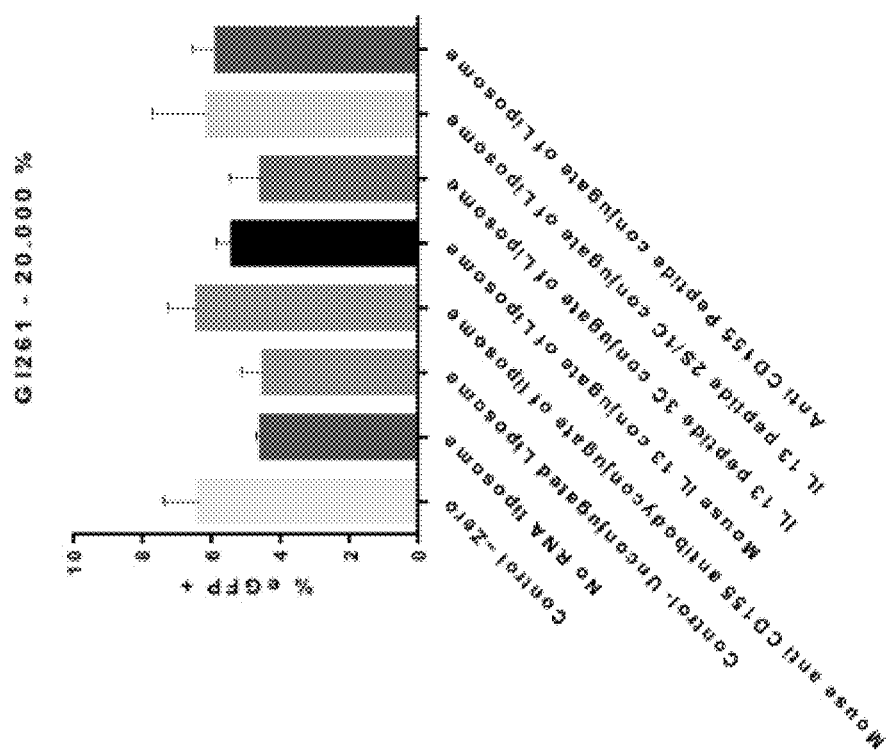
Figure 2F:
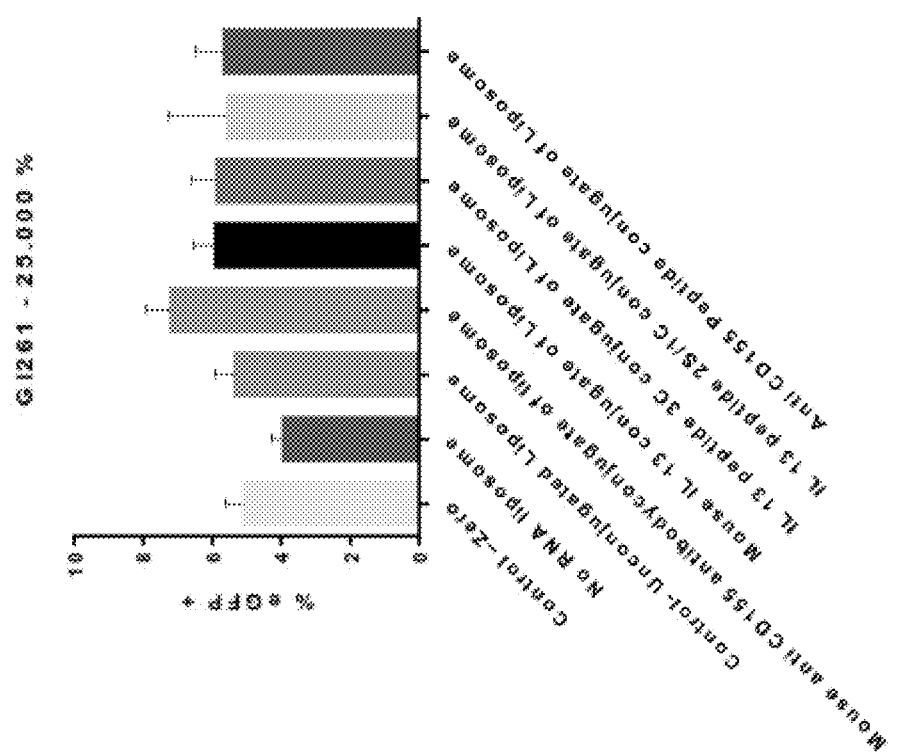
Figure 3A:
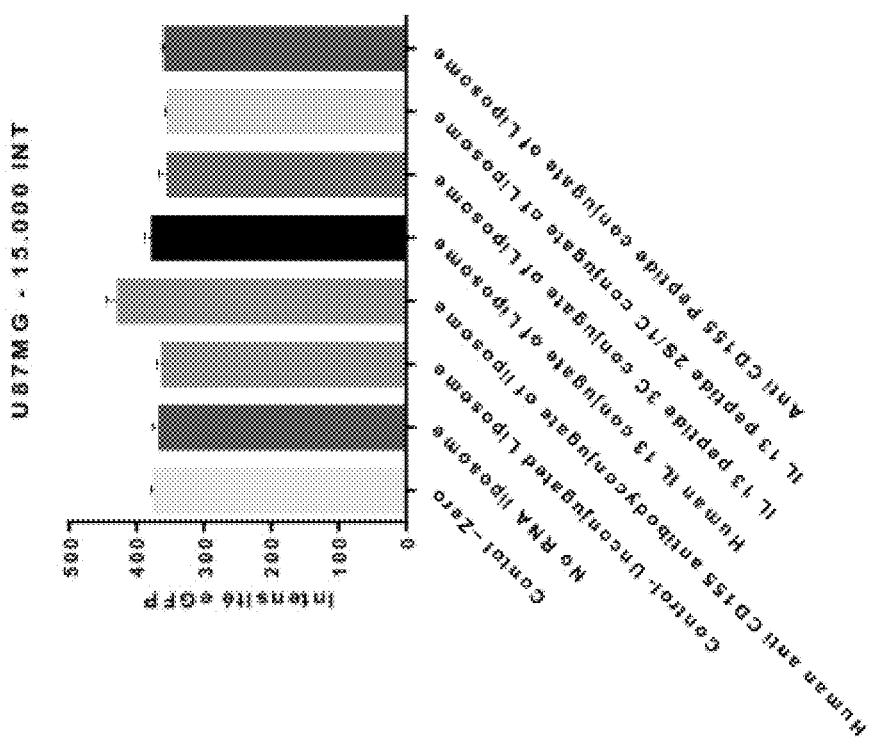
FIG. 3A-3F depicts eGFP fluorescence in U87MG cells after a 24 h exposure to 10 ng/well of eGFP encoding RNA-containing liposomes with functionalizations. 3 cellular densities were explored. (A)(B)(C): mean eGFP intensity; (D)(E)(F): gating of positive fluorescent cells.
Figure 3B:
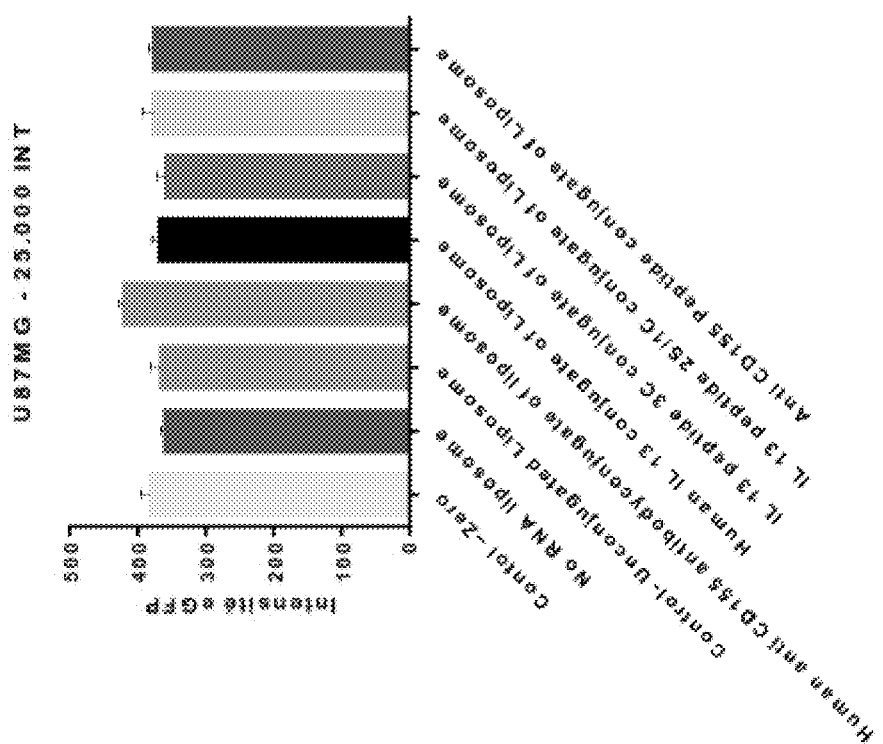
Figure 3C:
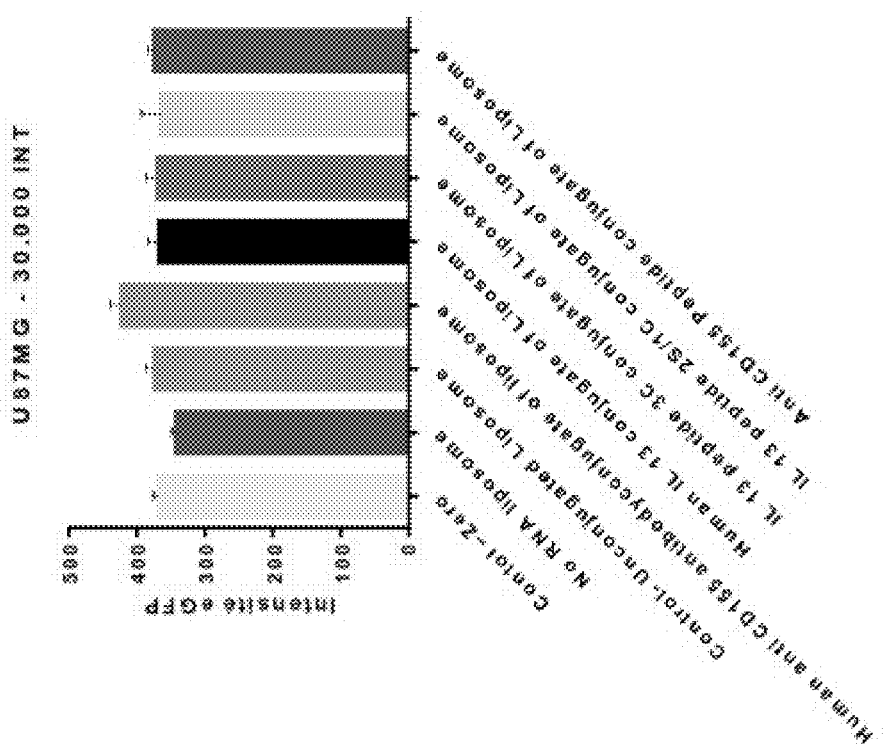
Figure 3D:
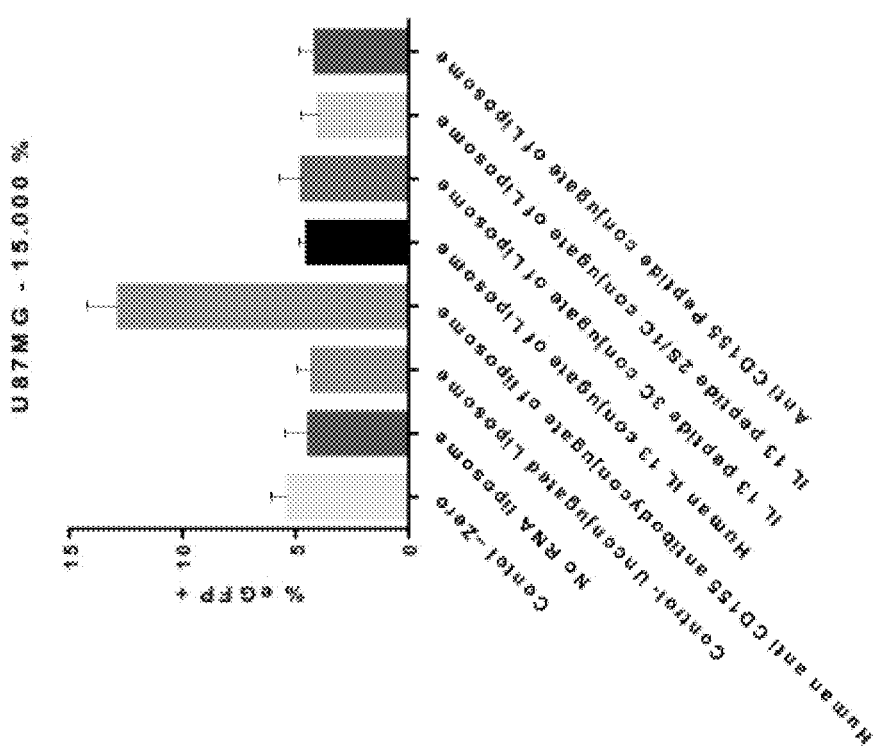
Figure 3E:
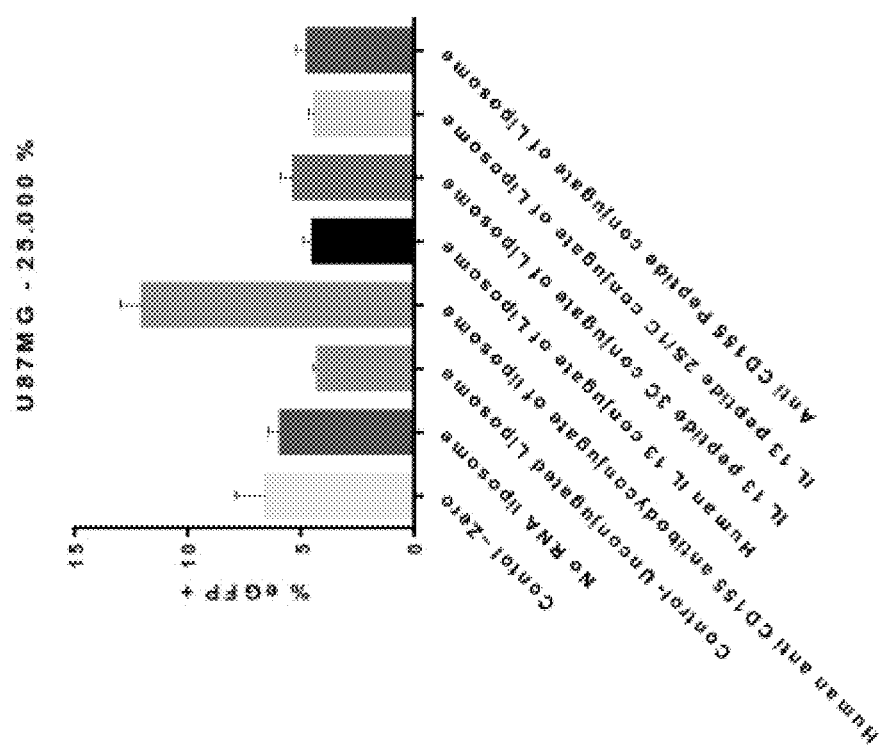
Figure 3F:
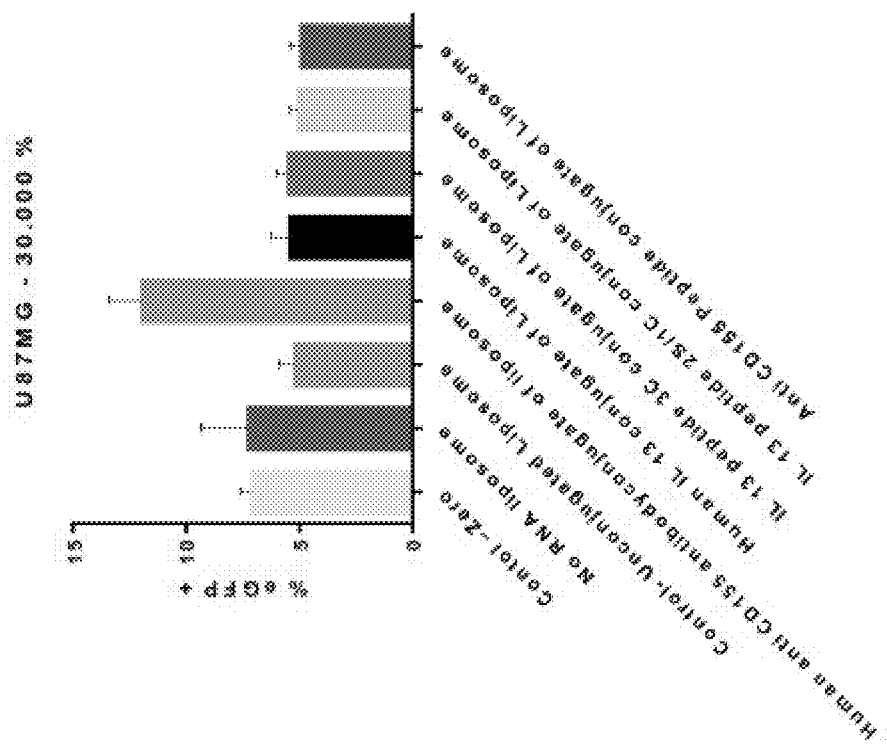
Figure 4A:
FIG. 4A-4D depicts fluorescein intensity in GL261 and U87MG cells after a 4 h exposure to 100 and 1000 ng/well of fluorescein labeled RNA encapsulated liposomes and functionalized with IL13 (mouse or human) or AntiCD155 antibodies (mouse or human). Cells were treated 4 hours in serum free medium and subjected to flow cytometry. (A)(B): mean eGFP intensity; (C)(D): gating of positive fluorescent cells.
Figure 4B:
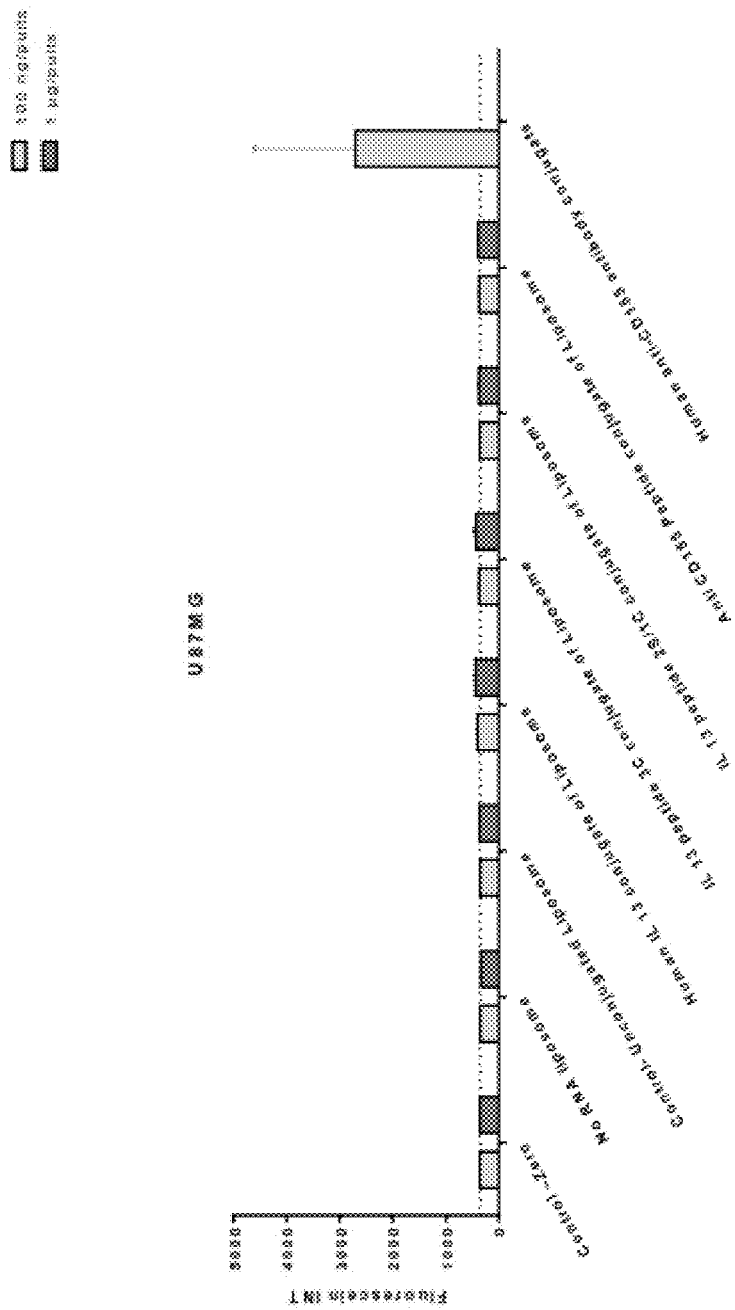
Figure 4C:
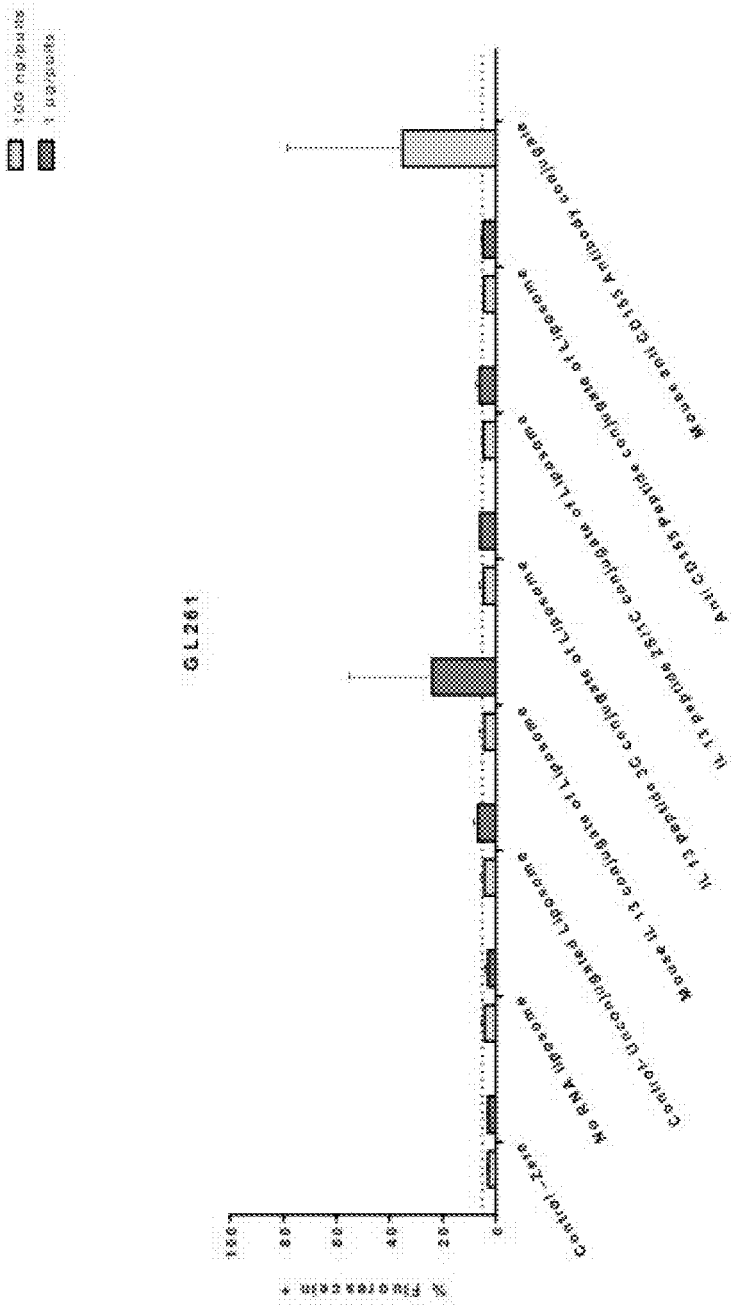
Figure 4D:
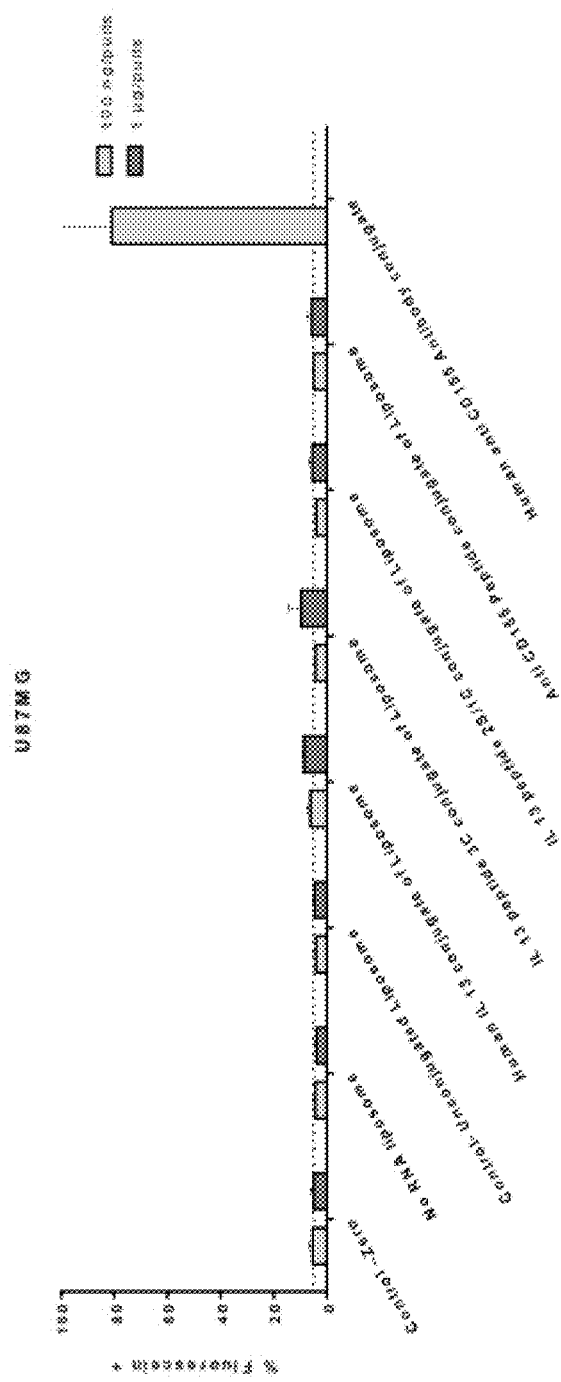
Figure 5:
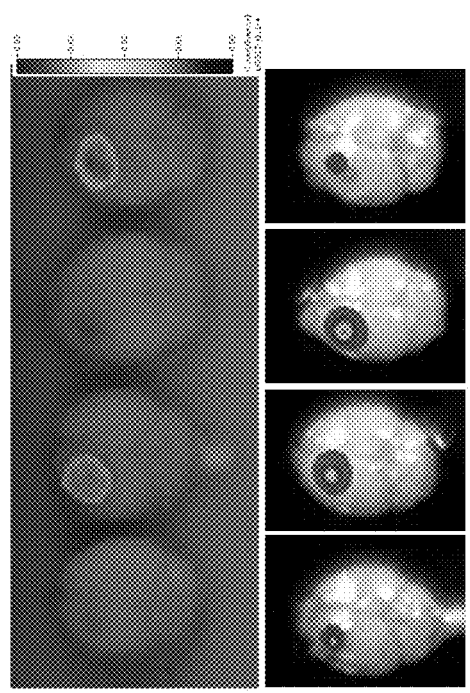
FIG. 5: Mice with GL261-Luciferase Tumors were administered either IV Phosphate Buffer Solution (Top Colum land 3) or IV Fluorescent Labelled Mouse AntiCD155 Antibody. In the mice administered the fluorescent labeled antibody, the fluorescent antibody concentrated at the site of the tumor suggesting the antibody crossed the blood brain barrier and bound to the tumor. No obvious fluorescence noted in the contralateral hemisphere.

Administration of Fluorescent Labelled Antibody in Mice with GL261-Luc implanted syngeneic tumor and Ex-Vivo fluorescence imaging & Bioluminescence imaging
FIG. 5: Mice with GL261-Luciferase Tumors were administered either IV Phosphate Buffer Solution (Top Colum 1 and 3) or IV Fluorescent Labelled Mouse AntiCD155 Antibody. In the mice administered the fluorescent labeled antibody, the fluorescent antibody concentrated at the site of the tumor suggesting the antibody crossed the blood brain barrier and bound to the tumor. No obvious fluorescence noted in the contralateral hemisphere.
Bottom Row: Ex vivo imaging of mice with G1261-Luc GBM tumors
Top Row: Ex Vivo Imaging of Mice treated with PBS or 50 ug IV fluorescent labeled Anti CD155 antibody. Column 2 and Column 4 administered IV mouse Anti-CD155 antibody labeled with fluorescent probe. Column 1 and Column 3 administered phosphate buffer solution.

Example 23

In Vivo Comparison of Fluorescent Labeled Anti-Mouse IL13alpha2 antibody and Fluorescent Labeled Anti-Mouse CD155 Antibody with regards to crossing Blood Brain Barrier in Mice and Binding GL261 Brain tumor in Mice
Anti-IL13alpha2 antibodies and Anti CD155 antibodies against the respective mouse receptor are labeled with Alexa-Fluor reporter. The conjugates are tested against the GL261 cell line in vitro. The conjugates are then to be tested in vivo by IV administration of the respective fluorophore labeled antibody in C57B16 mice with GBM tumor and control mice with no tumor. Control where the fluorophore alone is administered IV to one group of the mice with GBM to rule out non-specific uptake.

Example 24

In Vitro (Anti Human CD 155 Antibody and Anti Mouse CD155 Antibody) in Mouse GBM and Human GBM Cell lines and In Vivo Studies (Mice) of Anti Mouse CD155 Antibody coupled to Liposomes encapsulating mRNA alone or mRNA coencapsulated with Hemagglutinin A2 peptide in the presence and absence of Mefloquine or Chloroquine.
Different groups of three mice C57BL6 mice with GBM are being administered Anti Mouse CD155 Antibody coupled to Liposomes encapsulating mRNA alone or mRNA coencapsulated with Hemagglutinin A2 peptide. The same studies will then be performed in the presence of Chloroquine to determine if transfection is enhanced with co-administration.

Example 25

In Vitro ADCC experiments with Anti Human CD155 unmodified mouse IgG1 Antibody and Anti Human IgG1 Chimeric Human Fc Antibody optimized for ADCC. The target cells are CD155 positive cancer cell lines.

Example 26

Construction of Anti Human CD155 Antibody, Mouse IgG and Chimeric Anti Human CD155 antibody with Human IgG including one embodiment with a Selenocysteine modification to provide site of coupling Example 27

Humanization of Chimeric Anti Human CD155 Antibody

Example 28

16 Variants of Humanized Anti Human CD155 Antibody.

Example 29

Variant will be Modified with Fc region for enhancing ADCC.

Example 30

Modification of Humanized Anti Human CD155 antibody with Selenocysteine residue for coupling

Example 31

In vivo studies with Humanized Anti CD155 antibody, Selenocysteine modified Humanized Anti CD155 Antibody and ADCC optimized Fc-modified Humanized Anti CD155 Antibody

Example 32

In an embodiment, the anti-CD99 antibody molecule is a humanized or chimeric antibody. In an embodiment, the anti-CD99 antibody molecule is a polyclonal antibody. In an embodiment, the anti-CD99 antibody molecule is a monoclonal antibody.

Example 33

AntiCD155 antibody coupled to contrast agents for MRI/CT

Example 34

AntiCD155 antibody coupled to diagnostic agents for PET scan see list

Example 35

AntiCD155 antibody coupled to fluorescent probes (including but not limited to Alexa Fluor and/or Fluorescein) for in vivo identification of tumor

Example 36

Anti CD155 antibody coupled to radiosensitizers to enhance tumor susceptibility to radiation

Example 37

Anti CD155 coupled to Chelators

Example 38

AntiCD155 coupled to radioisotopes

Example 39

AntiCD155 coupled to any therapeutic

Example 40

AntiCD155 antibody (monoclonal or polyclonal) which is itself a therapeutic

Example 41

Anti-IL13α2 receptor and anti CD155 antibodies labeling
Experimental Procedure
Anti-IL13RA2 (Mouse anti-IL13RA2 Antibody—Polyclonal Rabbit IgG—ProteinTec 11059-1-AP) was purified through desalting column to remove sodium azide presents in the Ab solution and avoid interferences with CF680 dye conjugation Anti-CD155 (Mouse anti-CD155/PVR Antibody-Monoclonal Rat IgG2A Clone #690912 BioTechne) was purified through desalting column to remove trehalose presents in the Ab solution and avoid interferences with CF680 dye conjugation.

Anti-IL13RA2 and anti-CD155 antibodies were then labelled with CF680 fluorescent probe (Perkin-Elmer) and excess of fluorescent probe removed through dialysis.

Example 42

In vitro assessment of CD155/IL13α2 receptors expression in the presence of labeled antibodies
Experimental model
Mouse GL261-Luc2 glioblastoma cell line
Experimental procedure and treatment schedule
Cells were plated in their standard medium condition at an appropriate cellular density to yield about 80% confluency.
After 24 hours, cells were fixed and stained immunologically with
CF680 labeled anti-CD155 antibody
Unlabeled anti-CD155 antibody
CF680 labeled anti-IL13α receptor antibody
Unlabeled anti-IL13α receptor antibody
Signals were revealed with a fluorescent labelled secondary antibody
Additionally a nuclear and a whole cell fluorescent labelling was added to determine the cell contour.
Signals were analysed by High Content Imaging for analysis of the Ab signals at the membrane.
All conditions were performed in triplicate

Example 43

The signals from each antibody marker are analysed in the regions corresponding to detected membranes, the mean intensity is measured. The mean intensity outside cells is measured and subtracted from the values measured in cell membranes (background correction).

Example 44

Testing of labeled anti-IL13α2 receptor and anti-CD155 antibodies in vitro on the GL261-Luc2 cell line to assess if the antibodies maintain their binding capacity despite the fluorescent labeling.
In vitro assessment CD155/IL13α2 receptor expression in the presence of labeled antibodies
FIG. 12 depicts staining with anti-CD155 antibodies (A) membrane staining; (B) anti-CD155 antibody staining; and (C) membrane and anti-CD155 staining.
FIG. 13 depicts analyses of anti-CD155 antibody staining (A) mean staining intensity; (B) mean staining intensity with background correction.
FIG. 14 depicts staining with anti-IL13Ra2 antibodies (A) membrane staining; (B) anti-IL13Ra2 antibody staining; and (C) membrane and anti-IL13Ra2 staining.
FIG. 15 depicts analyses of anti-IL13Ra2 antibody staining (A) mean staining intensity; (B) mean staining intensity with background correction.
Control wells were good and had no staining visible with the secondary antibody alone and the membrane staining with the membrane probe is also satisfying.
For both targets, CD155 and IL13Ra2, the difference in staining intensity between the normal antibody form (anti CD155 antibody and anti IL13Ra2 antibody) and the conjugate done (anti CD155 antibody-CF680 conjugated and anti IL13Ra2 antibody-CF680 conjugated) is not statistically significant.

Thus we can conclude that the conjugation of the antibodies with the daylight-680 fluorophore does not affect their ability to bind their respective targets in-vitro.

Here is the p-value and significance for all the conditions tested:

TABLE 5

|  | Secondary antibody alone | Anti CD155 antibody | Anti CD 155 antibody-CF680 conjugated |
| --- | --- | --- | --- |
| Secondary antibody alone | — | — | — |
| Anti CD155 antibody | 0.0003/*** | — | — |
| Anti CD 155 antibody-CF680 conjugated | 0.0003/*** | 0.6299/ns | — |

TABLE 6

|  | Secondary antibody alone | Anti IL13Ra2 antibody | Anti IL13Ra2 antibody-CF680 conjugated |
| --- | --- | --- | --- |
| Secondary antibody alone | — | — | — |
| Anti IL13Ra2 antibody | 0.0006/*** | — | — |
| Anti IL13Ra2 antibody-CF680 conjugated | <0.0001/*** | 0.1660/ns | — |

Example 45

Evaluation of the ability of labeled anti-CD155 and anti-IL13α2R antibodies to cross the blood-brain-barrier in vivo in mice models 1. Experimental model C57Bl/6 mice bearing glioblastoma tumors (GL261-Luc2 cells)

Naïve C57Bl/6 mice

A total of 6 C57Bl/6 mice were implanted with GL261-Luc2 glioblastoma cells. After 24 days' post implantation, mice were treated as follows:

2 mice treated with anti-IL13α2 receptor labeled antibody by intravenous injection (50 Pg)

2 mice treated with anti-CD155 labeled antibody by intravenous injection (50 μg)

2 mice treated with CF680 dye by intravenous injection

Additionally, control groups composed of naïve C57Bl/6 mice were treated on the same day as the GL261-Luc2 glioblastoma-bearing mice, as follows:

2 mice treated with anti-IL13α2 receptor labeled antibody by intravenous injection (50 μg)

2 mice treated with anti-CD155 labeled antibody by intravenous injection (50 μg)

In total, 10 mice were used in this study.

2. Experimental procedure and treatment schedule

After 7 days of acclimation, 6 C57Bl/6 mice were implanted with GL261-Luc2 glioblastoma cells and 4 naïve C57Bl/6 mice were followed in parallel.

Tumor growth was followed by in vivo bioluminescence imaging 7, 14 and 21 days after cells implantation C57Bl/6 mice implanted with GL261-Luc2 glioblastoma cells were injected intravenously with CF680 dye or 50 μg of the CF680 conjugated anti-CD155 antibody or 50 μg of the CF680 conjugated anti-IL13RA2 antibody.

On the same time, naïve C57Bl/6 mice were injected intravenously with 50 μg of the CF680 conjugated anti-CD155 antibody or 50 μg of the CF680 conjugated anti-IL13RA2 antibody.

Fluorescence was captured using an in vivo fluorescence imager (FMT, Perkin-Elmer) at different time points after mAb injection, i.e. 4 hrs, 24 hrs, 48 hrs and 72 hrs.

After the last imaging, animals were sacrificed. Brains and peripheral organs (spinal cord pieces, GI, liver, lungs, spleen and kidney) were collected and subjected to ex vivo fluorescence imaging.

3. Assay endpoints/analysis

In vivo bioluminescence imaging of tumors at Days 7, Day 14, Day21

In vivo fluorescence imaging at different time points after mAb injection, i.e. 4 hrs, 24 hrs, 48 hrs and 72 hrs Ex vivo fluorescence imaging of Brains and peripheral organs—after the last in vivo imaging time point 4. Experimental Conditions 2 tumor bearing C57Bl/6 mice treated with anti-IL13α2 receptor labeled antibody by intravenous injection (50 μg)

2 tumor bearing C57Bl/6 mice treated with anti-CD155 labeled antibody by intravenous injection (50 μg)

2 tumor bearing C57Bl/6 mice treated with CF680 dye by intravenous injection 2 naïve C57Bl/6 mice treated with anti-IL13α2 receptor labeled antibody by intravenous injection (50 μg)

2 naïve C57Bl/6 mice treated with anti-CD155 receptor labeled antibody by intravenous injection (50 μg)

FIG. 16 depicts an experimental timeline to evaluate the ability of labeled anti-CD155 and anti-IL13α2R antibodies to cross the blood-brain-barrier in vivo in mouse models.

FIG. 17 depicts a graph of body weight versus days after cell implantation.

FIG. 18 depicts a graph of bioluminescence versus days after cell implantation.

FIG. 19 depicts localization of (A) CF680; (B) anti-CD155 mAb; (C) anti-IL13Ra2 mAb.

FIG. 20 depicts in vivo fluorescence whole body imaging using α-CD155 mAb in C57Bl/6 mice bearing (A) GL261-Luc2 glioblastoma cells or (B) naïve cells at 4 h, 24 h, 48 h, and 72 h.

FIG. 21 depicts in vivo fluorescence head imaging using anti-CD155 mAb in C57Bl/6 mice bearing (A) GL261-Luc2 glioblastoma cells or (B) naïve cells at 4 h, 24 h, 48 h, and 72 h;

FIG. 22 depicts the quantity of CF680 4 h, 24 h, 48 h, and 72 h for GL261-Luc2 and naïve cells.

FIG. 23 depicts in vivo fluorescence whole body imaging using α-IL13Ra2 mAb in C57Bl/6 mice bearing (A) GL261-Luc2 glioblastoma cells or (B) naïve cells at 4 h, 24 h, 48 h, and 72 h.

FIG. 24 depicts in vivo fluorescence head imaging using α-IL13Ra2 mAb in C57Bl/6 mice bearing (A) GL261-Luc2 glioblastoma cells or (B) naïve cells at 4 h, 24 h, 48 h, and 72 h;

FIG. 25 depicts the quantity of CF680 at 4 h, 24 h, 48 h, and 72 h for GL261-Luc2 and naïve cells.

FIG. 26 depicts in vivo fluorescence whole body imaging and head imaging using CF680 in C57Bl/6 mice bearing GL261-Luc2 glioblastoma cells at 4 h, 24 h, 48 h, and 72 h.

FIG. 27 depicts in vivo fluorescence imaging using anti-CD155 mAb, antiIL13Ra2mAb, or CF680 in C57Bl/6 mice bearing GL261-Luc2 glioblastoma cells at 4 h, 24 h, 48 h, and 72 h.

FIG. 28 depicts the quantity of CF680 at 4 h, 24 h, 48 h, and 72 h for CF680, anti-CD155 mAb, and antiIL13Ra2mAb.

FIG. 29 depicts in vivo fluorescence imaging using anti-CD155 mAb, antiIL13Ra2mAb, or CF680 in C57Bl/6 mice bearing GL261-Luc2 glioblastoma cells at 4 h, 24 h, 48 h, and 72 h.

FIG. 30 depicts in vivo fluorescence imaging using CF680, anti-CD155 mAb, or antiIL13Ra2mAb, in C57Bl/6 mice bearing GL261-Luc2 glioblastoma cells or naïve cells.

FIG. 31 depicts a bar graph of the fluorescence counts for CF680, anti-CD155 mAb, or antiIL13Ra2mAb in mice with or without GL261-Luc2 glioblastoma cells.

FIG. 32 depicts in vivo fluorescence imaging using anti-CD155 mAb, antiIL13Ra2mAb, or CF680 in C57Bl/6 mice bearing GL261-Luc2 glioblastoma cells or naïve cells.

In Vivo Imaging

There is only a weak detection of free CF680 dye within the head of tumor bearing mice.

The signal is observed 4 hours after intravenous injection of the dye but does not increase over time.

In contrast, both CF680 labelled antibodies display an intratumoral «accumulation» profile with increasing amounts observed over time and with maximal level detected between 48 and 72 hours.

Interestingly, this profile is not observed in naïve mice, where a weak signal is detectable 4 hours after injection but does not increase over time.

In peripheral organs, no clear difference between tumor bearing and naïve mice is observable.

However, a higher signal is noted for the kidney of mice exposed to CF680 labelled antiIL13Ra2 mAb—results also obtained ex-vivo.

Ex Vivo Imaging

Ex vivo imaging revealed that only tumor bearing mice accumulate CF680 labelled antibodies into their brain (at the tumor location). Only a weak signal is observable for CF680 alone.

Regarding naïve mice, the fact that no signal is detected within the brain here (ex vivo imaging) while a weak signal is observed during in vivo imaging, indicates that the antibodies are present in the brain—probably in vascular structures—but not within the tumor.

Also, it's interesting to note that higher amounts of antiIL13Ra2 mAb are detected within the tumor while this difference was not apparent in vivo.

These results are in accordance with a suitable use of CD155 and IL13 targets for further liposome targeting.

In vitro assessment of CD155/IL13α2 receptors expression in the presence of labelled antibodies.

TABLE 7

CD155 staining intensity in cell membrane

| Secondary antibody alone | Anti-CD155 antibody | Anti-CD155 antibody-CF680 conjugated |
|---|---|---|
| 399.9646 | 1138.547 | 1057.93 |
| 411.0626 | 1097.758 | 1090.951 |
| 416.68 | 953.9366 | 922.3735 |

TABLE 8

CD155 staining intensity in cell membrane (background corrected)

| Secondary antibody alone | Anti-CD155 antibody | Anti-CD155 antibody-CF680 conjugated |
|---|---|---|
| 4.885136 | 363.665 | 313.7027 |
| 13.34508 | 321.461 | 306.6242 |
| 6.630606 | 249.2141 | 288.7684 |

TABLE 9

IL13Ra2 staining intensity in cell membrane

| Secondary antibody alone | IL13Ra2 antibody | IL13Ra2 antibody-CF680 conjugated |
|---|---|---|
| 562.1025 | 1135.159 | 1379.123 |
| 553.2605 | 1103.125 | 1282.766 |
| 550.7399 | 1312.512 | 1265.076 |

TABLE 10

IL13Ra2 staining intensity in cell membrane (background corrected)

| Secondary antibody alone | IL13Ra2 antibody | IL13Ra2 antibody-CF680 conjugated |
|---|---|---|
| 6.665509 | 185.9558 | 253.7537 |
| 5.054727 | 204.7423 | 217.5944 |
| 7.99452 | 280.4715 | 245.7583 |

Raw Data: Step 3

In Vivo imaging: Quantification of CF680 dye (in pmoles) into the head of tumor bearing and naive mice exposed to CF680 dye, CF680 conjugated anti-CD155 mAb and CF680 conjugated antiIL13Ra2 mAb, 0, 4, 24, 48 and 72 hours after injection.

TABLE 11

| | GL261-Luc2 | | | | | | naïve | | | |
|---|---|---|---|---|---|---|---|---|---|---|
| | CF680 | | α-CD155 mAb | | A-IL13Ra2 mAb | | α-CD155 mAb | | A-IL13Ra2 mAb | |
| Mouse number | 11 | 17 | 12 | 13 | 1 | 18 | Ø | OD | OG | OD OG |
| 0 hrs | 0 | 0 | 0 | 0 | 0 | 0 | 0 | 0 | 0 | 0 |
| 4 hrs | 28.04 | 4.75 | 39.46 | 26.51 | 8.08 | 149.32 | 54.84 | 21.19 | 43.5 | 4.19 |
| 24 hrs | 17.49 | 10.98 | 0.35 | 41.89 | 95.48 | 32.02 | 44.8 | 25.31 | 7.65 | 22.91 |
| 48 hrs | 27.32 | 8.48 | 123.15 | 73.52 | 46.41 | 57.35 | 28.47 | 50.37 | 17.05 | 16.24 |
| 72 hrs | 24.44 | 8.55 | 75.12 | 93.11 | 107.71 | 82.3 | 22.3 | 43.01 | 23.96 | 21.74 |

Ex Vivo imaging: Quantification of CF680 dye (in pmoles) into the brain retrieved from tumor bearing and naive mice exposed to CF680 dye, CF680 conjugated anti-CD155 mAb and CF680 conjugated IL13Ra2 mAb 72 hours after injection.

TABLE 12

| | GL261-Luc2 | | | | | naïve | | |
|---|---|---|---|---|---|---|---|---|
| | CF680 | | α-CD155 mAb | | A-IL13Ra2 mAb | α-CD155 mAb | A-IL13Ra2 mAb | |
| Mouse number | 11 70.32 | 17 75.4 | 12 138.22 | 13 133.61 | 1 195.15 | 18 275.87 | Ø 51.29 | OD 48.72 | OG 56.32 | OD OG 48.52 |

FIG. 33 depicts various embodiments of monoclonal antibody binding to target cells. Depicted are (A) tumour-specific IgG; (B) angiogenesis inhibition; (C) checkpoint blockade; (D) radioimmunotherapy; (E) antibody-drug conjugate therapy; (F) bispecific antibody therapy; and (G) CAR T cells.

Example 46

A D171 antibody or similar antibody against CD155 will be chimerized with human IgG1 with selenocysteine coupled to a fluorescent label in order to demonstrate binding of an anti-CD155 antibody to human PVR in human tumors or human PVR transfected in GL261 tumors.
  Humanized Mouse with Intracranial Human GBM tumor (i.e., U87)
  Humanized Mouse with Peripheral Human GBM tumor (i.e., U87)
  057B16 Mouse with Intracranial Human PVR Transfected GL261 Mouse GBM Tumor
  057B16 Mouse with Peripheral Human PVR Transfected GL261 Mouse GBM Tumor
  Human PVR Transgenic C57B16 Mouse with Intracranial Human PVR Transfected GL261 Mouse GBM Tumor Example 47

D171 Antibody will be chimerized with human IgG1 optimized for ADCC in order to demonstrate that chimeric D171 with human IgG optimized for ADCC will cause lysis of in vivo human tumor.
  Humanized Mouse with Intracranial Human GBM Tumor (i.e., U87)
  Humanized Mouse with Peripheral Human GBM Tumor (i.e., U87)

As suggested above, the poliovirus receptor (PVR), also known as CD 155, is overexpressed in many cancers including glioblastoma, malignant meningioma, malignant peripheral nerve sheath tumors, pancreatic cancer, lung cancer, and GI malignanicies including colorectal cancer. The poliovirus receptor is also naturally found in healthy tissues, albeit with lower receptor densities, in cells such as motor neurons of the brain and spinal cord. There are known antibodies capable of binding to CD 155 with varying degrees of efficiency. One example of such a known antibody is the murine antibody where the heavy and light chains were incorporated into a human IgG1 chimerc antibody designated herein as Ab825. The heavy chain variable region (designated herein as VH0) and the light chain variable region (designated herein VK0) of Ab825 binds to the poliovirus receptor in human and non human primates. The heavy chain variable region VH0 is disclosed as Sequence ID NO 1 and the light chain variable region VK0 is disclosed as Sequence ID NO 5. The complementarity determining regions (CDRs) of VH0, CDR1, CDR2, and CDR3 are disclosed as Sequence ID NO 2, Sequence ID NO 3, and Sequence ID NO 4, respectively. The CDRs of VK0, CDR1, CDR2 and CDR3 are disclosed as Sequence ID NO 6, Sequence ID NO 7, and Sequence ID NO 8, respectively.

One aspect of the present invention involves modifying and humanizing this heavy chain variable (VH) region and light chain variable (VK) region in order to make the antibody more stable and to minimize the immunogenicity and toxicity when the antibodies are used for therapeutic and diagnostic purposes in living humans. To form such antibodies or antibody fragments, the designed variable region genes were cloned into vectors encoding a human IgG1 heavy chain constant domain and a human kappa light chain constant domain. Chimeric and humanized antibodies were transiently expressed in CHO cells, purified by Protein A and tested for binding to the PVR using Biacore.

Structural models of the Ab825 antibody variable regions were produced and analyzed in order to identify important constraining amino acids in the variable regions that were likely to be essential for the binding properties of the antibody. Based upon this structural analysis, a large preliminary set of sequence segments were identified that could be used to create Ab825 humanized variants. These segments were selected and analysed for in silico analysis of peptide binding to human MHC class II alleles and comparing to known antibody sequence-related T cell epitopes. Sequence segments that were identified as significant non-human germline binders to human MHC class II or that scored significant hits in our analysis were discarded. This resulted in a reduced set of segments, and combinations of these were again analysed, as above, to ensure that the junctions between segments did not contain potential T cell epitopes. Selected sequence segments were assembled into complete variable region sequences that were devoid of significant T cell epitopes.

Employing the above analysis, five variable region heavy chains (designated VH1 to VH5) and four variable regions light chains (designated VK1 to VK4) were identified as having enhanced binding properties. These regions are disclosed by the following sequence ID Nos:

| Sequence ID Number | Sequence Designation |
|---|---|
| SEQ ID NO. 9 | VH1 |
| SEQ ID NO. 10 | VH2 |
| SEQ ID NO. 11 | VH3 |
| SEQ ID NO. 12 | VH4 |
| SEQ ID NO. 13 | VH5 |
| SEQ ID NO. 14 | VK1 |
| SEQ ID NO. 15 | VK2 |
| SEQ ID NO. 16 | VK3 |
| SEQ ID NO. 17 | VK4 |

In one embodiment, the invention is an antibody or antibody fragment against the poliovirus receptor (CD155) of an IgG isotype. This antibody or antibody fragment will have a heavy chain variable region from any one of SEQ ID NOS. 1, 9, 10, 11, 12, or 13 with a CDR 1 of SEQ ID NO. 2 and a CDR 3 of SEQ ID NO. 4. The CDR2 will be SEQ ID NO. 3, but with one or more of the following modifications:
  (1) the asparagine in the sixth position of CDR 2 is substituted with one of alanine, glutamic acid, lysine, glutamine, serine, or threonine; and/or
  (2) the aspartic acid in the eighth position of CDR 2 is substituted with one of glutamic acid, glycine, or arginine; and/or
  (3) the threonine in the ninth position of CDR 2 is substituted with one of glutamic acid or lysine.

The light chain variable region will be any one of SEQ ID NOS. 5, 14, 15, 16, or 17 with a CDR 1 of SEQ ID NO. 6 and a CDR 2 of SEQ ID NO. 7. The CDR3 will be SEQ ID NO. 8, but with the asparagine in the fourth position of CDR 3 being substituted with one of alanine, glutamic acid, glycine, lysine, glutamine, or serine.

In another embodiment, the antibody or antibody fragment against the poliovirus receptor (CD155) is an IgG isotype. However, in this embodiment, the heavy chain variable region and light chain variable region are defined in terms of their CDRs. For example, the heavy chain variable region will include the VH0 CDR 1 of SEQ ID NO. 2 and the VH0 CDR 3 of SEQ ID NO. 4. Again, the VH0 CDR2 will be SEQ ID NO. 3, but with one or more of the following modifications:
  (1) the asparagine in the sixth position of CDR 2 is substituted with one of alanine, glutamic acid, lysine, glutamine, serine, or threonine; and/or
  (2) the aspartic acid in the eighth position of CDR 2 is substituted with one of glutamic acid, glycine, or arginine; and/or
  (3) the threonine in the ninth position of CDR 2 is substituted with one of glutamic acid or lysine.

The light chain variable region will have the VK0 CDR 1 of SEQ ID NO. 6 and the VK0 CDR 2 of SEQ ID NO. 7. The VK0 CDR3 will be SEQ ID NO. 8, but with the asparagine in the fourth position of CDR 3 being substituted with one of alanine, glutamic acid, glycine, lysine, glutamine, or serine.

More preferred antibody embodiments were developed from particular combinations of the previously described heavy chain variable regions VH1-VH5 (SEQ ID NOS: 9-13) and light chain variable regions VK1-VK4 (SEQ ID NOS: 14-17). VH3 and VH4, together with VK2 and VK3 were deemed among the best variable heavy chain and light chain humanized variants based on the T cell epitope profile.

To address the potential deamidation sites identified at VH N54 and VK N92 (using single letter amino acid symbols and the amino acid position number) and the potential isomerisation site associated with VH D56, a series of amino acid substitutions (six for the potential sequence liabilities at VH N54 and VK N92 and five for VH D56) were first introduced individually into the VH and VK regions by mutations in the VH0/VK0 chimeric antibody. The liability reduced substitutions in VH0/VK0 included mutations at VH N54Q, N54S, D56E and D56G together with VK N92E and N92Q and these variants of VH0/VK0 were tested for binding to the poliovirus receptor, and upon analysis of binding, were then selected to be incorporated in combination into certain preferred humanized variants of VH3/VK2, VH3/VK3 and VH4/VK3. These modified VH and VK regions have the following sequence and designation:

| Sequence ID Number | Designation of Sequence |
|---|---|
| SEQ ID NO. 18 | VH3 N54Q D56E |
| SEQ ID NO. 19 | VK2 N92E |
| SEQ ID NO. 20 | VH3 N54S D56G |
| SEQ ID NO. 21 | VK2 N92Q |
| SEQ ID NO. 22 | VK3 N92E |
| SEQ ID NO. 23 | VK3 N92Q |
| SEQ ID NO. 24 | VH4 N54Q D56E |
| SEQ ID NO. 25 | VH4 N54S D56G |
| SEQ ID NO. 26 | VH4 N54S D56E |

Employing these VH and VK regions, nine preferred antibody (or antibody fragments) against the poliovirus receptor (CD155) were identified, having the following heavy chain variable region and light chain variable region, respectively:
  (i) VH3 N54Q D56E [SEQ ID NO: 18] and VK2 N92E [SEQ ID NO: 19];
  (ii) VH3 N54S D56G [SEQ ID NO: 20] and VK2 N92Q [SEQ ID NO: 21];
  (iii) VH3 N54Q D56E [SEQ ID NO: 18] and VK3 N92E [SEQ ID NO: 22];
  (iv) VH3 N54S D56G [SEQ ID NO: 20] and VK3 N92Q [SEQ ID NO: 23];
  (v) VH4 N54Q D56E [SEQ ID NO: 24] and VK3 N92E [SEQ ID NO: 22];
  (vi) VH4 N54S D56E [SEQ ID NO: 26] and VK3 N92E [SEQ ID NO: 22];
  (vii) VH4 N54S D56G [SEQ ID NO: 25] and VK3 N92E [SEQ ID NO: 22];
  (viii) VH4 N54Q D56E [SEQ ID NO: 24] and VK3 N92Q [SEQ ID NO: 23];
  (ix) VH4 N54S D56G [SEQ ID NO: 25] and VK3 N92Q [SEQ ID NO: 23].

Further testing of these nine antibodies suggested the most preferred binding profiles were found in the antibodies (ii) VH3 N54S D56G [SEQ ID NO: 20] and VK2 N92Q [SEQ ID NO: 21]; (iv) VH3 N54S D56G [SEQ ID NO: 20] and VK3 N92Q [SEQ ID NO: 23]; and (ix) VH4 N54S D56G [SEQ ID NO: 25] and VK3 N92Q [SEQ ID NO: 23].

In addition to the antibodies described above, the present invention is intended to encompass the novel heavy chain variable regions and light chain variable regions forming the antibodies. For example, the VH regions identified in SEQ ID NOS: 9-13 and 18, 20, and 24-26, as well as the VK regions identified in SEQ ID NOS: 14-17, 19, and 21-23, should each be considered a separate invention.

Likewise, the invention contemplates not only the antibodies and antibody fragments, but also DNA encoding the antibodies or antibody fragments, as well as any other polynucleotide or plasmid comprising a nucleotide sequence encoding the antibodies or antibody fragments.

Those skilled in the art will recognize that the antibodies or antibody fragments described above can be conjugated to at least one marker compound such as the fluorophore, IR 800 Dye. The antibodies and antibody fragment can also easily be radiolabeled with radioactive labels such as 1-124. The antibodity or antibody fragments may be conjugated to at least one drug (Antibody Drug Conjugate), such as paclitaxel, temozolomide or doxurubicin. The antibodies or antibody fragments can also be conjugated to one or more therapeutic nucleic acids being delivered via antibodies or antibody fragments, where the therapeutic nucleic acid is any one or more of silencing RNA, shRNA, long RNA, ribozyme, messenger RNA, a plasmid DNA, or non-plasmid double stranded DNA and short single and double stranded DNA.

As suggested above, the antibodies or antibody fragments described herein may be of an IgG isotype such as IgG1 IgG2 or IgG4. One embodiment includes an IgG4 antibody variant with a hinge mutation such as a S228P mutation to prevent an Fab arm exchange. The IgG isotype antibodies or antibody fragments can be conjugated to cytokines such as Interleukin 12 (IL12) or the antibody or antibody fragments against the PVR can be incorporated into a chimeric antigen receptor T-cell.

Cancers can be treated by injecting into a patient the antibody, an antibody fragment, or a DNA encoding the antibody or antibody fragment of any one of the above described antibodies, wherein the injection is at least one of intravenous, intra-arterial, intramuscular, intrathecal, intraventricular, intra tumoral, subcutaneous, or intralymphatic. Similarly, the antibody or antibody fragment or antibody drug conjugate or radiolabeled antibody or antibody nucleic acid conjugate can be injected into cerebrospinal fluid or directly into a brain tumor through a catheter.

This application incorporates by reference herein in its entirety U.S. Provisional Application Ser. No. 62/791,966, filed Jan. 14, 2019.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An antibody of an IgG1 or IgG4 isotype against the poliovirus receptor (CD155) or an antigen-binding fragment thereof comprising a heavy chain variable region and a light chain variable region, wherein the heavy chain variable region and the light chain variable region, respectively, comprise the amino acid sequences of one of the following:

(i) SEQ ID NO: 18 and SEQ ID NO: 19;
(ii) SEQ ID NO: 20 and SEQ ID NO: 21;
(iii) SEQ ID NO: 18 and SEQ ID NO: 22;
(iv) SEQ ID NO: 20 and SEQ ID NO: 23;
(v) SEQ ID NO: 24 and SEQ ID NO: 22;
(vi) SEQ ID NO: 26 and SEQ ID NO: 22;
(vii) SEQ ID NO: 25 and SEQ ID NO: 22;
(viii) SEQ ID NO: 24 and SEQ ID NO: 23; and
(ix) SEQ ID NO: 25 and SEQ ID NO: 23.

2. The antibody or antigen-binding fragment thereof of claim 1, wherein the heavy chain variable region and light chain variable region, respectively, comprise the amino acid sequences of SEQ ID NO: 25 and SEQ ID NO: 23.

3. An isolated nucleic acid or plasmid comprising a nucleotide sequence encoding the antibody or antigen-binding fragment thereof according to any one of claims 1 and 2.

4. The antibody or antigen-binding fragment of any one of claims 1 and 2, which is conjugated to at least one marker compound.

5. The antibody or antigen-binding fragment of claim 4, wherein the at least one marker compound is I-124, a fluorophore, or IR800 Dye.

6. The antibody or antigen-binding fragment of any one of claims 1 and 2, which is conjugated to at least one drug.

7. The antibody or antigen-binding fragment of claim 6, wherein the at least one drug is paclitaxel, doxorubicin, or temozolomide.

8. The antibody or antigen-binding fragment of any one of claims 1 and 2, which is conjugated to at least one therapeutic nucleic acid.

9. The antibody or antigen-binding fragment of claim 8, wherein the at least one therapeutic nucleic acid is a silencing RNA (siRNA), long RNA, shRNA, ribozyme, messenger RNA, a plasmid DNA, a non-plasmid double stranded DNA, or a short single stranded DNA.

10. The antibody or antigen-binding fragment of any one of claims 1 and 2, wherein the antibody or antigen-binding fragment is of an IgG4 isotype.

11. The antibody or antigen-binding fragment of claim 10, wherein the antibody or antigen-binding fragment is conjugated to IL12.

12. A method of treating cancer comprising the step of injecting into a patient the antibody or antigen-binding fragment thereof of any one of claims 1 and 2, or a DNA encoding the antibody or antibody fragment antigen-binding fragment thereof of any one of claims 1 and 2, wherein the injection is at least one of intravenous, intramuscular, intra-arterial, intrathecal, intraventricular, intra: tumoral, subcutaneous, and intralymphatic.

13. The method of claim 12, wherein the injection is into cerebrospinal fluid.

14. The method of claim 12, wherein the injection is into a brain tumor through a catheter.

15. The method of claim 12, wherein the antibody or antigen-binding fragment thereof is conjugated to a drug and injected into a tumor.

16. An antibody against the poliovirus receptor (CD155) or an antigen-binding fragment thereof comprising:
   (a) a heavy chain variable region comprising SEQ ID NO: 25; and
   (b) a light chain variable region comprising SEQ ID NO: 23.

\* \* \* \* \*

SEQUENCE LISTING

```
<160> NUMBER OF SEQ ID NOS: 26

<210> SEQ ID NO 1
<211> LENGTH: 116
<212> TYPE: PRT
<213> ORGANISM: Artificial Sequence
<220> FEATURE:
<223> OTHER INFORMATION: synthesized sequence

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile His Pro Asn Asn Gly Asp Thr Ser Tyr Asn Gln Arg Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Thr Gly Asp Phe Asp Tyr Trp Gly Gln Gly Thr Thr Leu
            100                 105                 110

Thr Val Ser Thr
        115

<210> SEQ ID NO 2
<211> LENGTH: 5
<212> TYPE: PRT
<213> ORGANISM: Artificial Sequence
<220> FEATURE:
<223> OTHER INFORMATION: synthesized sequence

<400> SEQUENCE: 2

Glu Tyr Thr Met His
1               5

<210> SEQ ID NO 3
<211> LENGTH: 17
```

```
<212> TYPE: PRT
<213> ORGANISM: Artificial Sequence
<220> FEATURE:
<223> OTHER INFORMATION: synthesized sequence

<400> SEQUENCE: 3

Gly Ile His Pro Asn Asn Gly Asp Thr Ser Tyr Asn Gln Arg Phe Lys
1               5                   10                  15

Gly

<210> SEQ ID NO 4
<211> LENGTH: 7
<212> TYPE: PRT
<213> ORGANISM: Artificial Sequence
<220> FEATURE:
<223> OTHER INFORMATION: synthesized sequence

<400> SEQUENCE: 4

Trp Thr Gly Asp Phe Asp Tyr
1               5

<210> SEQ ID NO 5
<211> LENGTH: 107
<212> TYPE: PRT
<213> ORGANISM: Artificial Sequence
<220> FEATURE:
<223> OTHER INFORMATION: synthesized sequence

<400> SEQUENCE: 5

Asp Ile Val Met Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: synthesized sequence

<400> SEQUENCE: 6

Lys Ala Ser Gln Asn Val Gly Thr Asn Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: synthesized sequence

<400> SEQUENCE: 7
```

Ser Ala Ser Tyr Arg Tyr Ser
1               5

<210> SEQ ID NO 8
<211> LENGTH: 9
<212> TYPE: PRT
<213> ORGANISM: Artificial Sequence
<220> FEATURE:
<223> OTHER INFORMATION: synthesized sequence

<400> SEQUENCE: 8

Gln Gln Tyr Asn Ser Tyr Pro Tyr Thr
1               5

<210> SEQ ID NO 9
<211> LENGTH: 116
<212> TYPE: PRT
<213> ORGANISM: Artificial Sequence
<220> FEATURE:
<223> OTHER INFORMATION: synthesized sequence

<400> SEQUENCE: 9

Glu Val Gln Leu Gln Gln Ser Gly Pro Glu Leu Lys Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Pro His Gly Lys Gly Leu Glu Trp Ile
            35                  40                  45

Gly Gly Ile His Pro Asn Asn Gly Asp Thr Ser Tyr Asn Gln Arg Phe
        50                  55                  60

Lys Gly Arg Ala Thr Leu Thr Val Asp Lys Ser Thr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Thr Gly Asp Phe Asp Tyr Trp Gly Gln Gly Thr Thr Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: synthesized sequence

<400> SEQUENCE: 10

Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Pro His Gly Lys Gly Leu Glu Trp Ile
            35                  40                  45

Gly Gly Ile His Pro Asn Asn Gly Asp Thr Ser Tyr Asn Gln Arg Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val

```
                    100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: synthesized sequence

<400> SEQUENCE: 11

Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Asn Gly Asp Thr Ser Tyr Asn Gln Arg Phe
        50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
                100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: synthesized sequence

<400> SEQUENCE: 12

Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Asn Gly Asp Thr Ser Tyr Asn Gln Arg Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
                100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
```

<223> OTHER INFORMATION: synthesized sequence

<400> SEQUENCE: 13

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Pro Pro Gly Lys Gly Leu Glu Trp Ile
        35                  40                  45

Gly Gly Ile His Pro Asn Asn Gly Asp Thr Ser Tyr Asn Gln Arg Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
            115

<210> SEQ ID NO 14
<211> LENGTH: 107
<212> TYPE: PRT
<213> ORGANISM: Artificial Sequence
<220> FEATURE:
<223> OTHER INFORMATION: synthesized sequence

<400> SEQUENCE: 14

Asp Ile Val Met Thr Gln Ser Pro Ser Phe Met Ser Thr Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: synthesized sequence

<400> SEQUENCE: 15

Asp Ile Val Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Thr Gly

```
                50                  55                  60
Ser Gly Ser Gly Thr Asp Phe Thr Leu Thr Ile Ser Ser Leu Gln Ala
 65                  70                  75                  80

Glu Asp Leu Ala Glu Tyr Phe Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: synthesized sequence

<400> SEQUENCE: 16

Asp Ile Gln Met Thr Gln Ser Pro Ser Ala Met Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Gln Pro Pro Lys Ala Leu Ile
             35                  40                  45

Tyr Ser Ala Ser Tyr Arg Tyr Ser Gly Val Pro Asp Arg Phe Ser Gly
         50                  55                  60

Ser Gly Ser Gly Thr Asp Phe Thr Leu Thr Ile Ser Ser Leu Gln Ala
 65                  70                  75                  80

Glu Asp Leu Ala Glu Tyr Phe Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: synthesized sequence

<400> SEQUENCE: 17

Asp Ile Gln Met Thr Gln Ser Pro Ser Ala Met Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Gln Pro Pro Lys Ala Leu Ile
             35                  40                  45

Tyr Ser Ala Ser Tyr Arg Tyr Ser Gly Val Pro Asp Arg Phe Ser Gly
         50                  55                  60

Ser Gly Ser Gly Thr Asp Phe Thr Leu Thr Ile Ser Ser Leu Gln Ala
 65                  70                  75                  80

Glu Asp Leu Ala Glu Tyr Tyr Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 18
<211> LENGTH: 116
<212> TYPE: PRT
<213> ORGANISM: Artificial Sequence
<220> FEATURE:
```

<223> OTHER INFORMATION: synthesized sequence

<400> SEQUENCE: 18

| Glu | Val | Gln | Leu | Val | Gln | Ser | Gly | Ser | Glu | Leu | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Val Lys Ile Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Gln Gly Glu Thr Ser Tyr Asn Gln Arg Phe
50                      55                      60

Lys Gly Arg Val Thr Leu Thr Val Asp Lys Ser Thr Ser Thr Ala Tyr
65                      70                      75                  80

Met Glu Leu Ser Ser Leu Arg Ser Glu Asp Thr Ala Val Tyr Tyr Cys
                85                      90                      95

Ala Arg Trp Thr Gly Asp Phe Asp Tyr Trp Gly Gln Gly Thr Leu Val
            100                 105                 110

Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: synthesized sequence

<400> SEQUENCE: 19

Asp Ile Val Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Gln Pro Pro Lys Ala Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Glu Ser Tyr Pro Tyr
                85                  90                  95

Thr Phe Gly Gln Gly Thr Lys Leu Glu Ile Lys
            100                 105

<210> SEQ ID NO 20
<211> LENGTH: 116
<212> TYPE: PRT
<213> ORGANISM: Artificial Sequence
<220> FEATURE:
<223> OTHER INFORMATION: synthesized sequence

<400> SEQUENCE: 20

Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Ser Gly Gly Thr Ser Tyr Asn Gln Arg Phe

```
            50                  55                  60
Lys Gly Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Trp Thr Gly Asp Phe Asp Tyr Trp Gly Gln Gly Thr Leu Val
                100                 105                 110

Thr Val Ser Ser
            115

<210> SEQ ID NO 21
<211> LENGTH: 107
<212> TYPE: PRT
<213> ORGANISM: Artificial Sequence
<220> FEATURE:
<223> OTHER INFORMATION: synthesized sequence

<400> SEQUENCE: 21

Asp Ile Val Met Thr Gln Ser Pro Ser Ala Met Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Gln Pro Pro Lys Ala Leu Ile
             35                  40                  45

Tyr Ser Ala Ser Tyr Arg Tyr Ser Gly Val Pro Asp Arg Phe Thr Gly
         50                  55                  60

Ser Gly Ser Gly Thr Asp Phe Thr Leu Thr Ile Ser Ser Leu Gln Ala
 65                  70                  75                  80

Glu Asp Leu Ala Glu Tyr Phe Cys Gln Gln Tyr Gln Ser Tyr Pro Tyr
                     85                  90                  95

Thr Phe Gly Gln Gly Thr Lys Leu Glu Ile Lys
                100                 105

<210> SEQ ID NO 22
<211> LENGTH: 107
<212> TYPE: PRT
<213> ORGANISM: Artificial Sequence
<220> FEATURE:
<223> OTHER INFORMATION: synthesized sequence

<400> SEQUENCE: 22

Asp Ile Gln Met Thr Gln Ser Pro Ser Ala Met Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Gln Pro Pro Lys Ala Leu Ile
             35                  40                  45

Tyr Ser Ala Ser Tyr Arg Tyr Ser Gly Val Pro Asp Arg Phe Ser Gly
         50                  55                  60

Ser Gly Ser Gly Thr Asp Phe Thr Leu Thr Ile Ser Ser Leu Gln Ala
 65                  70                  75                  80

Glu Asp Leu Ala Glu Tyr Phe Cys Gln Gln Tyr Glu Ser Tyr Pro Tyr
                     85                  90                  95

Thr Phe Gly Gln Gly Thr Lys Leu Glu Ile Lys
                100                 105

<210> SEQ ID NO 23
<211> LENGTH: 107
```

```
<212> TYPE: PRT
<213> ORGANISM: Artificial Sequence
<220> FEATURE:
<223> OTHER INFORMATION: synthesized sequence

<400> SEQUENCE: 23

Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Gln Ser Tyr Pro Tyr
                85                  90                  95

Thr Phe Gly Gln Gly Thr Lys Leu Glu Ile Lys
                100                 105

<210> SEQ ID NO 24
<211> LENGTH: 116
<212> TYPE: PRT
<213> ORGANISM: Artificial Sequence
<220> FEATURE:
<223> OTHER INFORMATION: synthesized sequence

<400> SEQUENCE: 24

Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Gln Gly Glu Thr Ser Tyr Asn Gln Arg Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
                100                 105                 110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: synthesized sequence

<400> SEQUENCE: 25

Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
```

```
                35                  40                  45
Gly Gly Ile His Pro Asn Ser Gly Gly Thr Ser Tyr Asn Gln Arg Phe
        50                  55                  60
Lys Gly Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Trp Thr Gly Asp Phe Asp Tyr Trp Gly Gln Gly Thr Leu Val
            100                 105                 110
Thr Val Ser Ser
            115

<210> SEQ ID NO 26
<211> LENGTH: 116
<212> TYPE: PRT
<213> ORGANISM: Artificial Sequence
<220> FEATURE:
<223> OTHER INFORMATION: synthesized sequence

<400> SEQUENCE: 26

Glu Val Gln Leu Val Gln Ser Gly Ser Glu Leu Lys Lys Pro Gly Ala
1               5                   10                  15
Ser Val Lys Val Ser Cys Lys Thr Ser Gly Tyr Thr Phe Thr Glu Tyr
                20                  25                  30
Thr Met His Trp Val Arg Gln Pro His Gly Lys Gly Leu Glu Trp Ile
            35                  40                  45
Gly Gly Ile His Pro Asn Ser Gly Glu Thr Ser Tyr Asn Gln Arg Phe
        50                  55                  60
Lys Gly Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Trp Thr Gly Asp Phe Asp Tyr Trp Gly Gln Gly Thr Leu Val
            100                 105                 110
Thr Val Ser Ser
            115
```